United States Patent
Truneh et al.

(10) Patent No.: US 11,945,871 B2
(45) Date of Patent: *Apr. 2, 2024

(54) ANTI-BTN3A ANTIBODIES AND THEIR USE IN TREATING CANCER OR INFECTIOUS DISORDERS

(71) Applicants: Imcheck Therapeutics SAS, Marseilles (FR); INSERM (Institut National de la Santé et de la Recherche Médicale), Paris (FR); Université d'Aix Marseille, Marseilles (FR); Institut Jean Paoli & Irene Calmette, Marseilles (FR); Centre National de la Recherche Scientifique—CNRS, Paris (FR)

(72) Inventors: Alemseged Truneh, Sudbury, MA (US); Daniel Olive, Marseilles (FR); Christine Pasero, Marseilles (FR); Aude De Gassart, Marseilles (FR)

(73) Assignees: IMCHECK THERAPEUTICS SAS, Marseilles (FR); INSERM (INSTITUT NATIONAL DE LA SANTE ET DE LA RECHERCHE MEDICALE), Paris (FR); UNIVERSITE AIX MARSEILLE, Marseilles (FR); INSTITUT JEAN PAOLI & IRENE CALMETTE, Marseilles (FR); CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/327,127

(22) Filed: Jun. 1, 2023

(65) Prior Publication Data
US 2023/0322932 A1   Oct. 12, 2023

Related U.S. Application Data

(63) Continuation of application No. 17/935,154, filed on Sep. 26, 2022, which is a continuation of application No. 17/264,507, filed as application No. PCT/EP2019/070693 on Jul. 31, 2019.

(30) Foreign Application Priority Data

Aug. 1, 2018 (EP) .................................... 18306050
Jan. 28, 2019 (EP) .................................... 19153992

(51) Int. Cl.
*C07K 16/28* (2006.01)
*A61K 9/19* (2006.01)
*A61K 38/20* (2006.01)
*A61K 39/395* (2006.01)
*A61P 35/00* (2006.01)
*A61K 39/00* (2006.01)

(52) U.S. Cl.
CPC ............ *C07K 16/2827* (2013.01); *A61K 9/19* (2013.01); *A61K 38/2013* (2013.01); *A61K 38/2086* (2013.01); *A61K 39/3955* (2013.01); *A61P 35/00* (2018.01); *C07K 16/2818* (2013.01); *A61K 39/00* (2013.01); *A61K 2039/505* (2013.01); *A61K 2039/507* (2013.01); *C07K 2317/56* (2013.01)

(58) Field of Classification Search
None
See application file for complete search history.

(56) References Cited

U.S. PATENT DOCUMENTS

| | | | |
|---|---|---|---|
| 2022/0112289 A1* | 4/2022 | Truneh | A61P 35/02 |
| 2023/0227558 A1* | 7/2023 | Valentin | A61K 39/39541 424/134.1 |
| 2023/0272080 A1* | 8/2023 | Truneh | A61K 39/3955 424/133.1 |

OTHER PUBLICATIONS

Ribal'skii, N. G. et al., "Monoclonal Antibodies and Hybridomas", SCST State Committee for Inventions and Discoveries, 1969.

* cited by examiner

*Primary Examiner* — Ilia I Ouspenski
(74) *Attorney, Agent, or Firm* — WCF IP

(57) ABSTRACT

The present invention relates to humanized antibodies that specifically bind to human BTN3A and their use in treating cancer and infectious disorders.

14 Claims, 5 Drawing Sheets
Specification includes a Sequence Listing.

A
B

ANTI-BTN3A ANTIBODIES AND THEIR USE IN TREATING CANCER OR INFECTIOUS DISORDERS

SEQUENCE LISTING

This document incorporates by reference an electronic sequence listing xml file, which was electronically submitted on Jun. 1, 2023. The xml file is named 2023-06-01_13500126US3_seqlisting.xml, is 28,558 bytes, and was created on Jun. 1, 2023.

It is hereafter disclosed anti-BTN3A activating antibodies that specifically bind to BTN3A and activate the cytolytic function of Vγ9/Vδ2 T cells. Such antibodies are useful in particular in treating cancer disorders, such as blood cancer or solid tumors. The disclosure more specifically relates to specific humanized anti-BTN3A activating antibodies, with equivalent or improved properties as compared to the corresponding parental murine antibodies 7.2, or their chimeric versions with Fc-silenced human IgG1 or IgG4 constant regions.

BACKGROUND

White blood cells are cells of the immune system involved in defending the body against pathogens. Among these cells, lymphocytes, monocytes, and dendritic cells can be cited. Monocytes may migrate from the bloodstream to other tissues and differentiate into tissue resident macrophages or dendritic cells. Dendritic cells play a role as antigen presenting cells (APC) that activate lymphocytes. Among lymphocytes, T cells can be divided into αβ T cells and γδ T cells. Vγ9-Vδ2, a subset of γδ T cells, are important effectors of the immune defense system. They directly lyse pathogen infected or abnormal cells. In addition, they regulate immune responses by inducing dendritic cell (DC) maturation as well as isotype switching and immunoglobulin production. This important cell subset of the immune system is tightly regulated by surface receptors, chemokines and cytokines.

The priming of T cells is modulated by involvement of specialized cells and secretion of chemotactic cytokines. The two-signal hypothesis posits that T-cell activation is the result of two synergistic events. The first is the interaction between T cell receptors (TCR) and the major histocompatibility complex (MHC) in complex with processed antigen on the surface of the antigen presenting cells (APC). The second event is a co-stimulatory antigen-independent signal involving CD28 and B7 molecules. The lack of co-stimulatory signals induces anergy and non-responsiveness, resulting in the absence of T cells proliferation, cytokines secretion, and cytotoxic activities. The study of these pathways provides insights into the triggering of pathological events, such as autoimmune or lymphoproliferative disorders. The B7 family is an extended group of costimulatory molecules (Coyle and Gutierrez-Ramos, 2001; Sharpe and Freeman, 2002). To the B7 family belong the ligands B7-1 (CD80) and B7-2 (CD86): their receptors are CD28, which leads to T cell activation, and CTLA-4 (CD152), which competes with CD28 and transduces an inhibitory signal (reviewed in Alegre et al., 2001). The critical role of CD152 as a negative regulator of T cell activation is demonstrated by the occurrence of lymphoproliferative disorders in CTLA-4 deficient mice. Important findings on the inhibitory function exerted by CD152 come from studies of proliferation or cytokine production by naive T lymphocytes during T cell priming. In particular, CD152 is expressed following T-lymphocyte activation and inhibits the cytolytic functions of CTL clones obtained following PHA stimulation or Ag selection. B7-H1 (PD-L1, CD274) and B7-DC (PD-L2, CD273), whose receptor is PD-1 (CD279), proved to inhibit T-cell proliferation and cytokine secretion (reviewed in Sharpe and Pauken, 2018). Otherwise, different studies showed that PD-L1 and PD-L2 engagement increase T cell proliferation and IL-10 or IFN-γ production. Other molecules related to the B7 family expressed on the surface of T cells, including B7-H2 (ICOS-L), the more recently identified B7-H3, B7-H4, B7-H5, B7-H6, and B7-H7 have also been implicated as checkpoint regulators of immune function (reviewed in Ni and Dong, 2017)

Henry et al. (1999) found that the region coding for butyrophilin (BT) is located at a telomeric position from the MHC class I region on human chromosome 6. In particular they described two genes Bt2 and Bt3, coding for a new group of co-stimulatory molecules (BT2.1, BT2.2, BT2.3, BT3.1, BT3.2 and BT3.3) belonging to the Ig superfamily (IgSF) (Linsley et al., 1992; Williams and Barclay, 1988), and related to B7 family by sequence similarity analysis: in particular, they show similarity with the Ig-V like extracellular domains of CD80 and CD86.

The BT3 family members appear in literature with different names: BT3.1 is also called BTF5 (Ruddy et al., 1997), or BTN3A1 (Rhodes et al., 2001), or more recently CD277 (Bensussan and Olive, 2005); BT3.2 is also called BTF4 (Ruddy et al., 1997), or BTN3A2; and, finally, BT3.3 appears also as BTF3 (Ruddy et al., 1997) or BTN3A3 (Rhodes et al., 2001). BT3 has two Ig-like extracellular domains that characterize the IgSF.

It has been proposed that B7 genes and MHC class I and II genes may have a common ancestral gene and encode for proteins involved in similar function, such as T cell activation (Rhodes et al., 2001). BT3 molecules have been found on immune cells, such as T, B and NK cells, monocytes and dendritic cells as well as hematopoietic precursors and some neoplastic cell lines. As for other co-stimulatory molecules, their structure is characterized by three domains: an extracellular domain to bind the ligand, a transmembrane domain and an intracellular domain termed B30.2 which is presumably involved in the regulation of intracellular superoxide concentrations. So far, the ligand(s) of CD277 is still unknown (reviewed in Gu et al., 2015).

To date, various therapeutic and vaccine strategies have been proposed that rely on a modulation of T cells; several immunomodulatory antibodies to CTLA-4, PD-1 and PD-L1 have already been approved for clinical use by multiple regulatory agencies throughout the world. Although these drugs represent major advances in cancer therapy, there still remain unmet medical needs for large parts of cancer patient populations that do not respond to the currently available treatments.

The patents WO 2012080351 A1, EP2651441A1, EP2946791A1, US20140322235, WO2012080769A1 refer to various antibodies against BTN3A able to activate or inhibit the cytolytic function, cytokine production and proliferation of Vγ9 Vδ2 T cells. However, these murine antibodies were not suitable for therapeutic application. Indeed, for administration to human patients, it is nowadays mandatory to humanize antibodies to avoid immunogenic reactions.

Humanization often requires modifying amino acids in the framework regions without certainty of maintaining the potency to the same level of the original murine antibodies.

This is especially true when modifying amino acids immediately adjacent to the CDR regions (see e.g. Queen patent U.S. Pat. No. 5,585,089).

Despite the difficulty, the inventors have now selected special humanized antibodies of the activating mAbs 7.2, which not only combine maintained functional properties of the mAbs 7.2 parental antibodies with predicted decreased immunogenicity for human, but also surprisingly exhibit superior developability properties, such as an improved yield in cell line production, a higher thermal stability as compared to parental murine antibody, and strong resistance to acid and heat stress. In addition, the humanized antibody mAb1 of the present disclosure advantageously bind to cynomolgus BTN3A and is well tolerated up to doses of 100 mg/kg/week in cynomolgus primate, thereby providing an excellent candidate for use as a drug in human therapies.

SUMMARY

The present disclosure thus relates to an isolated anti-BTN3A antibody comprising a variable heavy chain polypeptide VH of SEQ ID NO:1 and a variable light chain polypeptide VL of SEQ ID NO:2 or SEQ ID NO: 3. Such antibodies are humanized antibodies, in particular with predicted decreased immunogenicity with respect to their parental murine antibody. Such isolated anti-BTN3A antibody binds to human BTN3A. In particular, it binds to human BTN3A with a $K_D$ of 10 nM or less, preferably with a $K_D$ of 5 nM or less as measured by surface plasmon resonance.

In specific embodiments, said antibody according to the present disclosure, induces the activation of γδ-T cells, typically Vγ9Vδ2 T cells, in co-culture with BTN3 expressing cells, with an $EC_{50}$ below 5 μg/ml, preferably of 1 μg/ml or below, as measured in a degranulation assay. Consequently, said antibody induces the killing of tumor target cells independently of their tissues origin.

In specific embodiments, said isolated anti-BTN3A antibody comprises a mutant or chemically modified IgG1 constant region, wherein said mutant or chemically modified IgG1 constant region confers no or decreased binding to Fcγ receptors when compared to a corresponding antibody with wild type IgG1 isotype constant region. Typically, said mutant IgG1 constant region is IgG1 triple mutant L247F L248E and P350S. Examples of said isolated anti-BTN3A antibody are mAb1 comprising a heavy chain of SEQ ID NO:4 and a light chain of SEQ ID NO:6, or mAb2 comprising a heavy chain of SEQ ID NO:4 and a light chain of SEQ ID NO:7.

In other embodiments, said isolated anti-BTN3A antibody of the present disclosure is a monovalent format antibody, preferably selected from Fab or scFv antibodies.

The isolated anti-BTN3A antibody of the present disclosure may be used (i) as a therapeutic or (ii) as a diagnostic. For example, they are useful in the treatment of a cancer, for example a hematologic cancer, and more specifically a lymphoma or leukaemia. In other embodiments, they can also be used in the treatment of solid tumors, and more specifically prostate, ovarian or endometrial cancers. Alternatively, they may be used in the treatment of infectious disorders.

The disclosure further relates to a pharmaceutical composition comprising an anti-BTN3A antibody as described above, in combination with one or more of a pharmaceutically acceptable excipient, diluent or carrier, optionally comprising other active ingredients.

Another aspect of the present disclosure concerns a lyophilisate formulation, a pre-filled syringe or a vial comprising an anti-BTN3A antibody as described above.

The disclosure further relates to an expression vector for the recombinant production of an anti-BTN3A antibody as described above in a host cell, typically a mammalian host cell, such as CHO host cell, comprising at least one nucleic acid encoding said anti-BTN3A antibody. An embodiment of such expression vector comprises at least the nucleic acids encoding the heavy and light chains of mAb1 as disclosed herein. The host cell comprising such expression vectors are also described herein.

It is also disclosed herein a process for the production of an anti-BTN3A antibody of the present disclosure, comprising: (i) culturing the host cell as defined above for expression of said antibody by the host cell; optionally (ii) purifying said antibody; (iii) recovering the antibody.

The disclosure further relates to multispecific antibodies, such as bispecific antibodies, comprising at least one arm comprising a Fab or scFv including the VH and VL of the anti-BTN3A antibodies as defined above.

DETAILED DESCRIPTION

Definitions

In order that the present disclosure may be more readily understood, certain terms are first defined. Additional definitions are set forth throughout the detailed description.

As used herein, the term "BTN3A" has its general meaning in the art. In specific embodiments, it refers to human BTN3A polypeptides including either BTN3A1 of SEQ ID NO:18, BTN3A2 of SEQ ID NO:19 or BTN3A3 of SEQ ID NO:20.

The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies.

In natural antibodies of rodents and primates, two heavy chains are linked to each other by disulfide bonds, and each heavy chain is linked to a light chain by a disulfide bond. There are two types of light chains, lambda (λ) and kappa (κ). There are five main heavy chain classes (or isotypes) which determine the functional activity of an antibody molecule: IgM, IgD, IgG, IgA and IgE. Each chain contains distinct sequence domains. In typical IgG antibodies, the light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR).

The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) can participate in the antibody binding site, or influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, typically includes six CDRs, comprising the CDRs set from each of a heavy and a light chain V region. Framework Regions (FRs) refer to amino acid sequences interposed between CDRs. Accordingly, the variable regions of the light and heavy chains typically comprise 4 framework regions and 3 CDRs of the following sequence: FR1-CDR1-FR2-CDR2-FR3-CDR3-FR4.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (Kabat et al., 1992, hereafter "Kabat et al."). This numbering system is used in the present specification. The Kabat residue designations do not always correspond directly with the linear numbering of the amino acid residues in SEQ ID sequences. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. The CDRs of the heavy chain variable domain are located at residues 31-35 (H-CDR1), residues 50-65 (H-CDR2) and residues 95-102 (H-CDR3) according to the Kabat numbering system. The CDRs of the light chain variable domain are located at residues 24-34 (L-CDR1), residues 50-56 (L-CDR2) and residues 89-97 (L-CDR3) according to the Kabat numbering system.

In specific embodiments, an antibody provided herein is an antibody fragment, and more particularly any protein including an antigen-binding domain of an antibody as disclosed herein. Antibody fragments include, but are not limited to, Fv, Fab, F(ab')2, Fab', dsFv, scFv, sc(Fv)2 and diabodies.

As used herein, the term "specificity" refers to the ability of an antibody to detectably bind an epitope presented on an antigen, such as a BTN3A. In some embodiments, it is intended to refer to an antibody that binds to human BTN3A as expressed on peripheral blood marrow cells (PBMCs), preferably with an $EC_{50}$ below 50 µg/ml and more preferably below 10 µg/ml as determined in the Examples (see Table 4). In other embodiments, it binds to an antigen recombinant polypeptide with a $K_D$ of 100 nM or less, 10 nM or less, 1 nM or less, 100 pM or less, or 10 pM or less, as measured by SPR measurements as determined in the Examples (see Table 4).

An antibody that "cross-reacts with an antigen other than BTN3A" is intended to refer to an antibody that binds that antigen other than BTN3A with a $K_D$ of 10 nM or less, 1 nM or less, or 100 pM or less. An antibody that "does not cross-react with a particular antigen" is intended to refer to an antibody that binds to that antigen, with a $K_D$ of 100 nM or greater, or a $K_D$ of 1 µM or greater, or a $K_D$ of 10 µM or greater. In certain embodiments, such antibodies that do not cross-react with the antigen exhibit essentially undetectable binding against these proteins in standard binding assays. In specific embodiment, the humanized antibody of the present disclosure, e.g., mAb1, cross-reacts with cynomolgus BTN3A1, BTN3A2 and BTN3A3 of SEQ ID NO:21, SEQ ID NO:22 and SEQ ID NO:23 respectively for example as measured in Biacore assay (see Table 21).

An "isolated antibody", as used herein, refers to an antibody that is substantially free of other antibodies having different antigenic specificities (e.g., an isolated antibody that specifically binds to BTN3A is substantially free of antibodies that specifically bind to other antigens than BTN3A). An isolated antibody that specifically binds to BTN3A may, however, have cross-reactivity to other antigens, such as related BTN3A molecules from other species. Moreover, an isolated antibody may be substantially free of other cellular material and/or chemicals.

The term "monoclonal antibody" or "monoclonal antibody composition" as used herein refers to a preparation of antibody molecules of single molecular composition. A monoclonal antibody composition displays a single binding specificity and affinity for a particular epitope.

The phrases "an antibody recognizing an antigen" and "an antibody having specificity for an antigen" are used interchangeably herein with the term "an antibody which binds specifically to an antigen".

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction.

The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system.

Specificity can further be exhibited by, e.g., an about 10:1, about 20:1, about 50:1, about 100:1, 10.000:1 or greater ratio of affinity/avidity in binding to the specific antigen versus nonspecific binding to other irrelevant molecules (in this case the specific antigen is a BTN3A polypeptide). The term "affinity", as used herein, means the strength of the binding of an antibody to an epitope.

As used herein, the term "Avidity" refers to an informative measure of the overall stability or strength of the antibody-antigen complex. It is controlled by three major factors: antibody epitope affinity; the valence of both the antigen and antibody; and the structural arrangement of the interacting parts. Ultimately these factors define the specificity of the antibody, that is, the likelihood that the particular antibody is binding to a precise antigen epitope.

As used herein, the term "activating antibody" refers to an antibody able to directly or indirectly induce immune functions of effector cells. In particular, as used herein, an activating anti-BTN3A antibody has at least the capacity to induce the activation of γδ T cells, typically Vγ9Vδ2 T cells, in co-culture with BTN3 expressing cells, with an $EC_{50}$ below 5 µg/ml, preferably of 1 µg/ml or below, as measured in a degranulation assay as described in the Examples below.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

As used herein, the term, "optimized" means that a nucleotide sequence has been altered to encode an amino acid sequence using codons that are preferred in the production cell or organism, generally a eukaryotic cell, for example, a Chinese Hamster Ovary cell (CHO) or a human cell. The optimized nucleotide sequence is engineered to retain completely or as much as possible the amino acid sequence originally encoded by the starting nucleotide sequence. The amino acid sequences encoded by optimized nucleotide sequences are also referred to as optimized.

As used herein, the percent identity between the two sequences is a function of the number of identical positions shared by the sequences (i.e., % identity=number of identical positions/total number of positions×100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two amino acid sequences can be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. Alternatively, the percent identity between two amino acid sequences can be determined using the Needleman and Wunsch (J. Mol, Biol. 48:444-453, 1970) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6.

The percent identity between two nucleotide amino acid sequences may also be determined using for example algorithms such as the BLASTN program for nucleic acid sequences using as defaults a word length (W) of 11, an expectation (E) of 10, M=5, N=4, and a comparison of both strands.

Recombinant Humanized Anti-BTN3A Activating Antibodies

Antibodies of the disclosure include the selected humanized recombinant antibodies mAb1, mAb2, mAb4 and mAb5, which are structurally characterized by their variable heavy and light chain amino acid sequences and human constant regions (isotypes) as described in the Table 1 below:

TABLE 1

Variable heavy and light chain amino acid sequences of mAb1-mAb6

| Antibody | VH Amino acid sequence | VL Amino acid sequence | Isotype constant region |
|---|---|---|---|
| mAb1 | SEQ ID NO: 1 (VH2 7.2) | SEQ ID NO: 2 (Vk1 7.2) | Silent IgG1 L247F/L248E/P350S |
| mAb2 | SEQ ID NO: 1 (VH2 7.2) | SEQ ID NO: 3 (Vk2 7.2) | Silent IgG1 L247F/L248E/P350S |
| mAb3 | Humanized variant from 20.1 | Humanized variant from 20.1 | Silent IgG1 L247F/L248E/P350S |
| mAb4 | SEQ ID NO: 1 (VH2 7.2) | SEQ ID NO: 2 (Vk1 7.2) | IgG4 S241P/L248E |
| mAb5 | SEQ ID NO: 1 (VH2 7.2) | SEQ ID NO: 3 (Vk2 7.2) | IgG4 S241P/L248E |
| mAb6 | Same as mAb3 | Same as mAb3 | IgG4 S241P/L248E | mAb3 and mAb6 are humanized antibodies of another parental murine anti-BTN3A antibody, referred as mAb 20.1 and described in WO2012/080351, for use as comparative examples.

The corresponding amino acid and nucleotide coding sequence of the constant isotype regions of IgG1, IgG4 and their mutant versions IgG1 L247F/L248E/P350S and IgG4 S241P/L248E used for generating mAb1 to mAb6 are well-known in the art (Oganesyan et al., 2008; Reddy et al., 2000). The C-terminal lysine found in IgG may be naturally cleaved off and this modification does not affect the properties of the antibody; so, this residue may additionally be deleted in the constructs of mAb1 to mAb6.

Full length light and heavy chains and corresponding coding sequences of mAb1, mAb2, mAb4 and mAb 5 are shown in the Table 2 below.

TABLE 2

Full length heavy and light chain DNA coding sequences

| Antibody | Amino acid sequence | DNA coding sequence |
|---|---|---|
| mAb1 | Heavy Chain: SEQ ID NO: 4 | Heavy Chain: SEQ ID NO: 8 |
|  | Light Chain: SEQ ID NO: 6 | Light Chain: SEQ ID NO: 10 |
| mAb2 | Heavy Chain: SEQ ID NO: 4 | Heavy Chain: SEQ ID NO: 8 |
|  | Light Chain: SEQ ID NO: 7 | Light Chain: SEQ ID NO: 11 |
| mAb4 | Heavy Chain: SEQ ID NO: 5 | Heavy Chain: SEQ ID NO: 9 |
|  | Light Chain: SEQ ID NO: 6 | Light Chain: SEQ ID NO: 10 |
| mAb5 | Heavy Chain: SEQ ID NO: 5 | Heavy Chain: SEQ ID NO: 9 |
|  | Light Chain: SEQ ID NO: 7 | Light Chain: SEQ ID NO: 11 |

Examples of the amino acid sequences of the VH CDR1s (also called HCDR1), VH CDR2s (also called HCDR2), VH CDR3s (also called HCDR1), VL CDR1s (also called LCDR1), VL CDR2s (also called LCDR2), VL CDR3s (also called HCDR3) of some antibodies according to the disclosure are shown in Table 3.

In Table 3, the CDR regions of the antibodies of the present disclosure are delineated using the Kabat numbering (Kabat et al., 1992, hereafter "Kabat et al.").

For the ease of reading, the CDR regions are called hereafter HCDR1, HCDR2, HCDR3, LCDR1, LCDR2, LCDR3 respectively.

TABLE 3

CDR regions of mAb1, mAb2, mAb4 and mAb5 and parental murine mAbs 7.2 antibody according to Kabat numbering

| Original antibody | HCDR1 | HCDR2 | HCDR3 | LCDR1 | LCDR2 | LCDR3 |
|---|---|---|---|---|---|---|
| mAb 7.2 | SEQ ID NO: 12 | SEQ ID NO: 13 | SEQ ID NO: 14 | SEQ ID NO: 15 | SEQ ID NO: 16 | SEQ ID NO: 17 |
| mAb1 | | | | | | |
| mAb2 | | | | | | |
| mAb4 | | | | | | |
| mAb5 | | | | | | |

In a specific embodiment, said recombinant anti-BTN3A antibody as defined above have one or more of the following properties:
(i) it binds to BTN3A with a $K_D$ of 10 nM or less, preferably with a $K_D$ of 1 nM or less, as measured by SPR, for example as described in the Examples below;
(ii) it cross-reacts to cynomolgus BTN3A with a $K_D$ of 100 nM or less, preferably with a $K_D$ of 10 nM or less, as measured by SPR, for example as described in the Examples below;
(iii) it binds to human PBMCs with an $EC_{50}$ of 50 μg/ml or below, preferably of 10 μg/ml or below, as measured in a flow cytometry assay as described in the Examples below;
(iv) it induces the activation of)43-T cells, typically Vγ9Vδ2 T cells, in co-culture with BTN3 expressing cells, with an $EC_{50}$ below 5 μg/ml, preferably of 1 μg/ml or below, as measured in a degranulation assay as described in the Examples below.

In certain embodiments that may be combined with the previous embodiments, an antibody provided herein is an antibody fragment of the above-defined antibodies.

Antibody fragments include, but are not limited to, Fab, Fab', Fab'-SH, F(ab')2, Fv, Unibody, and scFv fragments, diabodies, single domain or nanobodies and other fragments.

Preferably, it is a monovalent antibody, such as a Fab of scFv fragments.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells as described herein.

The antibody of the present disclosure is a humanized antibody. Typically, a non-human antibody is humanized to reduce immunogenicity to humans, while having at least the same affinity (or superior affinity) of the parental non-human antibody. In preferred embodiments, the antibodies of the present disclosure are humanized antibodies of the parent antibody mAb 7.2 as disclosed in WO2012/080351. Comparative examples include humanized antibodies of the parent antibody mAb 20.1 as disclosed in WO2012/080351.

Generally, a humanized antibody comprises one or more variable domains in which, CDRs, (or portions thereof) are derived from a non-human antibody, e.g. the murine mAbs 7.2, and FRs (or portions thereof) are derived from the murine antibody sequences with mutations to reduce immunogenicity. A humanized antibody optionally will also comprise at least a portion of a human constant region.

Preferably, the recombinant antibody according to the disclosure is a humanized silent antibody, typically a humanized silent IgG1 or IgG4 antibody.

As used herein, the term "silent" antibody refers to an antibody that exhibits no or low FcγR binding and/or C1q binding as measured in binding assays such as those described in the Examples.

In one embodiment, the term "no or low FcγR and/or C1q binding" means that the silent antibody exhibit an FcγR and/or C1 q binding that is at least below 50%, for example below 80% of the FcγR and/or C1q binding that is observed with the corresponding antibody with wild type human IgG1 or IgG4 isotype.

Framework or Fc Engineering

The antibodies of the disclosure include modifications made to framework residues within VH and VL, to decrease the immunogenicity of the antibody as compared to the corresponding murine antibodies mAb 7.2.

In one specific embodiment, the antibody of the disclosure is a humanized monoclonal antibody of the parent murine antibody mAb 7.2, including at least the following amino acid mutations in the VH framework regions: V5Q; V11L; K12V; R66K; S74F; I75S; E81Q; S82AR; R82BS; R83T; D85E; T87S; L108S; and at least the following amino acid mutations in the VK framework regions: T5N; V15L; R18T; V19I; K42N; A43I; D70G; F73L; Q100G.

In another specific embodiment, the antibody of the disclosure is a humanized monoclonal antibody of the parent murine antibody mAb 7.2, including at least the following amino acid mutations in the VH framework regions as compared to mAb 7.2: V5Q; V11L; K12V; R66K; S74F; I75S; E81Q; S82AR; R82BS; R83T; D85E; T87S; L108S; and at least the following amino acid mutations in the VK framework regions: T5N; V15L; R18T; V19I; K42N; A43I; S63T; D70G; F73L; Q100G.

In addition to modifications made within the framework regions, the antibodies of the disclosure may be engineered to include modifications within the Fc region, typically to alter one or more functional properties of the antibody, such as serum half-life, complement fixation, Fc receptor binding, and/or antigen-dependent cellular cytotoxicity.

Furthermore, an antibody of the disclosure may be chemically modified (e.g., one or more chemical moieties can be attached to the antibody) or be modified to alter its glycosylation, again to alter one or more functional properties of the antibody. Each of these embodiments is described in further detail below.

As used herein, the term "isotype constant region" or "Fc region" is used interchangeably to define the C-terminal region of an immunoglobulin heavy chain, including native sequence Fc region and variant Fc regions. The human IgG heavy chain Fc region is generally defined as comprising the amino acid residue from position C226 or from P230 to the carboxyl-terminus of the IgG antibody wherein the numbering is according to the EU numbering system. The C-terminal lysine (residue K447) of the Fc region may be removed, for example, during production or purification of the antibody or its corresponding codon deleted in the recombinant constructs. Accordingly, a composition of antibodies of the disclosure may comprise antibody populations with all K447 residues removed, antibody populations with no K447 residues removed, and antibody populations having a mixture of antibodies with and without the K447 residue.

In one specific embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In other embodiments, the Fc region is modified to decrease the ability of the antibody to mediate antibody dependent cellular cytotoxicity (ADCC) and/or to decrease the affinity of the antibody for an Fcγ receptor by modifying one or more amino acids. Such antibodies with decreased effector functions, and in particular decreased ADCC include silent antibodies.

In certain embodiments, the Fc domain of the IgG1 isotype is used. In some specific embodiments, a mutant variant of the IgG1 Fc fragment is used, e.g. a silent IgG1 Fc which reduces or eliminates the ability of the fusion polypeptide to mediate antibody dependent cellular cytotoxicity (ADCC) and/or to bind to an Fcγ receptor.

In certain embodiments, the Fc domain of the IgG4 isotype is used. In some specific embodiments, a mutant variant of the IgG4 Fc fragment is used, e.g. a silent IgG4 Fc which reduces or eliminates the ability of the fusion polypeptide to mediate antibody dependent cellular cytotoxicity (ADCC) and/or to bind to an Fcγ receptor.

Silenced effector functions can be obtained by mutation in the Fc constant part of the antibodies and have been described in the Art (Baudino et al., 2008; Strohl, 2009). Examples of silent IgG1 antibodies comprise the triple mutant variant IgG1 L247F L248E. P350S. Examples of silent IgG4 antibodies comprise the double mutant variant IgG4 S241P L248E.

In certain embodiments, the Fc domain is a silent Fc mutant preventing glycosylation at position 314 of the Fc domain. For example, the Fc domain contains an amino acid substitution of asparagine at position 314. An example of such amino acid substitution is the replacement of N314 by a glycine or an alanine.

In still another embodiment, the glycosylation of an antibody is modified. For example, an aglycoslated antibody can be made (i.e., the antibody lacks glycosylation). Glycosylation can be altered to, for example, increase the affinity of the antibody for the antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Another modification of the antibodies herein that is contemplated by the present disclosure is pegylation or hesylation or related technologies. An antibody can be pegylated to, for example, increase the biological (e.g., serum) half-life of the antibody. To pegylate an antibody, the antibody, or fragment thereof, typically is reacting with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy-or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See for example, EP 0 154 316 by Nishimura et al. and EP 0 401 384 by Ishikawa et al.

Another possibility is a fusion of at least the antigen-binding region of the antibody of the disclosure to proteins capable of binding to serum proteins, such human serum albumin to increase half-life of the resulting molecule. Such approach is for example described in Nygren et al., EP 0 486 525.

In certain embodiments, the C-terminal lysine commonly present on human IgG heavy chain constant domains, is engineered out to reduce heterogeneity due to the cleavage of this reduce commonly observed during manufacturing or storage. Such modifications do not perceptible change the desirable functions of these antibodies, while conferring the benefit of stability to these molecules.

Nucleic Acid Molecules Encoding Antibodies of the Disclosure

Also disclosed herein are the nucleic acid molecules that encode the anti-BTN3A antibodies of the present disclosure. Examples of variable light chain and heavy chain nucleotide sequences are those encoding the variable light chain and heavy chain amino acid sequences of any one of mAb1, mAb2, mAb4 and mAb5, the latter sequences being easily derived from the Table 1 and Table 2, and using the genetic code and, optionally taking into account the codon bias depending on the host cell species.

The present disclosure also pertains to nucleic acid molecules that derive from the latter sequences having been optimized for protein expression in mammalian cells, for example, CHO cell lines.

The nucleic acids may be present in whole cells, in a cell lysate, or may be nucleic acids in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art (Ausubel et al., 1988). A nucleic acid of the disclosure can be, for example, DNA or RNA and may or may not contain intronic sequences. In an embodiment, the nucleic acid may be present in a vector such as a phage display vector, or in a recombinant plasmid vector.

Nucleic acids of the disclosure can be obtained using standard molecular biology techniques. Once DNA fragments encoding, for example, VH and VL segments are obtained, these DNA fragments can be further manipulated by standard recombinant DNA techniques, for example to convert the variable region genes to full-length antibody chain genes, to Fab fragment genes or to an scFv gene. In these manipulations, a VL- or VH-encoding DNA fragment (for example VL and VH as defined in Table 1) is operatively linked to another DNA molecule, or to a fragment encoding another protein, such as an antibody constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (Kabat et al., 1992) and DNA fragments encompassing these regions can be obtained by standard PCR amplification. The heavy chain constant region can be an IgG1, IgG2, IgG3, IgG4, IgA, IgE, IgM or IgD constant region. In some embodiments, the heavy chain constant region is selected among IgG1 isotypes, for example human IgG1 isotype. In other embodiments, the heavy chain constant region is selected among IgG4 isotypes, for example human IgG4 isotype. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as to a Fab light chain gene) by operatively linking the VL-encoding DNA to another DNA molecule encoding the light chain constant region, CL. The sequences of human light chain constant region genes are known in the art (Kabat et al., 1992) and DNA fragments encompassing these regions can be obtained by standard PCR amplification. The light chain constant region can be a kappa or a lambda constant region.

To create an scFv gene, the VH- and VL-encoding DNA fragments are operatively linked to another fragment encoding a flexible linker, e.g., encoding the amino acid sequence (Gly4-Ser)$_3$, such that the VH and VL sequences can be expressed as a contiguous single-chain protein, with the VL and VH regions joined by the flexible linker (Bird et al., 1988; Huston et al., 1988; McCafferty et al., 1990).

Generation of Transfectomas Producing Monoclonal Antibodies

Antibodies of the present disclosure can be produced in a host cell transfectoma using, for example, a combination of recombinant DNA techniques and gene transfection methods as is well known in the art (Morrison, 1985).

For example, to express the antibodies, or antibody fragments thereof, DNAs encoding partial or full-length light and heavy chains can be obtained by standard molecular biology or biochemistry techniques (e.g., DNA chemical synthesis, PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors disclosed herein carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel's publication (Goeddel, 1990). It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g., the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukemia virus type 1 (Takebe et al., 1988).

In addition to the antibody chain genes and regulatory sequences, the recombinant expression vectors of the present disclosure may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is theoretically possible to express the antibodies of the present disclosure in either prokaryotic or eukaryotic host cells. Expression of antibodies in eukaryotic cells, for example mammalian host cells, yeast or filamentous fungi, is discussed because such eukaryotic cells, and in particular mammalian cells, are more likely than prokaryotic cells to assemble and secrete a properly folded and immunologically active antibody.

In one specific embodiment, a cloning or expression vector according to the disclosure comprises one of the coding sequences of the heavy and light chains of any one of mAb1, mAb2, mAb4 and mAb5 operatively linked to suitable promoter sequences.

Mammalian host cells for expressing the recombinant antibodies of the disclosure include Chinese Hamster Ovary (CHO cells) including dhfr-CHO cells (described in Urlaub and Chasin, 1980) used with a DHFR selectable marker(as described inKaufman and Sharp, 1982), CHOK1 dhfr+ cell lines, NSO myeloma cells, COS cells and SP2 cells, for example GS CHO cell lines together with GS XceedT M gene expression system (Lonza). When recombinant expression vectors encoding antibody genes are introduced into mammalian host cells, the antibodies are produced by culturing the host cells for a period of time sufficient for expression of the antibody in the host cells and, optionally, secretion of the antibody into the culture medium in which the host cells are grown. Antibodies can be recovered and purified for example from the culture medium after their secretion using standard protein purification methods (Shukla et al., 2007).

In one specific embodiment, the host cell of the disclosure is a host cell transfected with an expression vector having the coding sequences suitable for the expression of mAb1, mAb2, mAb4 and mAb5 respectively, operatively linked to suitable promoter sequences.

For example, the present disclosure relates to a host cell comprising at least the nucleic acids of SEQ ID NO:8 and 10 encoding respectively the heavy and light chains of mAb1.

The latter host cells may then be further cultured under suitable conditions for the expression and production of an antibody of the disclosure selected from the group consisting of mAb1, mAb2, mAb4 and mAb5 respectively.

Alternatively, cell free expression systems may be used for the production of any of mAb1, mAb2, mAb4 and mAb5. Typically, methods of cell-free expression of proteins or antibodies are already described (Stech et al., 2017).

Immunoconjugates

In another aspect, the present disclosure features an anti-BTN3A antibody as disclosed herein, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxon, cytochalasin B, gramicidin D, ethidium bromide, emetine, mitomycin, etoposide, tenoposide, vincristine, vinblastine, t. colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), ablating agents (e.g., mechlorethamine, thioepa chloraxnbucil, meiphalan, carmustine (BSNU) and lomustine (CCNU), cyclothosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), monomethyl auristatin E and anti-mitotic agents (e.g., vincristine and vinblastine).

Cytotoxins can be conjugated to antibodies of the present disclosure using linker technology available in the art. Examples of linker types that have been used to conjugate a cytotoxin to an antibody include, but are not limited to, hydrazones, thioethers, esters, disulfides and peptide-containing linkers, such as valine-citruline linker. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Panowski et al., 2013 for a review on antibody drug conjugates.

Antibodies of the present disclosure also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$, and lutetium$^{177}$. Method for preparing radioimmunconjugates are established in the art.

Bispecific or Multispecific Molecules

In another aspect, it is further disclosed herein bispecific or multispecific molecules comprising an anti-BTN3A antibody of the present disclosure. An antibody can be derivatized or linked to another functional molecule, e.g., another peptide or protein (e.g., another antibody or ligand for a receptor) to generate a bispecific molecule that binds to at least two different binding sites or target molecules. The antibody may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present disclosure includes bispecific molecules comprising at least one first binding specificity for BTN3A, for example, one antigen-binding portion of any one of mAb1, mAb2, mAb4 and mAb5 and a second binding specificity for a second target epitope.

Additionally, for the embodiment in which the bispecific molecule is multi-specific, the molecule can further include a third binding specificity, in addition to the first and second target epitope.

In one embodiment, the bispecific molecules as disclosed herein comprise as a binding specificity at least one antibody, or an antibody fragment thereof, including, e.g., an Fab, Fab', F(ab')2, Fv, Unibody or a single chain Fv. The antibody may also be a light chain or heavy chain dimer, or any minimal fragment thereof such as a Fv or a single chain construct as described in Ladner et al. U.S. Pat. No. 4,946,778.

Other antibodies which can be employed in the bispecific molecules disclosed herein are murine, chimeric and humanized monoclonal antibodies.

The bispecific molecules of the present disclosure can be prepared by conjugating the constituent binding specificities, using methods known in the art. For example, each binding-specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (Karpovsky et al., 1984; Liu et al., 1985). Other methods include those described in Brennan et al., 1985; Glennie et al., 1987; Paulus, 1985.

Alternatively, both binding specificities can be encoded in the same vector and expressed and assembled in the same host cell. This method is particularly useful where the bispecific molecule is a mAb×mAb, mAb×Fab, Fab×F(ab')2 or ligand x Fab fusion protein. A bispecific molecule of the disclosure can be a single chain molecule comprising one single chain antibody and a binding determinant, or a single chain bispecific molecule comprising two binding determinants.

Binding of the bispecific molecules to their specific targets can be confirmed by, for example, enzyme-linked immunosorbent assay (ELISA), radioimmunoassay (REA), FACS analysis, bioassay (e.g., growth inhibition and apoptosis), or Western Blot assay. Each of these assays generally detects the presence of protein-antibody complexes of particular interest by employing a labeled reagent (e.g., an antibody) specific for the complex of interest.

The antibodies of the present disclosure may also be used to prepare artificial T cell receptor (also known as chimeric T cell receptors, or chimeric antigen receptors (CARs)).

For example, the variable regions of antibodies may be used to form a Fab or scFv which is linked via a spacer to a transmembrane domain (typically the transmembrane domain of CD8 alpha) and a signaling endodomain of a TCR (for example CD3 zeta), and optionally, a costimulatory signaling domain (for example from 4-1BB or CD28) and may be produced at the surface of T cells. Such CARs may be used in adoptive transfer therapy, for example for treating proliferative disorders.

Pharmaceutical Compositions

In another aspect, the present disclosure provides a composition, e.g., a pharmaceutical composition, containing one or a combination of antibodies disclosed herein, for example, one antibody selected from the group consisting of mAb1, mAb2, mAb4 and mAb5 or their antigen-binding portions, formulated together with a pharmaceutically acceptable carrier. Such compositions may include one or a combination of (e.g., two or more different) antibodies, or immunoconjugates or bispecific molecules as described above.

Pharmaceutical compositions disclosed herein also can be administered in combination therapy, i.e., combined with other agents. For example, the combination therapy can include an anti-BTN3A antibody of the present disclosure, for example one antibody selected from the group consisting of mAb1, mAb2, mAb4 and mAb5 or their antigen-binding portions, combined with at least one anti-viral, anti-inflammatory or another anti-proliferative agent. Examples of therapeutic agents that can be used in combination therapy are described in greater detail below in the section on uses of the antibodies of the disclosure.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g., by injection or infusion). In one embodiment, the carrier should be suitable for subcutaneous route or intratumoral injection. Depending on the route of administration, the active compound, i.e., antibody, immunoconjugate, or bispecific molecule, may be coated in a material to protect the compound from the action of acids and other natural conditions that may inactivate the compound.

Sterile phosphate-buffered saline is one example of a pharmaceutically acceptable carrier. Other suitable carriers are well-known to those in the art. (Remington and Gennaro, 1995) Formulations may further include one or more excipients, preservatives, solubilizers, buffering agents, albumin to prevent protein loss on vial surfaces, etc.

The form of the pharmaceutical compositions, the route of administration, the dosage and the regimen naturally depend upon the condition to be treated, the severity of the illness, the age, weight, and sex of the patient, etc.

The pharmaceutical compositions of the disclosure can be formulated for a topical, oral, parenteral, intranasal, intravenous, intramuscular, subcutaneous or intraocular administration and the like.

Preferably, the pharmaceutical compositions contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders or lyophilisates for the extemporaneous preparation of sterile injectable solutions or dispersions. In all cases, the form must be sterile and must be fluid to the extent that easy syringeability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antibody of the disclosure can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies of the disclosure may be formulated within a therapeutic mixture to comprise about 0.0001 to 1.0 milligrams, or about 0.001 to 0.1 milligrams, or about 0.1 to 1.0 or even 1.0 to about 10 milligrams per dose. Multiple doses can also be administered.

Suitable formulation for solution for infusion or subcutaneous injection of antibodies have been described in the art and for example are reviewed in Cui et al (Drug Dev Ind Pharm 2017, 43(4): 519-530) In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 µm) are generally designed using polymers able to be degraded in vivo.

Biodegradable polyalkyl-cyanoacrylate nanoparticles that meet these requirements are contemplated for use in the present disclosure, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

Uses and Methods of the Antibodies of the Disclosure

The antibodies of the present disclosure have in vitro and in vivo diagnostic and therapeutic utilities. For example, these molecules can be administered to cells in culture, e.g. in vitro, ex vivo or in vivo, or in a subject, e.g., in vivo, to treat, prevent or diagnose a variety of disorders.

As used herein, the term "treat" "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease. In particular, with reference to the treatment of a tumor, the term "treatment" may refer to the inhibition of the growth of the tumor, or the reduction of the size of the tumor.

The antibodies of the disclosure are anti-BTN3A activating antibodies and can activate the cytolytic function, cytokine production and/or proliferation of Vγ9 V62 T cells, and thereby may be used to overcome the immunosuppressive mechanisms observed in cancer patients, and during chronic infections.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

Examples of cancers include, but are not limited to, hematological malignancies such as B-cell lymphoid neoplasm, T-cell lymphoid neoplasm, non-Hodgkin lymphoma (NHL), B-NHL, T-NHL, chronic lymphocytic leukemia (CLL), small lymphocytic lymphoma (SLL), mantle cell lymphoma (MCL), NK-cell lymphoid neoplasm and myeloid cell lineage neoplasm including acute myeloid leukemia.

Examples of non-hematological cancers include, but are not limited to, colon cancer, breast cancer, lung cancer, brain cancer, prostate cancer, head and neck cancer, pancreatic cancer, bladder cancer, colorectal cancer, bone cancer, cervical cancer, ovarian cancer, liver cancer, oral cancer, esophageal cancer, thyroid cancer, kidney cancer, stomach cancer, testicular cancer and skin cancer.

Examples of chronic infections include, but are not limited to, viral, bacterial, parasitic or fungal infections such as chronic hepatitis, lung infections, lower respiratory tract infections, bronchitis, influenza, *pneumoniae* and sexually transmitted diseases.

Examples of viral infections include, but are not limited to, hepatitis (HAV, HBV, HCV), herpes simplex (HSV), herpes zoster, HPV, influenza (Flu), AIDS and AIDS related complex, chickenpox (varicella), common cold, cytomegalovirus (CMV) infection, smallpox (variola), Colorado tick fever, dengue fever, ebola hemorrhagic fever, foot and mouth disease, lassa fever, measles, marburg hemorrhagic fever, infectious mononucleosis, mumps, norovirus, poliomyelitis, progressive multifocal leukencephalopathy (PML), rabies, rubella, SARS, viral encephalitis, viral gastroenteritis, viral meningitis, viral pneumonia, West Nile disease and yellow fever. Examples of bacterial infections include, but are not limited to, pneumonia, bacterial meningitis, cholera, diphtheria, tuberculosis, anthrax, botulism, brucellosis, campylobacteriosis, typhus, gonorrhea, listeriosis, lyme disease, rheumatic fever, pertussis (Whooping Cough), plague, *salmonellosis*, scarlet fever, shigellosis, syphilis, tetanus, trachoma, tularemia, typhoid fever, and urinary tract infections. Examples also include bacterial infections caused by *Coxiella burnetii, Brucella abortus, Tropheryma whipplei, Mycobacterium tuberculosis* and *Mycobacterium* canettii.

Examples of parasitic infections include, but are not limited to, malaria, leishmaniasis, trypanosomiasis, chagas disease, cryptosporidiosis, fascioliasis, filariasis, amebic infections, giardiasis, pinworm infection, schistosomiasis, taeniasis, toxoplasmosis, trichinellosis, and trypanosomiasis. Examples of fungal infections include include, but are not limited to, candidiasis, aspergillosis, coccidioidomycosis, cryptococcosis, histoplasmosis and tinea pedis.

Accordingly, the disclosure relates to a method for treating one of the disorders disclosed above, in a subject in need thereof, said method comprising administering to said subject a therapeutically efficient amount of an anti-BTN3A antibodies as disclosed above, typically, one of mAb1, mAb2, mAb4 or mAb5.

In certain embodiments, said subject has been selected among patient having BTN3A expressing tumors.

The antibodies for use as disclosed above may be administered as the sole active ingredient or in conjunction with, e.g. as an adjuvant to or in combination to, other drugs e.g. cytokines, anti-viral, anti-inflammatory agents or cytotoxic, anti-proliferative, chemotherapy or anti-tumor agents, cell therapy product (e.g. γδ T cell composition) e.g. for the treatment or prevention of diseases mentioned above.

For example, the antibodies for use as disclosed above may be used in combination with cell therapy, in particular γδ T cell therapy, chemotherapy, antineoplastic agents, or immunotherapeutic agents.

As used herein, the term "cell therapy" refers to a therapy comprising the in vivo administration of at least a therapeutically efficient amount of a cell composition to a subject in need thereof. The cells administered to the patient may be allogenic or autologous. The term "γδ T cell therapy" refers to a cell therapy wherein the cell composition includes, as the active principle, γδ T cells, in particular Vγ9/Vδ2 T cells.

A cell therapy product refers to the cell composition which is administered to said patient for therapeutic purposes. Said cell therapy product include a therapeutically efficient dose of cells and optionally, additional excipients, adjuvants or other pharmaceutically acceptable carriers.

Suitable antineoplastic agents may include without limitation, alkylating agents (such as cyclophosphamide, mechloretamine, chlorambucil, melphalan, nitrosureas, temozolomide), anthracyclines (such as daunorubicin, doxorubicin, epirubicin, idarubicin, mitoxantrone, valrubicin), taxanes (such as Paclitaxel, Docetaxel), epothilones, inhibitors of Topoisomerase I (such as Irinotecan or Topotecan), inhibitors of Topoisomerase II (such as Etoposide, teniposide, or Tafluposide), nucleotide analogs and precursor analogs (such as azacitidine, azathioprine, capecitabine, cytarabine, flurouracil, gemcitabine, hydroxyurea, mercaptopurine, methotrexate, or Tioguanine), peptide antibiotics (such as carboplatin, cisplatin and oxaliplatin), retinoids (such as tretinoin, alitretinoin, bexarotene), *vinca* alkaloids and derivatives (such as vinblastine, vincristine, vindesine, vinorelbine), targeted therapies such as kinase inhibitors (such as Ibrutinib, Idelalisib, Erlotinib, Gefitinib, Imatinib, Vemurafenib, Vismodegib), proteasome inhibitors (such as bortezomib, carfilzomib), histone deacetylase inhibitors (such as Vorinostat or Romidepsin).

Examples of immunotherapeutic agents include without limitation phosphoantigens (e.g. zoledronic acid or other bisphosphonates), anti-PD-1 antibodies, anti-PD-L1 antibodies, anti-BTLA antibodies, anti-CTLA-4 antibodies and cytokines (such as interleukin 2 (IL-2) (Choudhry H et al, 2018, Biomed Res Int. 2018 May 6), interleukin 15 (IL-15) (Patidar M et al., Cytokine Growth Factor Rev. 2016 October;31:49-59), interleukin 21 (IL-21) (Caccamo N. et al., PLoS One. 2012; 7(7):e41940), or interleukin 33 (IL-33) (Duault C et al., J Immunol. 2016 Jan. 1; 196(1):493-502)), or their recombinant forms and their derivatives, or any cytokines capable of inducing lymphocyte activity (e.g. proliferation or cytokines production or metabolic changes). The term derivative is used for any cytokine modifications that can rely on PEGylation (e.g. conjugation to polyethylene glycol (PEG) chains), mutation such as amino acid deletion, substitution or insertion, or association with potentiating agents (for example IL15/IL15Ra complexes fused to an IgG1 Fc, in which IL-15 is additionally mutated (asn72asp) that further increase biological activity making this complex an IL-2 and IL-15Rh superagonist (Rhode PR et al, Cancer Immunol Res. 2016; 4(1):49-60)) (Barroso-Sousa Ret al, Curr Oncol Rep. 2018 Nov. 15; 21(1):1).

The term "IL-2" has its general meaning and refers to the human interleukin-2. IL-2 is part of the body's natural immune response. IL-2 mainly regulates lymphocyte activity by binding to IL-2 receptors.

The term "IL-15" has its general meaning and refers to the human interleukin-15. Like IL-2, IL-15 binds to and signals through a complex composed of IL-2/1L-15 receptor beta chain (CD122) and the common gamma chain (gamma-C, CD132). IL-15 regulates the activation and proliferation of T and natural killer (NK) cells.

The term "IL-21" has its general meaning and refers to the human interleukin-21. IL-21 has been ascribed to pleiotropic properties, including, but not limited to, enhancing NK cell and CD8+ T cell cytotoxicity, modulating plasma cell differentiation and inhibiting Treg cells.

The term "IL-33" has its general meaning and refers to the human interleukin-33. IL-33, considered as an alarmin released upon tissue stress or damage, is a member of the IL-1 family and binds the ST2 receptor. IL-33 is known as an effective stimulator of TH1 immune cells, natural killer (NK) cells, iNKT cells, and CD8 T lymphocytes.

The term "PD-1" has its general meaning in the art and refers to the programmed death-1 receptor. The term "PD-1" also refers to a type I transmembrane protein, belonging to the CD28-B7 signalling family of receptors that includes CD28, cytotoxic T-lymphocyte-associated antigen 4 (CTLA-4), inducible costimulator (ICOS), and B- and T-lymphocyte attenuator (BTLA) (Greenwald RJ et al., 2005, Riley JL et aL., 2005).

The term "BTLA" has its general meaning in the art and refers to B and T lymphocyte attenuator. The term "BTLA" also refers to CD272, a member of the CD28-B7 signalling family of receptors that includes CD28, cytotoxic T-lymphocyte-associated antigen 4 (CTLA-4), inducible costimulator (ICOS), and programmed death-1 receptor (PD-1) (Greenwald RJ et al., 2005, Riley JL et aL., 2005).

The term "anti-PD-1 antibody" or "anti-PD-L1" has its general meaning in the art and refers to an antibody with binding affinity to PD-1 or PD-L1 respectively, and antagonist activity to PD-1, i.e., it inhibits the signal transduction cascade related to the PD-1 and inhibits PD-1 ligand binding (PD-L1; PD-L2). Such anti-PD-1 antibody or anti-PD-L1 antibody preferentially inactivates PD-1 with a greater affinity and potency, respectively, than its interaction with the other sub-types or isoforms of the CD28-87 signalling family of receptors (CD28; CTLA-4; ICOS; BTLA). Tests and assays for determining whether a compound is a PD-1 antagonist are well known by the skilled person in the art such as described in Greenwald et al., 2005; Riley et al., 2005.

Examples of such anti-PD1 or anti-PDL1 antibody includes without limitation, nivolumab, pembrolizumab, avelumab, durvalumab, cemiplimab, or atezolizumab.

Examples of such anti-CTLA4 antibody includes without limitation, ipilimumab.

The term "anti-BTLA antibodies" has its general meaning in the art and refers to antibodies that have binding affinity and antagonistic activity to BTLA, i.e. it can inhibit the signal transduction cascade related to the BTLA. Tests and assays for determining whether a compound is a BTLA antagonist are well known by the skilled person in the art such as described in (Greenwald et al., 2005; Riley et al., 2005).

In some embodiments, the anti-BTLA antibodies are selected from those described in the International Patent Application WO2010/106051; WO2011/014438; WO2017/144668.

In some embodiments, the anti-BTLA antibody is the BTLA antibody (BTLA8.2) which is obtainable from the hybridoma accessible under CNCM deposit number 1-4123 such as disclosed in WO2010/106051.

In some embodiments, the anti-BTLA antibody is the 4C7 mAb disclosed in WO2011/014438.

In some embodiments, the anti-BTLA antibody is the mAb 629.3 mAb disclosed in WO2017/144668, or its humanized version or variant thereof.

In accordance with the foregoing the present disclosure provides in a yet further aspect:

A method as defined above comprising co-administration, e.g. concomitantly or in sequence, of a therapeutically effective amount of an anti-BTN3A antibody of the disclosure, and at least one second drug substance, said second drug substance being an anti-viral or anti-proliferative agent or immunotherapeutic agents (such as anti-PD-1, anti-PD-L1 antibodies), or cytokines, e.g. IL-2 or IL-15, or a cell therapy product (such as γδ T cells), e.g. as indicated above.

In one embodiment, the antibodies of the disclosure can be used to detect levels of soluble BTN3A, or levels of cells that express BTN3A. This can be achieved, for example, by contacting a sample (such as an in vitro sample) and a control sample with the anti-BTN3A antibody under conditions that allow for the formation of a complex between the antibody and BTN3A (as expressed at the surface of the cells or soluble BTN3A, for example in a blood sample). Any complexes formed between the antibody and BTN3A are detected and compared in the sample and the control. For example, standard detection methods, well known in the art, such as ELISA and flow cytometric assays, can be performed using the compositions of the disclosure.

Accordingly, in one aspect, the disclosure further provides methods for detecting the presence of BTN3A (e.g., human BTN3A antigen) in a sample, or measuring the amount of BTN3A, comprising contacting the sample, and a control sample, with an antibody or protein of the disclosure, or an antigen binding region thereof, which specifically binds to BTN3A, under conditions that allow for formation of a complex between the antibody or portion thereof and BTN3A. The formation of a complex is then detected, wherein a difference in complex formation between the sample compared to the control sample is indicative of the presence of BTN3A in the sample.

Also within the scope of the present disclosure are kits consisting of the compositions (e.g., humanized antibodies, conjugated antibodies and multispecific molecules) disclosed herein and instructions for use. The kit can further contain a least one additional reagent, or one or more additional antibodies or proteins. Kits typically include a label indicating the intended use of the contents of the kit. The term label includes any writing, or recorded material supplied on or with the kit, or which otherwise accompanies the kit. The kit may further comprise tools for diagnosing whether a patient belongs to a group that will respond to an anti-BTN3A antibody treatment, as defined above.

Another therapeutic strategy is based on the use of the humanized antibodies disclosed herein as agents which selectively expand and/or activate Vγ9 Vδ2 T cells isolated from a sample of a human subject.

The disclosure thus relates to a method for treating a subject in need thereof, comprising:
(a) isolating blood cells comprising Vγ9 Vδ2 T cells, for example PBMCs from a blood sample of a subject,
(b) expanding in vitro Vγ9 Vδ2 T cells in the presence of any one of mAbs 1, 2, 4 and 5, and, optionally, other tumor or accessory cells,
(c) collecting the expanded Vγ9 Vδ2 T cells,
(d) optionally, formulating the expanded Vγ9 Vδ2 T cells and administering a therapeutically efficient amount of said Vγ9 Vδ2 T cells to the subject.

The disclosure further relates to the use of the humanized antibodies disclosed herein (such as mAb1, mAb2, mAb4 or mAb5) as agents which selectively expand Chimeric Antigen Receptor (CAR) Vγ9 Vδ2 T cells. CAR γδ T cells and their use in adoptive T cell cancer immunotherapy are described for example in Mirzaei et al (Cancer Lett 2016, 380(2): 413-423).

The disclosure also relates the anti-BTN3A antibodies for use in vivo as potentiating agent of tumor cells in a γδ T cell therapy in a subject in need thereof, typically suffering from cancer.

As used herein, the term γδ T cell therapy refers to a therapy which comprises the administration to a subject in need thereof of at least an efficient amount of γδ T cells. Such γδ T cells may be allogeneic or autologous. In specific embodiments, the γδ T cells can be genetically engineered by deletion or knock-out or insertion or knock-in of specific genes. In specific embodiments, said γδ T cells include γδ T cells expressing chimeric antigen receptor. The γδ T cells may have been expanded and/or purified ex vivo. Alternatively, the γδ T cells may also be comprised in a cell composition comprising other blood cells, and for example other cells of the immune system. For references regarding γδ T cell therapy, please see Pauza CD. et al, Front Immunol. 2018 Jun. 8; 9:1305. doi: 10.3389, Saudemont A. et al, Front Immunol. 2018 Feb. 5; 9:153. doi: 10.3389.

Indeed, without being bound by any particular theory, a proposed mode of action of the anti-BTN3A antibodies of the present disclosure is that their binding to BTN3A expressed at the surface of a tumor cell triggers a conformational change that allows its signaling to its counter-receptor on Vγ9Vδ152 T cells.

The disclosure thus relates to a method of treatment of a subject suffering from cancer, e.g. hematological malignancies, in particular, leukemias such as acute myeloid leukemia, and having tumor cells, for example blood tumor cells, said method comprising:
(i) administering in said subject an efficient amount of anti-BTN3A antibodies as disclosed herein, typically mAb1, mAb2, mAb4 or mAb5, and,
(ii) administering an efficient amount of γδ T cell composition in said subject,
wherein said efficient amount of anti-BTN3A antibodies has the capacity to potentiate antitumor cytolysis mediated by said γδ T cell composition against said tumor cells.

The disclosure further relates to a method for treating a subject suffering from cancer with solid tumor cells, e.g. ovarian cancer cells, said method comprising:
(i) administering in said subject an efficient amount of anti-BTN3A antibodies as disclosed herein, typically mAb1, mAb2, mAb4 or mAb5, and,
(ii) administering an efficient amount of γδ. T cell composition in said subject, wherein said efficient amount of anti-BTN3A antibodies has the capacity to potentiate antitumor cytolysis mediated by said γδ T cell composition against said tumor cells.

The disclosure also pertains to a method for treating a subject in need thereof, said method comprising the combined (simultaneous or sequential) administration of CAR T cells, for example CAR γδ T cells, and an humanized antibody as disclosed herein (such as mAb1, mAb2, mAb4 or mAb5).

The invention having been fully described is now further illustrated by the following examples, which are illustrative only and are not meant to be further limiting.

EXAMPLES

Figure 1:
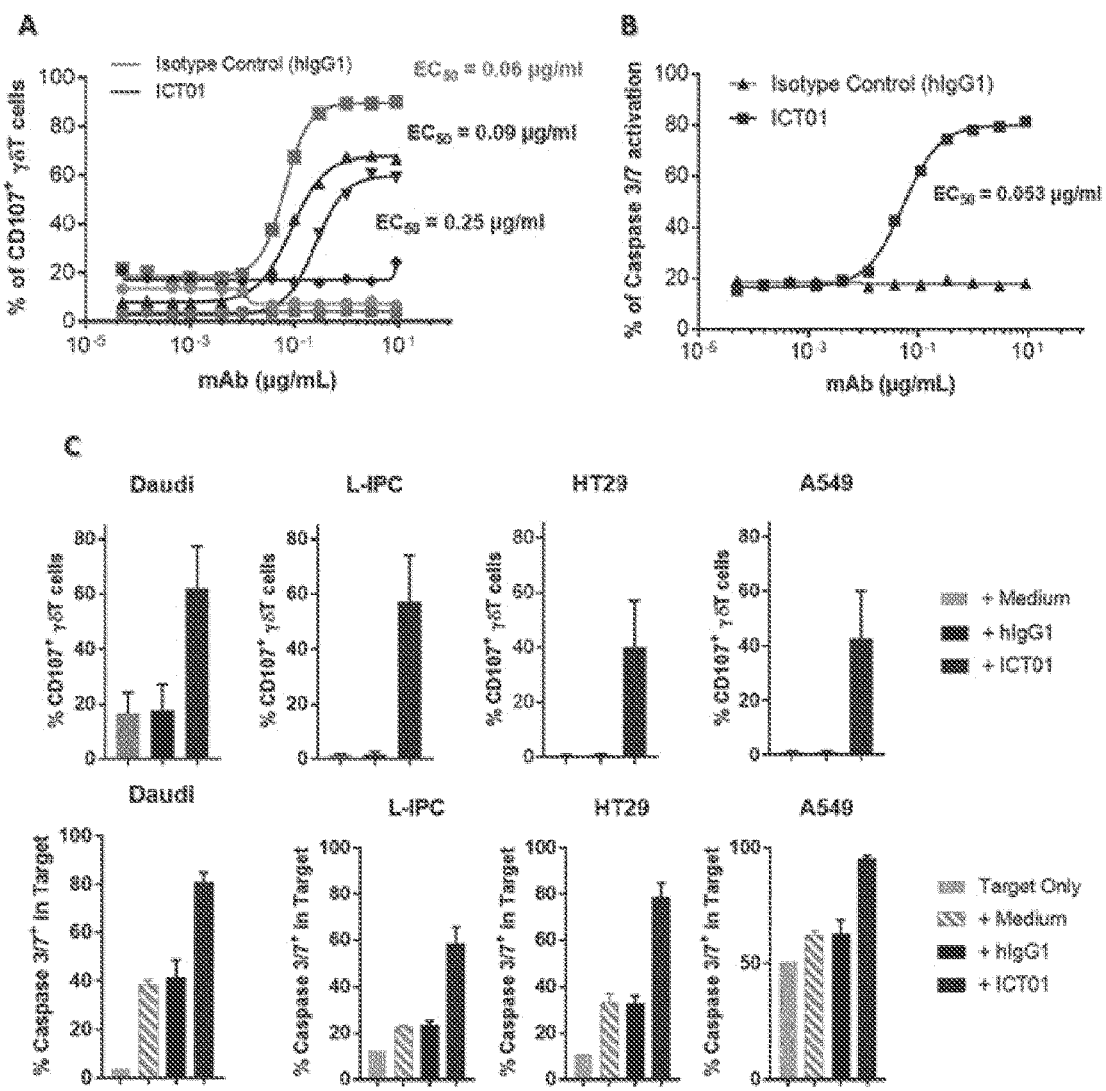
FIG. 1: A. Human Vγ9Vδ2 T cells expanded from PBMCs were co-cultured with Daudi cell line (Burkitt's lymphoma) at ratio E:T 1:1 with the indicated concentrations of mAb1 (or the corresponding isotype control) during 4 hours. Cells were stained with antibodies to CD107a and CD107b and gates for positive expression were based on unstimulated controls. The experiment was done with 3 healthy donors. B. Daudi cells were pre-incubated for 1 hour at 37° C. with the indicated concentrations of mAb1 (or the corresponding isotype control). After extensive washes, mAb-pulsed Daudi cells were co-cultured during 4 hours with expanded human Vγ9Vδ2 T cells at 37° C. before measuring Caspase 3/7 activity on Daudi. For A and B, curves fitting were obtained using sigmoidal 4PL equation from GraphPad Prism software. C. Same protocol was used as previously described in (A) and (B) to assess the efficacy mAb1 (and the corresponding isotype control) used at 10 pg/mL on other tumoral cell lines (L-IPC: Pancreatic Ductal Adenocarcinoma, HT29: Colorectal adenocarcinoma, A549: Lung carcinoma) in comparison with Daudi cell line.
Figure 2:
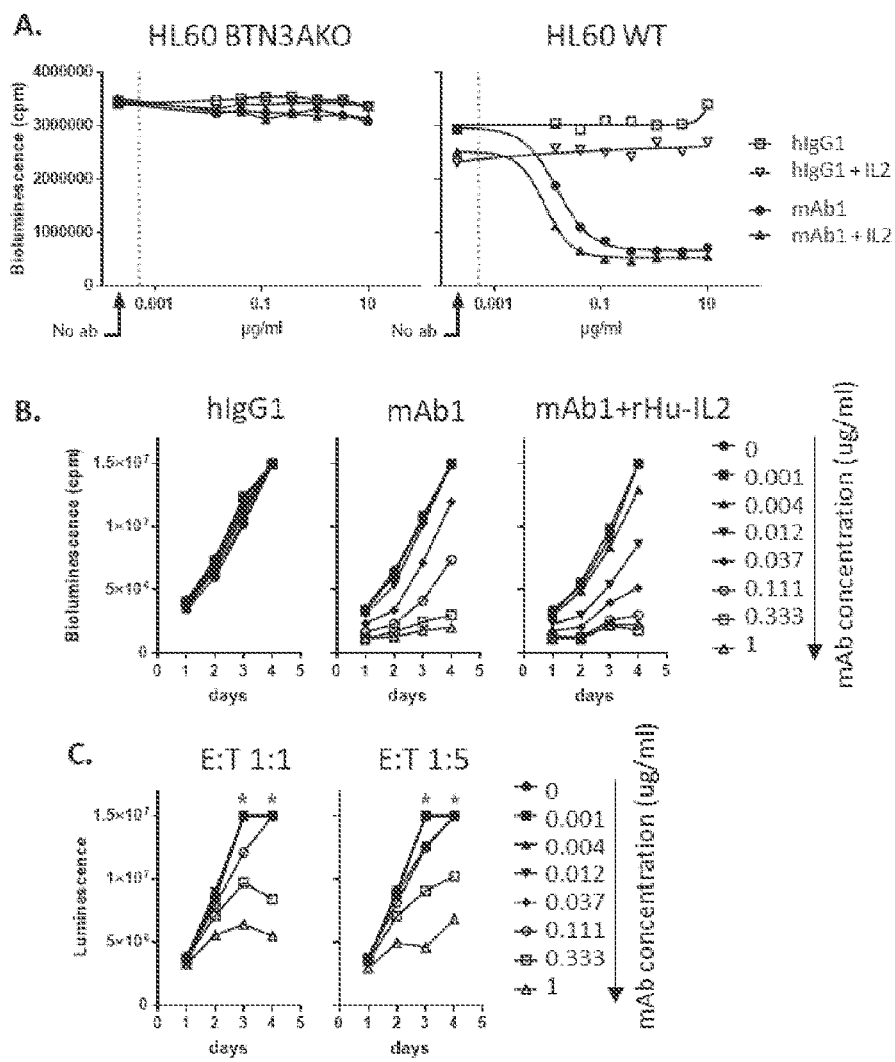
FIG. 2: mAb1-mediates BTN3A expressing target cell killing by Vγ9Vδ2 T-cells.
A. 10,000 HL60-WT or BTN3AKO cells (acute myeloid leukaemia) were co-cultured 24 hrs with in-vitro expanded Vγ9Vδ2 T-cells (ratio E:T 1:1) in presence of increasing concentration of mAb1 (or relevant isotype control hIgG1)+/− rHuIL-2 (20 IU/ml). Cell viability was measured using bioluminescent assay detecting ATP levels.
B. 10,000 HL60-WT cells were co-cultured for 4 days with in-vitro expanded Vγ9Vδ2 T-cells (ratio E:T 1:1) in presence of increasing concentration of mAb1 (or relevant isotype control hIgG1)+/− rHuIL-2 (20 IU/ml). Cell viability was measured every day.
C. 10,000 HL60-WT cells were co-cultured for 4 days with fresh Vγ9VS2 T-cells isolated from human PBMC (ratio E:T 1:1 and 1:5) in presence of increasing concentration of mAb1+ rHuIL-2 (20 IU/ml). Cell viability was measured every day. * mark over signal.
Figure 3:
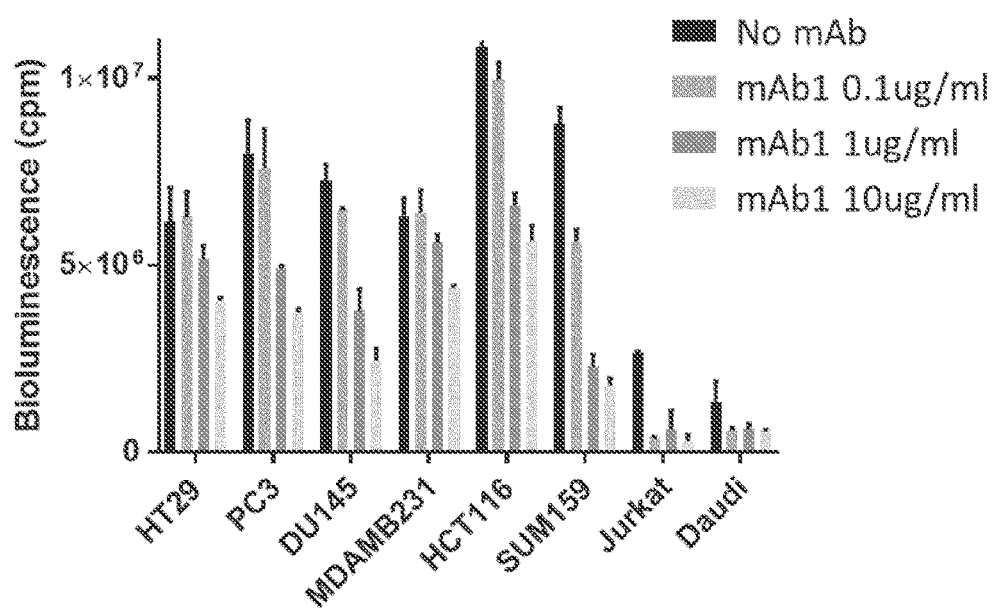
FIG. 3: 10,000 Tumoral cells from different tissues origin were co-cultured 24 hrs with in-vitro expanded Vγ9V52 T-cells (ratio E:T 1:1) in presence of different concentration of mAb1. Cell viability was measured using bioluminescent assay detecting ATP levels. Bioluminescence values are indicated. The 4 bars refers to, from left to right: (1) No mAb, (2) mAb1 0,1 ug/ml, (3) mAb1 1uh/ml, (4) mAb1 10 ug/ml

Selection of Humanized Variants
1. Description of Humanization Strategies
a. Design of Composite Human Antibody™ Variable Region Sequences Structural models of the murine 7.2 and 20.1 antibody V regions were produced using Swiss PDB and analyzed in order to identify important "constraining" amino acids in the V regions that were likely to be essential for the binding properties of the antibodies. Most residues contained within the CDRs (using both Kabat and Chothia definitions) together with a number of framework residues were considered to be important. From the above analysis, Composite Human sequences of 7.2 and 20.1 antibodies have been created.

b. CD4+ T Cell Epitope Avoidance

Based upon the structural analysis, a large preliminary set of sequence segments that could be used to create 7.2 and 20.1 humanized variants were selected and analyzed using iTope™ technology for in silico analysis of peptide binding to human MHC class II alleles (Perry et al., 2008), and using the TCED™ of known antibody sequence-related T cell epitopes (Bryson et al., 2010). Sequence segments that were identified as significant non-human germline binders to human MHC class II or that scored significant hits against the TCED™ were discarded. This resulted in a reduced set of segments, and combinations of these were again analyzed, as above, to ensure that the junctions between segments did not contain potential T cell epitopes. Selected sequence segments were assembled into complete V region sequences predicted to be devoid of significant T cell epitopes. Several heavy chains and light chains sequences were then chosen for gene synthesis and expression in mammalian cells for mAbs 7.2 and 20.1.

2. Generation of Humanized Variants and Preliminary Characterization a. Construction of Humanized Variants Plasmids 7.2 and 20.1 humanized variants were synthesized with flanking restriction enzyme sites for cloning into an expression vector system for human IgG4 (S241P, L248E) heavy and kappa light chains. All constructs were confirmed by sequencing.

b. Expression of Antibodies

Chimeric 7.2 and 20.1 (VH0/Vκ0), two control combinations (VH0/Vκ1, VH1/W0) and combinations of humanized heavy and light chains were transiently transfected into FreeStyle™ CHO-S cells (ThermoFisher, Loughborough, UK) using a MaxCyte STX® electroporation system (MaxCyte Inc., Gaithersburg, USA) from corresponding endotoxin-free DNA. Transfections were undertaken for each antibody using OC-400 processing assemblies. Following cell recovery, cells were diluted to 3 x$10^6$ cells/mL into CD Opti-CHO medium (ThermoFisher, Loughborough, UK) containing 8 mM L-Glutamine (ThermoFisher, Loughborough, UK) and 1×Hypoxanthine-Thymidine (ThermoFisher, Loughborough, UK). 24 hours post-transfection, the culture temperature was reduced to 32° C. and 1 mM sodium butyrate (Sigma, Dorset, UK) was added. Cultures were fed daily by the addition of 3.6% (of the starting volume) feed (2.5% CHO CD Efficient Feed A (ThermoFisher, Loughborough, UK), 0.5% Yeastolate (BD Biosciences, Oxford, UK), 0.25 mM Glutamax (ThermoFisher, Loughborough, UK) and 2 g/L Glucose (Sigma, Dorset, UK)). IgG supernatant titers were monitored by IgG ELISA and transfections were cultured for up to 14 days prior to harvesting supernatants.

c. Preliminary Affinity Measurement: Single Cycle Kinetic Analysis of Humanized Variants Binding to BTN3A In order to assess the binding of all 7.2 and 20.1 Composite Human Antibody™ variants and to select antibodies with the highest affinity to BTN3A, single cycle kinetic analysis was performed on supernatants from transfected cell culture using a Biacore T200 (Ser. No. 1909913) running Biacore T200 Evaluation Software V2.0.1 (Uppsala, Sweden).

Antibodies were diluted in 2% BSA/PBS to a final concentration of 2 pg/ml based on concentrations obtained from the supernatant titered by ELISA. At the start of each cycle, antibodies were loaded onto Fc2, Fc3 and Fc4 of the Protein A chip (GE Healthcare, Little Chalfont, UK). IgGs were captured at a flow rate of 10 μl/min to give an immobilization level (RL) of ~146.5 RU, the theoretical value to obtain RMax of ~50 RU. The surface was then allowed to stabilize. Single cycle kinetic data was obtained with BTN3A1-His as the analyte (Sino Biological Cat. No. 15973-H08H) at a flow rate of 60 μl/min to minimize any potential mass transfer effects, as well as using HBS-P+(GE Healthcare, Little Chalfont, UK) as running buffer. Multiple repeats with the chimeric antibody were performed to check the stability of the surface and analyte over the kinetic cycles. The signal from the reference channel Fc1 (no antibody) was subtracted from that of Fc2, Fc3 and Fc4 to correct for differences in non-specific binding to the reference surface. A three point, four-fold dilution range from 1.56 nM to 25 nM BTN3A1 without regeneration between each concentration was used. The association phase for the three injections of increasing concentrations of BTN3A1 was monitored for 240 seconds each time and a single dissociation phase was measured for 2000 seconds following the last injection of BTN3A1. Regeneration of the Protein A surface was conducted using two injections of 10 mM glycine-HCL pH 1.5 followed by a stabilization period of 240 seconds.

The signal from each antibody blank run (no CD277) was subtracted to correct for differences in surface stability. Single cycle kinetics demonstrated that all humanized variants bound to BTN3A.

d. Purification of Antibodies

Based on the affinities calculated by Biacore, as well as the iTope™ score and percentage of humanness of each humanized variant, 7.2 and 20.1 humanized variants with the best affinities and best iTope™ scores were selected for further analysis.

The selected humanized variants together with their chimeric version and the most conservatively humanized variant (VH1/Vκ1) were subjected to purification for further assay testing. Antibodies were purified from cell culture supernatants on Protein A sepharose columns followed by Size Exclusion Chromatography (SEC) (GE Healthcare, Little Chalfont, UK) using 10 mM sodium acetate, 100 mM NaCl, pH 5.5 as mobile phase and final formulation buffer. Samples were quantified by $OD_{280nm}$ using an extinction coefficient (Ec(0.1%)) based on the predicted amino acid sequence.

Antibodies were analyzed using SDS-PAGE by loading 2 μg of each antibody on the gel and bands corresponding to the profile of a typical antibody were observed.

e. Validation of Binding Properties: Competition ELISA Analysis Between Humanized and Chimeric 7.2 and 20.1 mAbs Purified variants were tested for their binding to recombinant BTN3A1-His (Sino Biological cat. no. 15973-H08H) while competing against the corresponding murine antibody. Chimeric (VH0/Vκ0) and irrelevant human IgG4 (S241P, L248E) were tested on each plate for comparison.

BTN3A1 was diluted in 1x PBS to 0.5 μg/ml and 100 μl/well was coated overnight at 4° C. on a 96-well ELISA plate. The following day, the plate was washed 3× with 1x PBS/0.05% Tween (PBS-T) and blocked with 200 μl of 2% milk/PBS for one hour at room temperature. In a dilution 96-well plate a fixed concentration of murine antibodies 7.2 or 20.1 (0.15 μg/ml final concentration) was added in equal volume to a four-fold titration series of test antibody (starting from 80 μg/ml (40 μg/ml final concentration) diluted in blocking buffer). After washing the Nunc ELISA plate 3× with PBS-T, 100 μl of murine/test antibody mix was added to the ELISA plate. After one hour incubation at room temperature, the plate was washed 3× with PBS-T and 100 μl of anti-mouse Fc HRP-labelled secondary antibody (Sigma, Dorset, UK) diluted 1:1000 in blocking buffer was applied for one hour at room temperature to detect bound murine antibody. For color development, the plate was washed 3× with PBS-T following which 100 μl of TMB substrate was added and incubated for five minutes at room temperature. The reaction was stopped with 100 μl of 3.0 M hydrochloric acid and absorbance was read immediately using a Dynex plate reader at 450 nm. $IC_{50}$ values were calculated for each variant and relative $IC_{50}$ values were calculated by dividing the $IC_{50}$ of the humanized variant by that of the chimeric antibody assayed on the same plate.

3. Selection of the Humanized Candidates a. Multi-Cycle Kinetic Analysis

Based on the data generated from competition ELISA and thermal stability assessment, multi-cycle kinetic analysis was performed on most of the humanized 7.2 and 20.1 variants together with the VH0/Vκ0 chimeric antibody using a Biacore T200 (Ser. No. 1909913) instrument running Biacore T200 Evaluation Software V2.0.1 (Uppsala, Sweden).

Purified antibodies were diluted to a concentration of 2 pg/ml in 2% BSA/PBS. At the start of each cycle, each antibody was captured on the Protein A at a density (RL) of ~146.5 RU (theoretical value to obtain an RMax of ~50 RU). Following capture, the surface was allowed to stabilize before injection of the BTN3A1 antigen (Sino Biological cat. no. 15973-H08H). BTN3A1 was titrated in 0.1% BSA/HBS-P+(running buffer) in a two-fold dilution range from 25 to 0.78 nM. The association phase was monitored for 400 seconds and the dissociation phase for 35 minutes (2100 seconds). Kinetic data was obtained using a flow rate of 50 μl/min to minimize any potential mass transfer effects. Regeneration of the Protein A surface was conducted using two injections of 10 mM glycine-HCL pH 1.5 at the end of each cycle. Two blanks (no BTN3A1) and a repeat of a single concentration of the analyte were performed for each tested antibody to check the stability of the surface and analyte over the kinetic cycles. The signal from the reference channel Fc1 was subtracted from that of Fc2, Fc3 and Fc4 to correct for differences in non-specific binding to a reference surface. Additionally, blank runs were subtracted for each Fc to correct any antigen-independent signal variation, such as drift. Sensorgrams were fitted using a one-to-one binding mathematical model with a global RMax parameter and no bulk signal (Constant RI=0 RU).

b. Binding Assay by Flow Cytometry on Human PBMCs 7.2 and 20.1 humanized variants were characterized for their binding to human PBMCs, isolated from blood of healthy donors. PBMCs were isolated from buffy coats using Lymphoprep (Axis-shield, Dundee, UK) density centrifugation. PBMCs were then frozen and stored at −80° C. or in liquid nitrogen until required. 100 μl cells at 1×10⁶ cells/ml were transferred to each well of a fresh U-shaped bottom 96-well plate, then the plate was centrifuged and supernatant discarded.

A serial dilution of the antibodies, 0.001 pg/ml to 150 pg/ml was prepared in PBS 2 mM EDTA. Human PBMCs were resuspended in 50 μl of the diluted test antibody titration series prepared.

After incubation for 30 minutes at 4° C. in the dark, the plate was centrifuged and washed twice with 150 μl/well of PBS 2 mM EDTA following which the wells were resuspended in 50 μl of a mix composed of goat anti-human antibody (PE labelled) diluted 1/100 and Live/dead neat IR diluted 1/500 in PBS 2 mM EDTA.

After incubation for 15 minutes at 4° C. in the dark, the plate was centrifuged and washed once with 150 µl/well PBS 2 mM EDTA following which the wells were resuspended in 200 µl PBS 2 mM EDTA. Cells were analyzed on a BD LSR Fortessa Cytometer. Data was analyzed using a FlowJo software (Version 10, FlowJo, LLC, Ashland, USA) (Data not shown).

Same protocol was performed on cynomolgus PBMCs and on Daudi Burkitt's lymphoma cell line.

c. In Vitro Functional Efficacy: γδ-T Cell Degranulation Assay

The assay consists of measuring activating or inhibitory effect of 7.2 and 20.1 humanized variants and their chimeric versions on γδ-T cell degranulation against Daudi Burkitt's lymphoma cell line (Harly et al., 2012). γδ-T cells were expanded from PBMCs of healthy donors by culturing with zoledronic acid (1 µM) and IL2 (200 Ui/ml) for 11-13 days. IL2 is added at day 5, day 8 and every 2 days thereafter. The percentage of γδ-T cells was determined at the initiation of culture and assessed for the time of culture by flow cytometry until it reached at least 80%. Frozen or fresh γδ-T cells were then used in degranulation assays against Daudi cell line (E:T ratio of 1:1), whereby the cells are co-cultured for 4 hours at 37° C. in presence of 10 mg/ml of the 7.2 and 20.1 humanized variants and their chimeric versions. Activation by PMA (20 ng/ml) plus Ionomycin (14/ml) served as positive control for γδ-T cell degranulation, and medium alone as negative control. At the end of 4 hour co-incubation, cells were analyzed by flow cytometry to evaluate the percentage of γδ-T cells positive for CD107a (LAMP-1, lysosomal-associated membrane protein-1)+CD107b (LAMP-2). CD107 is mobilized to the cell surface following activation-induced granule exocytosis, thus measurement of surface CD107 is a sensitive marker for identifying recently degranulated cytolytic T cells. The results did not show any significant variations among the tested candidates, which showed similar activating effect in the degranulation assay as the chimeric 7.2 or 20.1 antibody.

The same protocol was performed using AML blasts isolated from patients as target cells, in place of Daudi cells.

d. Thermostability Analysis

In order to assess the thermostability of the selected 7.2 and 20.1 Composite Human Antibody™ variants, melting temperatures (the temperature at which 50% of a protein domain is unfolded) were determined using a fluorescence-based thermal shift assay.

All purified humanized antibodies, and the chimeric (VH0/Vκ0) antibodies, were diluted to a final concentration of 0.1 mg/ml in formulation buffer (10 mM sodium acetate, 100 mM NaCl, pH 5.5) containing SYPRO® Orange (ThermoFisher, Loughborough, UK) at 1 in 1000 dilution and subjected to a temperature gradient from 25° C. to 99° C. on a StepOnePlus real-time PCR system (ThermoFisher, Loughborough, UK) over a period of 56 minutes. 10 mM sodium acetate, 100 mM NaCl, pH 5.5 was used as a negative control. The melting curves were analyzed using protein thermostability software (version 1.2).

e. Selection of Humanized Candidates

Based on all the results obtained for the experiments described above, 3 variants out of 35 (15 humanized variants generated for 7.2; 20 humanized variants generated for 20.1) were selected for further characterization: 7.2 (VH2/Vk1), 7.2 (VH2Nk2) and 20.1 (VH3/Vk1).

The results of the different experiments described above for the mAbs 7.2 and 20.1 are reported in the Table 4 and Table 5 for the 3 variants and their chimeric versions.

TABLE 4

| | The selected humanized candidates have the same potency as the murine parent antibodies | | | | |
|---|---|---|---|---|---|
| Candidate | 7.2 VH2/Vk1 | 7.2 VH2/Vk2 | 7.2 VH0/Vκ0 | 20.1 VH3/Vk1 | 20.1 VH0/Vκ0 |
| Biacore affinity Multi-Cycle Kinetics ($\times 10^{-10}$) ($K_D$, M) | 2.53 | 2.43 | 1.76 | 3.19 | 2.34 |
| Binding on human PBMC ($EC_{50}$, µg/mL) | 3.86 | 5.94 | 3.6 | 3.38 | 3.02 |
| Binding Cyno PBMC ($EC_{50}$, µg/mL) | 12.0 | 9.85 | 7.75 | 5.74 | 4.06 |
| Binding to lymphoma (Daudi) ($EC_{50}$, µg/mL) | 2.02 | 2.01 | 1.44 | 1.59 | 1.19 |
| Functional assay (Daudi) (γδT cell-based, $EC_{50}$, µg/mL) | 0.03 | 0.03 | 0.02 | 0.02 | 0.02 |
| Functional assay (AML sensitive) (γδT cell-based, $EC_{50}$, µg/mL) | 0.21 | 0.19 | 0.12 | 0.15 | 0.05 |
| Functional assay (AML resistant) (γδT cell-based, $EC_{50}$, µg/mL) | 0.73 | 0.64 | 0.42 | 0.32 | 0.18 |

TABLE 5

The humanized selected candidates mAb7.2 with VH2 and either Vk1 or Vk2 have higher thermostability as compared to murine candidate

| Candidate | 7.2 VH2/Vk1 | 7.2 VH2/Vk2 | 7.2 VH0/Vk0 |
|---|---|---|---|
| Thermostability ($T_m2$ mean) (° C.) | 77.1 | 77.3 | 72.5 |

The humanization process lead to the generation of multiple 7.2 and 20.1 variants with predicted reduced immunogenicity.

The selected set of the three variants (7.2 VH2NK1, 7.2 VH2/VK2 and 20.1 VH3/VK1) showed equivalent properties as their chimeric version in terms of affinity, binding and efficacy in functional assays: the modifications made in the variants sequences to reduce immunogenicity did not alter the antibodies functions.

Surprisingly, the thermostability of the selected humanized variants 7.2 VH2/VK1, 7.2 VH2/VK2 was improved compared to the chimeric antibodies, and such improved thermostability was unexpected in this process of humanization.

Constant Region of the Antibody: Comparison of Silent Fc Fragments

Several Fc portions were tested to silence or reduce the effector function of the antibodies. The binding of these Fc fragments to the different Fcγ receptors was assessed using Biacore; their binding on C1q complex was assessed by ELISA assay.

1. Binding of the engineered Fc portion to the different Fcγ receptors using Biacore The ability of different isotypes (IgG1, IgG1 [N314A], IgG1 [L247F, L248E P350S], IgG2, IgG4 [S241P] and IgG4 [S241P L248E]) of the chimeric antibody 20.1 to bind to different Fcγ receptors was determined using purified antibodies and single cycle Biacore analysis. The human Fc receptors, FcγRI, FcγRIIA (Arg167 polymorphism) and IIB, and FcγRIIIA (Phe176 polymorphism) and IIIB were obtained from Sino Biological.

Fcγ receptors were diluted in HBS-P+(GE Healthcare, Little Chalfont, UK) to a final concentration of either 0.5 or 1.0 pg/ml. At the start of each cycle, Fcγ receptors were loaded onto Fc2, Fc3 and Fc4 of an anti-His CM5 chip (GE Healthcare, Little Chalfont, UK). Fcγ receptors were captured at a flow rate of 5 μl/min to give an immobilization level of between 30 and 180 RU depending on the molecular weight of the Fcγ receptor. The surface was then allowed to stabilize. Single-cycle kinetics data was obtained using the chimeric antibodies as the analyte at a flow rate of 30 μl/min to minimize any potential mass transfer effects. The signal from the reference channel Fc1 (no antibody) was subtracted from that of Fc2, Fc3 and Fc4 to correct for differences in non-specific binding to the reference surface. A five point, three-fold dilution range was used for each chimeric antibody with this concentration range varying for each individual Fcγ receptor due to the expected differences in affinity. The signal from each blank run (no antibody) was subtracted to correct for differences in surface stability. The association phase for each of the five injections of increasing concentrations of chimeric antibody was monitored for between 25 and 180 seconds (depending on the Fcγ receptor ligand) and a single dissociation phase was measured for between 25 and 300 seconds following the last injection of antibody. Regeneration of the anti-His surface was conducted using two injections of 10 mM glycine-HCL pH 1.5 for 15 seconds each at 30 μl/min followed by a stabilization period of 180 seconds.

Single-cycle kinetic constants were determined where possible using the standard 1:1 analysis model. For strong interactions it was generally more suitable to determine affinity via kinetic experiments. However, for several Fcγ receptors, the interaction is very weak and in this scenario, the data was analyzed using steady state affinity analysis (which is particularly suited to measurement of weak to moderate interactions). Sensorgrams for the interactions of the Fcγ receptors with the chimeric antibodies were obtained (data not shown).

As expected, the high affinity FcγRI receptor bound with good affinity to unmodified IgG1 and IgG4 (S241P). The modified IgG1 isotypes, together with IgG2 and IgG4 (S241P, L248E) failed to bind to FcγRI. The remaining Fcγ receptors showed much lower affinity interactions for the different chimeric antibodies compared to the FcγRI. As expected, the unmodified IgG1 showed the strongest binding to all four of the lower affinity receptors, whereas the modified versions of IgG1 showed significantly reduced binding to these receptors. IgG2 and IgG4 (S241P) demonstrated some binding to FcγRIIA and B but only marginal binding to FcγRIIIA and B.

2. Binding of the engineered Fc portion to the C1q complex by ELISA assay

The chimeric antibody 20.1 was tested as different IgG isotypes for binding to the C1q complex to determine their ability to activate the complement system.

In a U-bottomed 96-well plate, a 2.5-fold dilution series (from 10 pg/ml to 0.04 pg/ml) of purified chimeric 20.1 in different isotypes was prepared in 2% BSA/DPBS. Nunc Immuno MaxiSorp 96 well flat bottom microtitre plates (ThermoFisher Scientific, Loughborough, UK) were pre-coated with 100 μl/well of this titration series and incubated overnight at 4° C. The following day the plate was washed twice with PBST and blocked for one hour at room temperature with 2% BSA/DPBS before washing five times with PBST. Purified complement protein C1q (Pathway Diagnostics Ltd, Dorking, UK), diluted to 5 pg/ml in 2% BSA/PBS, was added to the plate (100 μl/well) and incubated for one hour at room temperature. After washing five times with PBST, the binding of C1q complex was detected with an anti-C1q-HRP (Abcam, Cambridge, UK) (100 μl/well, diluted 1 in 100 in 2% BSA/DPBS) for one hour at room temperature. After washing five times with PBST, binding was detected with TMB substrate (ThermoFisher Scientific, Loughborough, UK) following which the reaction was stopped with 3 M HCl, absorbance read at 450 nm on a Dynex Technologies MRX TC II plate reader and the binding curves plotted.

As expected, only the unmodified IgG1 isotype showed good binding to C1q with other isotypes showing minimal to no binding (data not shown).

3. Selection of the Engineered Fc Fragments

The relative binding of all tested isotypes on Fcγ receptors and C1q complex are described in Table 6.

TABLE 6

Relative binding of all isotypes on Fcγ receptors and C1q complex

| Isotype | FcγRI | FcγRIIa | FcγRIIb | FcγRIIIa | FcγRIIIb | C1q |
|---|---|---|---|---|---|---|
| IgG1 | | | | | | |
| IgG1 WT | ++++ | ++ | ++ | ++ | ++ | ++++ |
| IgG1 N314A | ++ | − | − | − | − | − |
| IgG1 L247F, L248E, P350S | − | + | + | +/− | +/− | − |
| IgG2 | | | | | | |
| IgG2 WT | − | ++ | + | +/− | +/− | +/− |
| IgG4 | | | | | | |
| IgG4 S241P | ++++ | ++ | ++ | +/− | +/− | − |
| IgG4 S241P, L248E | − | + | ++ | − | +/− | − |

The two engineered IgG1 L247F, L248E, P350S and IgG4 S241P, L248E Fc fragments were the only one to show a total loss of binding on FcγI receptor and C1q complex.

Based on the results obtained, the two engineered IgG1 L247F, L248E, P350S and IgG4 S241 P, L248E isotypes were selected for further characterization.

Generation of 6 Humanized Antibodies

The 3 selected humanized variants were cloned to be fused with the two selected engineered Fc fragments, leading to the generation of 6 different candidates: mAb 1 to mAb 6.

The Examples mAb1 to mAb6 as described in Table 1 can be produced using conventional antibody recombinant production and purification processes.

For example, the coding sequences have been cloned into a production vector for recombinant expression in mammalian production cell line.

The following Tables 7 and 8 provides detailed amino acid and nucleotide sequences useful for practicing the invention, and in particular for producing the nucleic acids, expression vectors and humanized antibodies derived from the murine 7.2 of the present disclosure.

TABLE 7

Brief description of useful amino acid and nucleotide sequences for practicing the invention

| SEQ ID NO: | Type | Description of the sequence |
|---|---|---|
| 1 | aa | Humanized heavy chain variable region VH2 of mAb 7.2 |
| 2 | aa | Humanized light chain variable region Vκ1 of mAb 7.2 |
| 3 | aa | Humanized light chain variable region Vκ2 of mAb 7.2 |
| 4 | aa | Full length heavy chain of mAbs 1 and 2 (VH2 7.2 silent IgG1) |
| 5 | aa | Full length heavy chain of mAbs 4 and 5 (VH2 7.2 silent IgG4) |
| 6 | aa | Full length light chain of mAbs 1 and 4 (Vk1 7.2) |
| 7 | aa | Full length light chain of mAbs 2 and 5 (Vk2 7.2) |
| 8 | nt | Full length heavy chain of mAbs 1 and 2 (VH2 7.2 silent IgG1) |
| 9 | nt | Full length heavy chain of mAbs 4 and 5 (VH2 7.2 silent IgG4) |
| 10 | nt | Full length light chain of mAbs 1 and 4 (Vk1 7.2) |
| 11 | nt | Full length light chain of mAbs 2 and 5 (Vk2 7.2) |
| 12 | aa | HCDR1 of mAb 7.2, 1, 2, 4 and 5 |
| 13 | aa | HCDR2 of mAb 7.2, 1, 2, 4 and 5 |
| 14 | aa | HCDR3 of mAb 7.2, 1, 2, 4 and 5 |
| 15 | aa | LCDR1 of mAb 7.2, 1, 2, 4 and 5 |
| 16 | aa | LCDR2 of mAb 7.2, 1, 2, 4 and 5 |
| 17 | aa | LCDR3 of mAb 7.2, 1, 2, 4 and 5 |
| 18 | aa | Human BTN3A1 |
| 19 | aa | Human BTN3A2 |
| 20 | aa | Human BTN3A3 |
| 21 | aa | Cynomolgus macaque (*m. fascicularis*) BTN3A1 ectodomain used for recombinant protein production |
| 22 | aa | Cynomolgus macaque (*m. fascicularis*) BTN3A2 ectodomain used for recombinant protein production |
| 23 | aa | Cynomolgus macaque (*m. fascicularis*) BTN3A3 ectodomain used for recombinant protein production |

TABLE 8

Brief description of useful amino acid and nucleotide sequences for practicing the invention

| SEQ ID NO: | Describes the amino acid or nucleotide sequence below: |
|---|---|
| 1 | QVQLVQSGAEVKKPGASVKLSCKASGYIFTRYYMYWVKQRPGQGLEWIGEI NPNNGGTKFNEKFKNRATLTVDKSISTAYMELSRLRSDDTAVYYCSREDDY DGTPFAMDYWGQGTLVTVSS |
| 2 | DIQMTQSPSSLSASVGDRVTITCHASQNINVWLSWYQQKPGKAPKLLIYKAS NLHTGVPSRFTGSGSGTDFTFTISSLQPEDIATYYCQQGQTYPYTFGQGTKL EIK |
| 3 | DIQMTQSPSSLSASVGDRVTITCHASQNINVWLSWYQQKPGKAPKLLIYKAS NLHTGVPSRFSGSGSGTDFTFTISSLQPEDIATYYCQQGQTYPYTFGQGTKL EIK |
| 4 | QVQLVQSGAEVKKPGASVKLSCKASGYIFTRYYMYWVKQRPGQGLEWIGEI NPNNGGTKFNEKFKNRATLTVDKSISTAYMELSRLRSDDTAVYYCSREDDY DGTPFAMDYWGQGTLVTVSSASTKGPSVFPLAPSSKSTSGGTAALGCLVK DYFPEPVTVSWNSGALTSGVHTFPAVLQSSGLYSLSSVVTVPSSSLGTQTYI CNVNHKPSNTKVDKRVEPKSCDKTHTCPPCPAPEFEGGPSVFLFPPKPKDT |

TABLE 8-continued

Brief description of useful amino acid and nucleotide sequences for practicing the invention

| SEQ ID NO: | Describes the amino acid or nucleotide sequence below: |
|---|---|
|  | LMISRTPEVTCVVVDVSHEDPEVKFNWYVDGVEVHNAKTKPREEQYNSTYR VVSVLTVLHQDWLNGKEYKCKVSNKALPASIEKTISKAKGQPREPQVYTLPP SREEMTKNQVSLTCLVKGFYPSDIAVEWESNGQPENNYKTTPPVLDSDGSF FLYSKLTVDKSRWQQGNVFSCSVMHEALHNHYTQKSLSLSPG |
| 5 | QVQLVQSGAEVKKPGASVKLSCKASGYIFTRYYMYWVKQRPGQGLEWIGEI NPNNGGTKFNEKFKNRATLTVDKSISTAYMELSRLRSDDTAVYYCSREDDY DGTPFAMDYWGQGTLVTVSSASTKGPSVFPLAPCSRSTSESTAALGCLVKD YFPEPVTVSWNSGALTSGVHTFPAVLQSSGLYSLSSVVTVPSSSLGTKTYT CNVDHKPSNTKVDKRVESKYGPPCPPCPAPEFEGGPSVFLFPPKPKDTLMI SRTPEVTCVVVDVSQEDPEVQFNWYVDGVEVHNAKTKPREEQFNSTYRVV SVLTVLHQDWLNGKEYKCKVSNKGLPSSIEKTISKAKGQPREPQVYTLPPSQ EEMTKNQVSLTCLVKGFYPSDIAVEWESNGQPENNYKTTPPVLDSDGSFFL YSRLTVDKSRWQEGNVFSCSVMHEALHNHYTQKSLSLSLG |
| 6 | DIQMTQSPSSLSASVGDRVTITCHASQNINVWLSWYQQKPGKAPKLLIYKAS NLHTGVPSRFTGSGSGTDFTFTISSLQPEDIATYYCQQGQTYPYTFGQGTKL EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTK SFNRGEC |
| 7 | DIQMTQSPSSLSASVGDRVTITCHASQNINVWLSWYQQKPGKAPKLLIYKAS NLHTGVPSRFSGSGSGTDFTFTISSLQPEDIATYYCQQGQTYPYTFGQGTKL EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTK SFNRGEC |
| 8 | CAGGTCCAACTGGTGCAGTCTGGGGCTGAAGTGAAGAAGCCTGGGGCT TCAGTGAAGTTGTCCTGCAAGGCTTCTGGCTACATCTTCACCAGATACTA TATGTATTGGGTGAAGCAGAGGCCTGGACAAGGCCTTGAGTGGATTGGA GAGATTAATCCTAACAATGGTGGTACTAAGTTCAATGAGAAGTTCAAGAA CAGGGCCACACTGACTGTAGACAAATCCATCAGCACAGCATACATGGAG CTCAGCAGGCTGAGATCTGACGACACGGCGGTCTATTATTGTTCAAGAG AGGATGATTACGACGGGACCCCCTTTGCTATGGACTACTGGGGTCAAGG AACCCTGGTCACCGTCTCCTCAGCCTCCACCAAGGGCCCATCGGTCTTC CCCCTGGCACCCTCCTCCAAGAGCACCTCTGGGGGCACAGCGGCCCTG GGCTGCCTGGTCAAGGACTACTTCCCCGAACCGGTGACGGTGTCGTGG AACTCAGGCGCCCTGACCAGCGGCGTGCACACCTTCCCGGCTGTCCTA CAGTCCTCAGGACTCTACTCCCTCAGCAGCGTGGTGACCGTGCCCTCCA GCAGCTTGGGCACCCAGACCTACATCTGCAACGTGAATCACAAGCCCAG CAACACCAAGGTGGACAAGAGAGTTGAGCCCAAATCTTGTGACAAAACT CACACATGCCCACCGTGCCCAGCACCTGAATTCGAGGGGGGACCGTCA GTCTTCCTCTTCCCCCCAAAACCCAAGGACACCCTCATGATCTCCCGGA CCCCTGAGGTCACATGCGTGGTGGTGGACGTGAGCCACGAAGACCCTG AGGTCAAGTTCAACTGGTACGTGGACGGCGTGGAGGTGCATAATGCCAA GACAAAGCCGCGGGAGGAGCAGTACAACAGCACGTACCGTGTGGTCAG CGTCCTCACCGTCCTGCACCAGGACTGGCTGAATGGCAAGGAGTACAA GTGCAAGGTCTCCAACAAAGCCCTCCCAGCCTCCATCGAGAAAACCATC TCCAAAGCCAAAGGGCAGCCCCGAGAACCACAGGTGTACACCCTGCCC CCATCCCGGGAAGAGATGACCAAGAACCAGGTCAGCCTGACCTGCCTG GTCAAAGGCTTCTATCCCAGCGACATCGCCGTGGAGTGGGAGAGCAAT GGGCAGCCGGAGAACAACTACAAGACCACGCCTCCCGTGCTGGACTCC GACGGCTCCTTCTTCCTCTATAGCAAGCTCACCGTGGACAAGAGCAGGT GGCAGCAGGGGAACGTCTTCTCATGCTCCGTGATGCATGAGGCTCTGCA CAACCACTACACGCAGAAGAGCCTCTCCCTGTCTCCGGGTTGA |
| 9 | CAGGTCCAACTGGTGCAGTCTGGGGCTGAAGTGAAGAAGCCTGGGGCT TCAGTGAAGTTGTCCTGCAAGGCTTCTGGCTACATCTTCACCAGATACTA TATGTATTGGGTGAAGCAGAGGCCTGGACAAGGCCTTGAGTGGATTGGA GAGATTAATCCTAACAATGGTGGTACTAAGTTCAATGAGAAGTTCAAGAA CAGGGCCACACTGACTGTAGACAAATCCATCAGCACAGCATACATGGAG CTCAGCAGGCTGAGATCTGACGACACGGCGGTCTATTATTGTTCAAGAG AGGATGATTACGACGGGACCCCCTTTGCTATGGACTACTGGGGTCAAGG AACCCTGGTCACCGTCTCCTCAGCTTCCACCAAGGGCCCATCCGTCTTC CCCCTGGCGCCCTGCTCCAGGAGCACCTCCGAGAGCACAGCGGCCCTG GGCTGCCTGGTCAAGGACTACTTCCCCGAACCGGTGACGGTGTCGTGG AACTCAGGCGCCCTGACCAGCGGCGTGCACACCTTCCCGGCTGTCCTA CAGTCCTCAGGACTCTACTCCCTCAGCAGCGTGGTGACCGTGCCCTCCA GCAGCTTGGGCACGAAGACCTACACCTGCAATGTAGATCACAAGCCCAG CAACACCAAGGTGGACAAGAGAGTTGAGTCCAAATATGGTCCCCCATGC CCACCATGCCCAGCACCTGAGTTCGAGGGGGGACCATCAGTCTTCCTGT TCCCCCCAAAACCCAAGGACACTCTCATGATCTCCCGGACCCCTGAGGT CACGTGCGTGGTGGTGGACGTGAGCCAGGAAGACCCCGAGGTCCAGTT CAACTGGTACGTGGATGGCGTGGAGGTGCATAATGCCAAGACAAAGCC |

TABLE 8-continued

Brief description of useful amino acid and nucleotide sequences for practicing the invention

| SEQ ID NO: | Describes the amino acid or nucleotide sequence below: |
|---|---|
| | GCGGGAGGAGCAGTTCAACAGCACGTACCGTGTGGTCAGCGTCCTCAC<br>CGTCCTGCACCAGGACTGGCTGAACGGCAAGGAGTACAAGTGCAAGGT<br>CTCCAACAAAGGCCTCCCGTCCTCCATCGAGAAAACCATCTCCAAAGCC<br>AAAGGGCAGCCCCGAGAGCCACAGGTGTACACCCTGCCCCCATCCCAG<br>GAGGAGATGACCAAGAACCAGGTCAGCCTGACCTGCCTGGTCAAAGGC<br>TTCTACCCCAGCGACATCGCCGTGGAGTGGGAGAGCAATGGGCAGCCG<br>GAGAACAACTACAAGACCACGCCTCCCGTGCTGGACTCCGACGGCTCCT<br>TCTTCCTCTACAGCAGGCTAACCGTGGACAAGAGCAGGTGGCAGGAGG<br>GGAATGTCTTCTCATGCTCCGTGATGCATGAGGCTCTGCACAACCACTA<br>CACACAGAAGAGCCTCTCCCTGTCTCTGGGTTGA |
| 10 | GACATCCAGATGACCCAGTCTCCATCCAGTCTGTCTGCATCCGTAGGAG<br>ACAGAGTCACCATCACTTGCCATGCCAGTCAGAACATTAATGTTTGGTTA<br>TCTTGGTACCAGCAGAAACCAGGAAAAGCCCCTAAACTCTTGATCTATAA<br>GGCTTCCAACTTGCACACAGGCGTCCCATCAAGATTTACTGGCAGTGGA<br>TCTGGAACAGATTTCACATTCACCATCAGCAGCCTGCAGCCTGAAGACAT<br>TGCCACTTACTACTGTCAACAGGGTCAAACTTATCCATACACGTTCGGAC<br>AGGGGACCAAGCTGGAGATCAAACGAACTGTGGCTGCACCATCTGTCTT<br>CATCTTCCCGCCATCTGATGAGCAGTTGAAATCTGGAACTGCCTCTGTTG<br>TGTGCCTGCTGAATAACTTCTATCCCAGAGAGGCCAAAGTACAGTGGAA<br>GGTGGATAACGCCCTCCAATCGGGTAACTCCCAGGAGAGTGTCACAGA<br>GCAGGACAGCAAGGACAGCACCTACAGCCTCAGCAGCACCCTGACGCT<br>GAGCAAAGCAGACTACGAGAAACACAAAGTCTACGCCTGCGAAGTCACC<br>CATCAGGGCCTGAGCTCGCCCGTCACAAAGAGCTTCAACAGGGGAGAG<br>TGTTAG |
| 11 | GACATCCAGATGACCCAGTCTCCATCCAGTCTGTCTGCATCCGTAGGAG<br>ACAGAGTCACCATCACTTGCCATGCCAGTCAGAACATTAATGTTTGGTTA<br>TCTTGGTACCAGCAGAAACCAGGAAAAGCCCCTAAACTCTTGATCTATAA<br>GGCTTCCAACTTGCACACAGGCGTCCCATCAAGATTTAGTGGCAGTGGA<br>TCTGGAACAGATTTCACATTCACCATCAGCAGCCTGCAGCCTGAAGACAT<br>TGCCACTTACTACTGTCAACAGGGTCAAACTTATCCATACACGTTCGGAC<br>AGGGGACCAAGCTGGAGATCAAACGAACTGTGGCTGCACCATCTGTCTT<br>CATCTTCCCGCCATCTGATGAGCAGTTGAAATCTGGAACTGCCTCTGTTG<br>TGTGCCTGCTGAATAACTTCTATCCCAGAGAGGCCAAAGTACAGTGGAA<br>GGTGGATAACGCCCTCCAATCGGGTAACTCCCAGGAGAGTGTCACAGA<br>GCAGGACAGCAAGGACAGCACCTACAGCCTCAGCAGCACCCTGACGCT<br>GAGCAAAGCAGACTACGAGAAACACAAAGTCTACGCCTGCGAAGTCACC<br>CATCAGGGCCTGAGCTCGCCCGTCACAAAGAGCTTCAACAGGGGAGAG<br>TGTTAG |
| 12 | RYYMY |
| 13 | EINPNNGGTKFNEKFKN |
| 14 | EDDYDGTPFAMDY |
| 15 | HASQNINVWLS |
| 16 | KASNLHT |
| 17 | QQGQTYPYT |
| 18 | MKMASFLAFLLLNFRVCLLLLQLLMPHSAQFSVLGPSGPILAMVGEDADLPC<br>HLFPTMSAETMELKWVSSSLRQVVNVYADGKEVEDRQSAPYRGRTSILRD<br>GITAGKAALRIHNVTASDSGKYLCYFQDGDFYEKALVELKVAALGSDLHVDV<br>KGYKDGGIHLECRSTGWYPQPQIQWSNNKGENIPTVEAPVVADGVGLYAV<br>AASVIMRGSSGEGVSCTIRSSLLGLEKTASISIADPFFRSAQRWIAALAGTLP<br>VLLLLLGGAGYFLWQQQEEKKTQFRKKKREQELREMAWSTMKQEQSTRVK<br>LLEELRWRSIQYASRGERHSAYNEWKKALFKPADVILDPKTANPILLVSEDQ<br>RSVQRAKEPQDLPDNPERFNWHYCVLGCESFISGRHYWEVEVGDRKEWHI<br>GVCSKNVQRKGWVKMTPENGFWTMGLTDGNKYRTLTEPRTNLKLPKPPKK<br>VGVFLDYETGDISFYNAVDGSHIHTFLDVSFSEALYPVFRILTLEPTALTICPA |
| 19 | MKMASSLAFLLLNFHVSLLLVQLLTPCSAQFSVLGPSGPILAMVGEDADLPC<br>HLFPTMSAETMELKWVSSSLRQVVNVYADGKEVEDRQSAPYRGRTSILRD<br>GITAGKAALRIHNVTASDSGKYLCYFQDGDFYEKALVELKVAALGSNLHVEV<br>KGYEDGGIHLECRSTGWYPQPQIQWSNAKGENIPAVEAPVVADGVGLYEV<br>AASVIMRGGSGEGVSCIIRNSLLGLEKTASISIADPFFRSAQPWIAALAGTLPI<br>LLLLLAGASYFLWRQQKEITALSSEIESEQEMKEMGYAATEREISLRESLQEE<br>LKRKKIQYLTRGEESSSDTNKSA |
| 20 | MKMASSLAFLLLNFHVSLFLVQLLTPCSAQFSVLGPSGPILAMVGEDADLPC<br>HLFPTMSAETMELRWVSSSLRQVVNVYADGKEVEDRQSAPYRGRTSILRD |

TABLE 8-continued

Brief description of useful amino acid and nucleotide sequences for practicing the invention

| SEQ ID NO: | Describes the amino acid or nucleotide sequence below: |
|---|---|
| | GITAGKAALRIHNVTASDSGKYLCYFQDGDFYEKALVELKVAALGSDLHIEVK GYEDGGIHLECRSTGWYPQPQIKWSDTKGENIPAVEAPVVADGVGLYAVAA SVIMRGSSGGGVSCIIRNSLLGLEKTASISIADPFFRSAQPWIAALAGTLPISLL LLAGASYFLWRQQKEKIALSRETEREREMKEMGYAATEQEISLREKLQEELK WRKIQYMARGEKSLAYHEWKMALFKPADVILDPDTANAILLVSEDQRSVQR AEEPRDLPDNPERFEWRYCVLGCENFTSGRHYWEVEVGDRKEWHIGVCS KNVERKKGWVKMTPENGYWTMGLTDGNKYRALTEPRTNLKLPEPPRKVGI FLDYETGEISFYNATDGSHIYTFPHASFSEPLYPVFRILTLEPTALTICPIPKEV ESSPDPDLVPDHSLETPLTPGLANESGEPQAEVTSLLLPAHPGAEVSPSATT NQNHKLQARTEALY |
| 21 | MGSSLAFLLLSFHVCVLLLQLLMPHSAQFAVVGPPGPILAMVGEDADLPCHL FPTMSAETMELRWVSSNLRQVVNVYADGKEVEDRQSAAYRGRTSILRDGIT AGKAALRIHNVTASDSGKYLCYFQDGDFYEKALVELKVAALGSDLHIDVKGY EDGGIHLECRSTGWYPQPQIRWSNDKGENIPAVEAPVFVDGVGLYAVAASV ILRGSSGEGVSCTIRSSLLGLEKTTSISIAG HHHHHH |
| 22 | MGSSLAFLLLNFHVSFFLVQLLTPCSAQFSVLGPSGPILAMVGEDADLPCHL FPTMSAETMELRWVSSSLRQVVNVYADGKEVEDRQSAPYRGRTSILRDDIA AGKAALRIHNVTASDSGKYLCYFQDADFYEKALVELKVAALGSNLHVEVKGY EDGGIHLECRSTGWYPQPKIQWSNAKGQNIPAVEAPVVADGVGLYAVAASV IMRGGSGESVSCIIRNSVLGLEKTASISIAD HHHHHH |
| 23 | MANFLAFLLLNFRVCLLLVQLLTPCSAQFAVLGPHGPILAMVGEDVDLPCHL FPTMSAETMELRWVSSSLRQVVNVYSDGKEVEDRQSAPYRGRTSILRDGIT AGKAALRIHNVTASDSGKYLCYFQDGDFYEKALVELKVAALGSDLHIEVKGY EDGGIHLECRSTGWYPQPQIQWSNTKGQHIPAVKAPVVADGVGLYAVAASV IMRGSSGEGVSCIIRNSLLGLEKTASISITD HHHHHH |

Developability Properties of the 6 Humanized Variants

1. Generation of Cell Lines a. Expression Vector Construction

The gene sequences encoding the heavy chains and light chains were cloned into the vector. The gene system was used to express the antibodies in CHO cells. Antibodies expression was under the control of the EF1 alpha promoter. The expression vectors bear unique genetic elements that shield the transgene from the silencing effects of surrounding chromatin (Girod et al., 2007). Transcription is maintained at a maximum level and is independent of the transgene integration site, resulting in stable and high-level protein expression.

b. Cell Lines Development

The CHO host cell line is derived from CHO-K1 CCL-61 cells from the American 124 Type Culture Collection (ATCC) and has been adapted to grow in suspension in the chemically defined BalanCD Growth A culture medium (Irvine Scientific). Cells were transfected by electroporation using the Neon transfection system (Invitrogen).

c. Single-Cell Cloning Using ClonePix FL Device.

The same medium (BalanCD Growth A, Irvine Scientific) was used as a basal medium for transfection, single-cell cloning, and production in order to keep the environment of the cells unchanged throughout the whole procedure. Following transfection of each vector, puromycin selection pressure was applied to generate the stable pools. Diluted cells were plated into semi-solid media (CloneMedia©; Molecular Devices) and plates were incubated at 37° C. with 5% $CO_2$, in a humidified incubator. Expanded colonies were picked using ClonePix™ FL Imager from Molecular Devices and transferred to 96-well plates, then expanded in first 24-well and then 6-well TC plates.

d. Fed-Batch Performance Evaluation

Growth and production performance of individual clones were evaluated in 125 ml shake flasks to select the best clones by the criteria of cell growth performance and productivity in a 10 day fed-batch process using Cell Boost7 A+7B feed (GE Healthcare, USA). Fed-batch cultures were initiated at cell concentrations of 0.3×10 6 cells/ml.

Results obtained for cell growth and productivity are summarized in Table 9.

2. Samples Preparation for Manufacturability Assessment

Each candidate antibody was purified by protein A capture from clarified CHO cell supernatant pools: two pools were required for each variant to ensure sufficient material for testing. The protein concentration was determined for all post-capture samples by UV method. Sample recovery and yields were greater than 80% for the majority of samples and all variants showed similar yields. Each antibody was then buffer-exchanged into 25 mM Histidine, 125 mM NaCl, pH 6.0 using 30 kDa MWCO centrifugal filter units until the flow-through material reached the target pH for the formulation. During the exchange step, there were no indicators of protein precipitation or slowed flow during the exchange for any of the variants. After buffer exchange completion, the concentration of each variant sample was adjusted to 1.0 mg/mL with formulation buffer, and 10% PS-80 was added to a final concentration of 0.02% PS-80.

3. Thermal Stability Assessment

Differential scanning fluorimetry analysis was performed to assess and compare the thermal stabilities of tested antibody variant. Each variant was analyzed in triplicate and the mean $T_{onset}$, $T_{agg}$ and $T_m$ determined for each observed thermal transition (data not shown).

No significant differences were observed between $T_{onset}$ and $T_m$ values obtained for all tested variants. The determined $T_{m1}$ value for all antibodies was 61° C., and the values determined for $T_{onset}$ were 54 to 55° C. for all antibodies.

The Ta gg values determined based on the plots for colloidal stability ranged from 71 to 78° C.

Overall, all 4 selected variants demonstrate comparable thermal stability: variations observed do not lead to significant changes in thermal stability between tested antibodies.

4. Forced Degradation Studies a. Agitation

Samples for each variant were subjected to agitation stress on an orbital shaker set to 500 rpm at room temperature. One sample for each variant was agitated for 24 and another sample for 48 hours. One vial of each variant was stored at room temperature for up to 48 hours as a control. No changes in appearance were observed for agitated samples compared to controls: all samples were observed to be clear, colorless and free of visible particulates (data not shown). In addition, there was no significant change in total protein content as determined by UV method (data not shown).

The effects of agitation stress on the stability of the panel of variants were evaluated by SEC, reduced CGE, non-reduced CGE, and icIEF methods (data not shown). No significant changes in the stability of the tested antibodies nor discernible trends over time in the accumulation of degradants were observed between the agitation control samples stored at room temperature and the agitation stress samples. The % main peak determined in SEC analysis was a 99.2% for all control and agitation samples. In R-CGE analysis the % main peak was 98.5% for all control and agitation samples. NR-CGE analysis revealed no significant trends or changes in % main peak between the controls and stressed samples. In conclusion, no significant differences in stability were observed between all candidate variants.

b. Freeze-Thaw Stress

Three samples of each candidate were aliquoted into Eppendorf tubes, and subjected to freeze-thaw stress. Samples were stored at −75±10° C. and then thawed at room temperature. One sample for each candidate was subjected to 3 freeze-thaw cycles; another to 6 freeze-thaw cycles; and a third sample to 10 cycles. All stressed samples were observed to be clear, colorless and free of visible particulates (data not shown), and there was no significant change in total protein content as determined by UV method (data not shown).

The effects of freeze-thaw stress on the stability of the panel of variants were evaluated by SEC, reduced CGE, non-reduced CGE, and icIEF methods (data not shown). Freeze-thaw stress had no impact on the stability of the antibodies based on SEC, R-CGE and NR-CGE analysis.

The icIEF analysis revealed noticeable changes in charge heterogeneity of tested antibodies. The concentration of basic variants decreased at successive F/T cycles, with the lowest concentration of basic variants at 10X FIT cycles as compared to general controls. The only exception was variant IgG1 7.2 VH2/VK1, for which the decrease in concentration of basic variants was at the same level for all tested F/T cycles (see Table 9). In variants mAb1, mAb2, and mAb3, after 10X F/T cycles, the basic species decreased by 1.0, 1.3, and 3.4%, respectively. The decrease in the concentration of the basic species is related to an increase in the % of main peak. In variants mAb4, mAb5 and mAb6 the decrease in basic species is 4.8, 2.8 and 4.7%, respectively. The change in variant mAb4 is mostly related to an increase of % main peak, while the changes in variant mAb5 and mAb6 are related to increases in both the % main peak and in the % acidic variant.

Overall, it was determined that the highest resistance to changes from freeze-thaw stress was observed for variants mAb1 (IgG1 7.2 VH2NK1) and mAb2 (IgG1 7.2 VH2/VK2).

c. Acidic pH Stress

Samples for each candidate were subjected to acidic pH stress at room temperature: each sample was adjusted with HCl to pH 3.5 and kept at room temperature for 2 hours, 4 hours, and 24 hours after which samples were neutralized with 1 M Tris, pH 7.0. All samples were observed to be clear, colorless and free of visible particulates (data not shown), and there was no significant change in protein concentration as determined by UV method (data not shown).

The effects of acidic pH stress on the panel of variants were evaluated by SEC, reduced CGE, non-reduced CGE, and icIEF methods (data not shown). No significant changes in the accumulation of degradants were detected over time for samples exposed to low pH as compared to 48 hours RT control by either R-CGE or NR-CGE analysis. In the charge heterogeneity analysis, the concentration of basic variants decreased in all samples subjected to acidic pH stress, however, no clear trends were observed over time.

The overall lowest impact of acidic stress on the reduction of basic variants was observed for variants mAb1 (IgG1 7.2 VH2/VK1) and mAb2 (IgG1 7.2 VH2/VK2). This result is in good agreement with the results obtained by icIEF in freeze-thaw study. In the SEC analysis, all variants were observed to accumulate some aggregates upon exposure to acidic stress which was related to a decrease of the % main peak, however, no clear trends were observed over time. In general, the accumulation of aggregates was about 9 times greater for IgG4 variants as compared to the IgG1 variants. The accumulation of aggregates for IgG1 variants was 0.3 to 1.0% for all acidic stress samples, and for IgG4 variants the accumulation was 4.3 to 7.8% for stress samples, which is significantly higher (see Table 9).

In conclusion, it was determined that the highest resistance to acidic stress was observed for variants mAb1 (IgG1 7.2 VH2/VK1) and mAb2 (IgG1 7.2 VH2/VK2).

d. Heat Stress

Samples for each variant were subjected to heat stress in a heat block at 50° C. for 3 days, 1 week, and 2 weeks and then compared to the set of general control samples stored at 2-8° C. Appearance testing of the samples was performed periodically and there was no observed evidence of phase separation, change in opacity, or precipitation. All samples were observed to be clear, colorless and free of visible particulates for all timepoints (data not shown). In addition, there was no significant change in protein concentration as determined by UV method (data not shown).

The effects of heat stress on the panel of variants were evaluated by SEC, R-CGE, NR-CGE and icIEF methods. The results revealed that all variants were susceptible to heat stress.

In the SEC analysis, clear trends for increasing aggregate concentration were observed as a function of time for all tested variants. Significantly higher accumulation of aggregates was observed for IgG4 variants compared to IgG1. After two weeks, the increase of % total aggregates ranged from 33.7 to 44.7% for the IgG4 variants but only 13.0 to 18.2% for the IgG1 variants (see Table 9). Additionally, the mAb1 (IgG1 7.2 VH2/VK1) and mAb2 (IgG1 7.2 VH2/VK2) variants accumulated less aggregate than the control mAb3 (IgG1 20.1 VH3/VK1).

In the R-CGE analysis, clear trends for decreasing purity (defined as the decrease of the % of LC +HC) were observed as a function of time for all tested variants, however, there were no significant differences observed in the stability between them. The level of samples degradation was comparable for all tested antibodies (data not shown). Similarly, NR-CGE data revealed clear trends for decreasing purity (defined as the decrease of the main peak) as a function of time for all tested variants. Significantly lower purity was observed for IgG4 variants compared to IgG1 (data not shown). After two weeks the % purity was decreased by 34.8 to 41.7% for the IgG4 variants but only 20.0 to 30.0% for the IgG1 variants (data not shown). Additionally, mAb1 (IgG1 7.2 VH2/VK1) and mAb2 (IgG1 7.2 VH2/VK2) variants exhibited lower degradation than mAb3 IgG1 20.1 VH3/VK1. For the IgG1 antibodies, the reduction in main peak was primarily accompanied by an increase of front main peak impurities (fragments). For IgG4 antibodies, however, the accumulation of both front main peak impurities (fragments) and back main peak impurities (aggregates) were observed as a function of decreasing main peak (data not shown). This result is in good agreement with the SEC data where the significantly higher concentration of aggregates was observed for IgG4 antibodies compared to IgG1.

The 1-week samples for the IgG4 variants were too degraded for analysis by icIEF, and the 2-week samples for all variants were too degraded for analysis. Therefore, only 3 days data were used to evaluate changes in charge heterogeneity between tested antibodies.

The difference in purity as determined by % main peak was 12.4 to 14.4% difference for IgG1 samples and 16.0 to 16.6% for IgG4 samples (data not shown).

Overall, it was demonstrated that degradation upon heat stress was greater for IgG4 variants as compared to IgG1 variants, and this was observed at all time points. The analysis indicates that mAb1 (IgG1 7.2 VH2/VK1) and mAb2 (IgG1 7.2 VH2/VK2) variants are the least susceptible to heat stress and this result is consistent with data obtained for freeze-thaw and acidic pH stresses.

Selection of the Best Candidate in Terms of Developability Properties

Regarding the productivity in cell lines, the best results were obtained with the humanized variant mAb1 (7.2 VH2/VK1), with a viable cell density raising 54×10 6 viable cells/ml at 10 days for mAb1.

In the thermal stability study, samples were assessed in the standard matrix by DSF analysis to determine $T_{onset}$, $T_m$ and $T_{agg}$ for each candidate. No variation in $T_{onset}$ and T m 1 were observed, and $T_{agg}$ was greater than 70° C. for all variants. The results indicate that mAb1, mAb2, mAb4, and mAb5 demonstrate comparable thermal stability.

In the forced degradation study, samples were exposed to agitation, freeze-thaw, acidic pH and heat stresses. The results indicate that the panel of candidate variants were susceptible to degradation at varying extents under relevant stress conditions:

No significant response to agitation stress was observed by any of the analytical methods.

No significant response to freeze-thaw stress was observed by SEC or CGE methods, however icIEF analysis revealed differences in charge heterogeneity between tested variants and showed that mAb1 (IgG1 7.2 VH2/VK1) and mAb2 (IgG1 7.2 VH2/VK2) variants exhibited the highest resistance to changes caused by freeze-thaw stress.

A response to acidic pH stress was observed by icIEF and SEC, wherein all candidates accumulated some impurities upon exposure. The mAb1 (IgG1 7.2 VH2/VK1) and mAb2 (IgG1 7.2 VH2/VK2) variants exhibited the highest resistance to acidic pH stress.

The most significant stress response observed was to sample storage at 50° C. SEC, NR-CGE, and icIEF analyses revealed a significant trend of decreasing sample purity over time. The observed decrease in purity was consistently greater for IgG4 variants as compared to IgG1 variants. In the group of IgG1 variants, the mAb1 (7.2 VH2/VK1) and mAb2 (IgG1 7.2 VH2NK2) exhibited the highest resistance to acidic heat stress.

The results of the developability properties of the different humanized candidates are summarized in the Table 9 below:

TABLE 9 mAb1 humanized candidate has higher developability properties as compared to all other tested humanized variants

| Name | Candidate | Pool growth (viable cell density at 10 days/ ml) and productivity (µg/ml) | Freeze-thaw stress - Decrease of % basic variants[1] (3 cycles, 6 cycles and 10 cycles) | Acidic Stress - SEC analysis (increase in % aggregates at pH 3.5 after 24 h) | Heat Stress - SEC analysis (Difference in % Agg as measured by SEC analysis after 2 weeks at 50° C.) |
|---|---|---|---|---|---|
| mAb1 | 7.2 VH2/VK1 IgG1 | 54 × 10⁶ 550 µg/ml | 1.2 1.2 1.0 | 0.2 | 13.9 |
| mAb2 | 7.2 VH2/VK2 IgG1 | 30 × 10⁶ 330 µg/ml | 0.9 0.6 1.3 | 0.8 | 13.1 |
| mAb3 | 20.1 VH3/VK1 IgG1 | n.d | 2.1 2.0 3.4 | 0.3 | 18.3 |
| mAb4 | 7.2 VH2/VK1 IgG4 | 44 × 10⁶ 780 µg/ml | 1.9 1.9 3.0 | 4.4 | 33.6 |
| mAb5 | 7.2 VH2/VK2 IgG4 | 39 × 10⁶ 475 µg/ml | 1.6 1.8 2.8 | 5.1 | 35.4 |
| mAb6 | 20.1 VH3/VK1 IgG4 | 38 × 10⁶ 430 µg/ml | 2.5 2.4 4.7 | 6.3 | 44.6 |

[1]Change in % Basic Variants was calculated based on non-rounded results, subtracting the % basic variants of the stressed samples from that of the respective control sample.

As a conclusion, mAb1 variant showed the best results in terms of developability and was selected as the lead candidate.

Functional properties of humanized mAb 7.2 variants as monovalent and bivalent molecules 1. Preparation of Fab and Fab$_2$ fragments a. Pepsin digestion for F(ab')$_2$ generation Immobilized pepsin in 50% slurry (Thermo Scientific kit, Cat. N°44988) was buffer-exchanged into digestion buffer (20 mM Sodium acetate pH 4.4) by spinning down the slurry at 5000 g 2 min. The supernatant was discarded and slurry resuspended in 1 mL digestion buffer followed by another spin at 5000 g 2 min. This step was repeated additional four times (five resin washes in total). The resin was then resuspended in digestion buffer up to the original slurry volume. mAb 4, mAb 5 and mAb 6 (7.2 VH2/VK1, 7.2 VH2/VK2 or 20.1 VH3/VK1 IgG4 variants) were buffer-exchanged into digestion buffer using 5 or 10 mL Zeba Spin column (scale dependent) and concentrated to 3 mg/mL using Vivaspin concentrator (10,000 MWCO) according to manufacturer protocol. mAbs 4, 5 and 6 at 3 mg/mL (previously buffer exchanged in digestion buffer) were mixed with pepsin immobilized on resin and incubated at 37° C. rotating, 1.5-2 hours. Digestion mixtures were spin down at 5000 g 2 min. The supernatants were removed and filtered into a fresh tube using an appropriate syringe and 0.22 µm small filter (Merck Millipore, Millex Cat n° SLGV004SL). The resins were washed with 1 mL PBS, spin at 5000 g 1 min. The supernatants were removed, filtered and pooled with previous supernatants. The wash step was repeated.

Digested and filtered supernatants were purified using HiLoad 16/600 200 pg size exclusion column using 10 mM Sodium acetate, 100 mM NaCl, pH 5.5 as a mobile phase. The fractions corresponding to eluted F(ab')2 fragment are pooled, concentrated and sterile filtered.

F(ab')2 fragments were analyzed by SDS-PAGE, analytical SEC and OD$_{280nm}$ reading.

b. Papain Digestion for Fab Generation

Immobilized papain in 50% slurry (Thermo Scientific kit, Cat. N° 20341) was buffer-exchanged into digestion buffer (20 mM Sodium Phosphate, 10 mM EDTA, 150 mM Cysteine pH 7.0) by spinning down the slurry at 5000 g 2 min. The supernatant was discarded and slurry resuspended in larger volume of digestion buffer followed by another spin at 5000 g 2 min. This step was repeated additional four times (five resin washes in total). The resin was then resuspended in digestion buffer up to the original slurry volume. mAb 4, mAb 5 and mAb 6 (7.2 VH2/VK1, 7.2 VH2/VK2 or 20.1 VH3/VK1 IgG4 variants) were buffer-exchanged into digestion buffer using 5 or 10 mL Zeba Spin column (scale dependent) and concentrated to 3 mg/mL using Vivaspin concentrator (10,000 MWCO) according to manufacturer protocol.

mAbs 4, 5 and 6 at 3 mg/mL (previously buffer exchanged in digestion buffer) were mixed with papain immobilized on resin and incubated at 37° C. rotating, 42 hours.

Digestion mixtures were spin down at 5000 g 2 min. The supernatants were removed and filtered into a fresh tube using an appropriate syringe and 0.22 µm small filter (Merck Millipore, Millex Cat n° SLGV004SL). The resins were washed three times with PBS, spin at 5000 g 1 min, collecting and pooling at each cycle the supernatant. Pooled fractions were then filtered into a fresh tube using an appropriate syringe and 0.22 µm small filter. Digested and filtered supernatants were first buffer-exchanged into 1xDPBS, pH 7.4, then first purified using protein A column to remove Fc and undigested mAbs, followed by polishing step using size-exclusion (SEC) column with 10 mM sodium acetate, 100 mM NaCl, pH 5.5 as a mobile phase. The fractions corresponding to eluted Fab fragments were pooled, concentrated and sterile filtered.

Fab fragments were analyzed by SDS-PAGE, analytical SEC and OD$_{280nm}$ reading.

2. Affinity Measurement of Humanized 7.2 and 20.1 Fab, F(Ab')2 Fragments and IgG Format Using Biacore In order to assess the affinity of lead humanized 7.2 and 20.1 antibodies for BTN3A1 in their different formats (Fab, F(ab')2 and IgG), single cycle kinetic analysis was performed using a Biacore T200 (Ser. No. 1909913) instrument running Biacore T200 Control software V2.0.1 and Evaluation software V3.0 (GE Healthcare, Uppsala, Sweden). All single cycle kinetic experiments were run at 25° C. with HBS-P+ running buffer (pH 7.4) containing 0.1% BSA (GE Healthcare, Little Chalfont, UK).

BTN3A1 His-tagged antigen (Sino Biological, Beijing, China) was diluted in running buffer to a final concentration of 0.4 pg/ml. At the start of each cycle, BTN3A1-His was captured onto Fc2 of CM5 sensor chip pre-coupled using a His capture kit (GE Healthcare, Little Chalfont, UK) with standard amine chemistry at a flow rate of 10 µl/min. An immobilization level (RL) of ~34 RU, 16 RU or 11 RU, the different theoretical values to obtain a RMax of ~50 RU was used for the analytes Fab, F(ab')2 and IgG respectively. The surface was then allowed to stabilize. Single cycle kinetic data was obtained with the purified samples (Fab, F(ab')2 and IgG) at a flow rate of 40 µl/min to minimize any potential mass transfer effects. The signal from the reference channel Fc1 (no antigen capture) was subtracted from that of Fc2 to correct for differences in non-specific binding to the reference surface. The signal for BTN3A1-His blank runs (no analyte) were subtracted to correct for differences in surface stability. The association phase for the five injections of increasing concentrations was monitored for 240 seconds each time and a single dissociation phase was measured for 1400 seconds following the last injection of analyte. Regeneration of the chip surface was conducted using two injections of 10 mM glycine-HCL pH 1.5 followed by a stabilization period of 240 seconds. Raw sensorgrams were fitted with a 1:1 model for Fab samples and with a bivalent analyte model for F(ab')2 and IgG samples in agreement with the different valences of the analytes. The kinetic constants were calculated for each variant (see Tables 10, 11 and 12).

TABLE 10

Single cycle kinetic IgG analysis
IgG (bivalent fitting)

| Sample | $K_a1$ (1/Ms) | $K_a2$ (1/Ms) | $K_d 1$ (1/s) | $K_d 2$ (1/s) | $R_{max}$ (RU) | Chi$^2$ (RU$^2$) |
|---|---|---|---|---|---|---|
| mAb 1 (7.2 VH2/VK1) | $5.30 \times 10^4$ | 4.21 | $4.63 \times 10^{-4}$ | $4.40 \times 10^1$ | 69.6 | 0.063 |
| mAb 2 (7.2 VH2/VK2) | $5.97 \times 10^4$ | $2.01 \times 10^{-3}$ | $4.03 \times 10^{-4}$ | $2.41 \times 10^{-2}$ | 68.0 | 0.144 |
| mAb 3 (20.1 VH3/VK1) | $5.63 \times 10^4$ | $5.47 \times 10^{-5}$ | $3.79 \times 10^{-3}$ | $8.60 \times 10^{-5}$ | 56.1 | 0.042 |

TABLE 11

Single cycle kinetic F(ab')$_2$ analysis
F(ab')$_2$ (bivalent fitting)

| Sample | $K_a 1$ (1/Ms) | $K_a 2$ (1/Ms) | $K_d 1$ (1/s) | $K_d 2$ (1/s) | $R_{max}$ (RU) | Chi$^2$ (RU$^2$) |
|---|---|---|---|---|---|---|
| 7.2 VH2/VK1 F(ab')$_2$ | $8.33 \times 10^4$ | 6.10 | $6.66 \times 10^{-4}$ | $3.24 \times 10^1$ | 78.2 | 0.033 |
| 7.2 VH2/VK2 F(ab')$_2$ | $1.46 \times 10^5$ | 3.40 | $3.94 \times 10^{-4}$ | $5.46 \times 10^1$ | 58.9 | 0.126 |
| 20.1 VH3/VK1 F(ab')$_2$ | $9.23 \times 10^4$ | $5.03 \times 10^{-5}$ | $4.16 \times 10^{-3}$ | $8.10 \times 10^{-5}$ | 61.5 | 0.326 |

TABLE 12

Single cycle kinetic Fab analysis
Fab (1:1 fitting)

| Sample | $K_a$ (1/Ms) | $K_d$ (1/S) | $K_D$ (nM) | $R_{max}$ (RU) | Chi$^2$ (RU$^2$) |
|---|---|---|---|---|---|
| 7.2 VH2/VK1 Fab | $1.98 \times 10^5$ | $6.39 \times 10^{-4}$ | 3.22 | 66 | 0.114 |
| 7.2 VH2/VK2 Fab | $2.22 \times 10^5$ | $6.69 \times 10^{-4}$ | 3.01 | 61 | 0.091 |
| 20.1 VH3/VK1 Fab | $1.76 \times 10^6$ | $3.57 \times 10^{-2}$ | 20.30 | 55 | 1.330 |

3. Selection of the Best Candidate in Terms of Affinity Properties 20.1 and 7.2 humanized variants showed significant differences in terms of affinity properties. These differences can be observed with IgG and F(ab')2 formats, but the gap is even higher with Fab fragments: indeed, 20.1 showed a mean $K_D$ of 20.30 nM while 7.2 showed a mean $K_D$ of 3.22 (VH2/VK1) or 3.01 (VH2/VK2).

4. mAb 1 Binding Avidity to Primary T Cells and Other Cell Lines

Next, mAb1 binding avidity has been evaluated by flow cytometry on human primary T cells as well as on various cell lines including WT and BTN3A knock-out reconstituted with BTN3A1, BTN3A2 or BTN3A3 isoforms individually (Data not shown). $EC_{50}$ values obtained for each tested cell type are summarized in Table 13.

Data obtained in BTN3A KO cells clearly indicated that mAb1 binds specifically to its target. In addition, reconstitution with individual isoforms confirmed that mAb1 recognizes BTN3A1, BTN3A2, and BTN3A3 with comparable avidity. All other tested cells appeared positive for mAb1 binding with a range of $EC_{50}$ values going from 9.6 nM for Burkitt's lymphoma Daudi cell line to 112.3 nM for colorectal adenocarcinoma cell line HT29.

TABLE 13 mAb1 Binding Avidity on Human Cells.

| Cells | Description | Gating | $EC_{50}$ µg/mL (+/−sem) | $EC_{50}$ (×10$^{-9}$M) (+/−sem) |
|---|---|---|---|---|
| Human HV PBMC | Primary (n = 6) | CD3+ | 5.25 (+/−0.57) | 34.9 (+/−3.8) |
| Daudi | Burkitt's lymphoma (n = 5) | NA | 1.44 (+/−0.16) | 9.6 (+/−1.04) |
| L-IPC (PDAC087T) | Pancreatic Ductal Adenocarcinoma (n = 4) | NA | 26.26 (+/−4.4) | 175.1 (+/−29.3) |
| HT29 | Colorectal adenocarcinoma (n = 3) | NA | 16.84 (+/−3.1) | 112.3 (+/−20.6) |

TABLE 13-continued mAb1 Binding Avidity on Human Cells.

| Cells | Description | Gating | EC$_{50}$ µg/mL (+/−sem) | EC$_{50}$ (×10$^{-9}$M) (+/−sem) |
|---|---|---|---|---|
| A549 | Lung carcinoma (n = 6) | NA | 6.53 (+/−1.8) | 43.56 (+/−12.3) |
| HUVEC | Endothelial (n = 2) | NA | 12.8 (+/−1.98) | 85.2 (+/−13.2) |
| HEK293T WT | Embryonic kidney (n = 3) | NA | 6.2 (+/−0.44) | 41.3 (+/−2.95) |
| HEK293T BTN3KO | Embryonic kidney; Full Knock-out for BTN3A1, A2, A3 (n = 3) | NA | NA | NA |
| HEK293T BTN3KO + 3A1-CFP | Embryonic kidney; Full Knock-out for BTN3A1, A2, A3 transiently transfected with BTN3A1-CFP (n = 4) | CFP+ | 2.4 (+/−0.34) | 15.9 (+/−2.3) |
| HEK293T BTN3KO + 3A2-CFP | Embryonic kidney; Full Knock-out for BTN3A1, A2, A3 transiently transfected with BTN3A2-CFP (n = 5) | CFP+ | 1.88 (+/−0.39) | 12.5 (+/−2.6) |
| HEK293T BTN3KO + 3A3-CFP | Embryonic kidney; Full Knock-out for BTN3A1, A2, A3 transiently transfected with BTN3A3-CFP (n = 5) | CFP+ | 1.75 (+/−0.11) | 11.68 (+/−0.72) |

NA: Not applicable 5. mAb1 has no off-target binding

The potential for off-target binding of mAb1 on other non-BTN3A molecules was assessed by the Retrogenix technology. This work aimed to demonstrate the absence of off-target binding by screening a cell array expressing >5000 human membrane receptors or secreted proteins expressed at the surface of HEK293 cells (Retrogenix platform).

Investigation of the level of binding of mAb1 to untransfected HEK293 cells, and to cells over-expressing BTN3A1, before or after cell fixation, showed 5 µg/ml on fixed cells to be a suitable screening condition. Under this condition, mAb1 was screened for binding against human HEK293 cells, individually expressing 5528 human proteins, comprising of cell surface membrane proteins, and cell surface-tethered secreted proteins. This revealed ten primary hits.

Each primary hit was re-expressed, along with two control receptors (CD20 and EGFR), and re-tested with 5 µg/ml of mAb1, 5 µg/ml of an isotype control antibody, and other positive and negative control treatments. After removing five non-specific hits, there remained five specific interactions for the test antibody. All 5 specific hits were BTN3A related; two isoforms of BTN3A1, two isoforms of BTN3A2 and one isoform of BTN3A3.

The study conclusions are that, no off-target interactions for mAb1 were identified, indicating high specificity of mAb1 for its BTN3A epitope.

6. mAb1 Mediates VT9Vδ2 T Cell Activation and Tumour Cell Killing

Originally, mouse anti-BTN3A mAbs were shown to trigger BTN3A recognition by Vγ9Vδ2 T cells, mediating activation leading to (i) proliferation of this specific subset in human PBMCs, (ii) production of cytokines (IFNγ and TNFα), and (iii) the cytolysis of infected or transformed target cells (e.g., By Perforin, granzymes, TRAIL) (Harly et al, Blood, 2012 & Benyamine, A. et al. 2016, Oncoimmunology 5, e1146843).

Without being bound by any particular theory, a proposed mechanism of action of mAb1 is that its binding to BTN3A expressed at the surface of a tumour target cell triggers a conformational change that allows its signalling to its counter-receptor on Vγ9Vδ2 T cells. The activity of anti-BTN3A antibodies is routinely assessed using an in vitro assay based on co-culture of a tumour cell line (the target) with primary human Vγ9Vδ2 T cells (the effector) previously expanded from PBMCs of healthy donors for 10 to 14 days, in presence of rHuIL-2 (200UI/mL) and aminobisphosphonates (Zometa, 1 µM). At the end of the expansion phase, the purity of Vγ9Vδ2 T cells is assessed by flow cytometry, and these cells are then frozen for future use. The day before the experiment, expanded Vγ9Vδ2 T cells are thawed and cultured overnight with 200 Ul/mL rHuIL-2 to maintain in vitro survival. After co-culture, Vγ9Vδ2 T cell activation is monitored either by flow cytometry detection of CD107a/b expression on γδ T cells, or by quantifying Caspase3/7 activation, as a measure of target cell killing.

First, human Vγ9Vδ2 T cells expanded from 3 different healthy donors PBMCs were co-cultured with the Daudi cell line (ATCC-CCL213; Burkitt's lymphoma) with increasing concentrations of mAb1. After 4 hours, cells were analysed for Vγ9Vδ2 T cell expression of CD107a/b by flow cytometry. Results showed a concentration related increase in the percentage of Vγ9Vδ2 T cells expressing CD107a/b, with a mean EC$_{50}$ of 0.89 nM (+/−0.39) (1A). In parallel, we assessed Vγ9Vδ2 T cell cytolytic activity against mAb1-pulsed Daudi cells. As shown in 1B, mAb1 induced target-cell apoptosis in a concentration dependent manner with an EC$_{50}$ of 0.35 nM. Additionally, Vγ9Vδ2 T cell activation (CD107a/b; 1C top panel) and tumour cell lysis (Casp3/7; 1C bottom panel) were tested using tumour cell lines from different tissue origins and compared to Daudi cells. Results showed that Vγ9Vδ2 T cells activation, and subsequent tumour cell lysis, were induced by mAb1 binding to L-IPC (Pancreatic Ductal Adenocarcinoma), A549 (Lung carcinoma epithelial cells) and HT29 (Colorectal adenocarcinoma) cell lines.

7. mAb1 Enhances 1/7 9Vδ2 T-Cell Killing of a Wide Array of BTN3A Expressing Human Cell Lines, Irrespective of their Tissue Origin a. Material & Methods.

Tumoral Cell Culture

HL-60 are human promyeloblast cell line derived from acute promyelocytic leukemia. Daudi is a human B lymphoblastic cell line derived from Burkitt' lymphoma. Jurkat is an acute T cells leukemia cell line.

HT-29 and HCT116 are human epithelial cells derived from colorectal adenocarcinoma.

PC3 and DU145 were derived from prostate carcinoma (metastatic site, bone and brain respectively).

SUM159 and MDA-MB-231 are triple negative breast cancer (TNBC) cell lines.

HL60, Daudi, Jurkat, DU145 and MDA-MB-231 cells were cultured in RPM! Glutamax, 10% FBS; 1 mM Sodium Pyruvate at 37° C./5% $CO_2$. PC3 and HT-29 were cultured in DMEM 10% FBS, 1 mM Sodium Pyruvate at 37° C./5% $CO_2$. HCT116 were cultured in McCoy 5a medium 10% SVF. SUM159 were cultured in medium F12 Nut Mix 1X+Glutamax, 5% SVF, Hydrocortisone 2 mg/ml, Insulin humalog 2 mg/ml and Non-Essential-Amino-Acids.

In vitro 1.491.452 T-cells expansion.

Peripheral blood mononuclear cells (PBMCs) were isolated by Ficoll density gradient centrifugation of peripheral blood obtained from the Etablissement Francais du Sang Provence Alpes Cote d'Azur (France). To expand Vγ9Vδ2 T cells, 50.106 PBMCs were resuspended at 1.5x106 cells/ml in RPMI1640 supplemented with 10% FBS and 1% sodium pyruvate in 75 cm2 flasks for 10 to 14 days, in presence of rHuIL-2 (200UI/mL) and aminobisphosphonates (Zoledronate, 1 μM). From day 5, rHuIL-2 was renewed every 2 or 3 days and cells were kept at 1x106/ml. At the end of the expansion phase, the purity of Vγ9Vδ2 T cells was assessed by flow cytometry, and if the number of Vγ9Vδ2 T cells reached 80% of live cells, these cells were then frozen in FBS 20% DMSO for future use.

Vγ9Vδ2 T-cell purification from human PBMC.

Fresh human PBMC were resuspend at 50.106 cells/ml in PBS+2% FBS+1 mM EDTA. Vg9Vd2 were isolated using EasySep™ Human Gamma/Delta T Cell Isolation Kit (Stemcell #19255) according to manufacturer instructions. At the end of the procedure, cell purity was measured by flow cytometry. Live CD3+Vγ9+ cells were more than 80%.

Vγ9Vδ2 T-Cells Killing Assay.

10 000 expanded or fresh Vγ9Vδ2 T-cells were co-cultured with tumoral cell lines in 96 well plates at indicated ratio (E:T 1:1 or 1:5) in RPMI 1640+glutamax, 10% FBS+1 mM NaPy in presence of mAb1 or relevant isotype control. When added to the co-culture rHuIL-2 was used at 20 IU/ml.

After indicated time, ATP was measured using the Glo reagent (Promega #G7572) that generates a luminescent signal proportional to the number of live cells.

b. Results

In addition to a method based on caspase 3/7 staining of target cells to monitor killing upon co-culture with Vγ9Vδ2 T-cells, we developed a complementary approach based on assessment of the number of viable cells in culture based on quantitation of the ATP present, an indicator of metabolically active cells.

With this assay, we monitored survival of the acute myeloid leukemia cell line HL60-WT, or -BTN3A-KO, 24 hrs after co-culture with expanded Vγ9Vδ2 T-cells (ratio E:T 1:1) in the presence of mAb1 or relevant isotype control+/− rHu IL-2 (20 IU/ml) Figure A). Results showed a concentration dependent decrease of HL60-WT survival in the presence of mAb1, indicative of an efficient BTN3A dependent killing of target tumor cell by activated Vγ9Vδ2 T-cells. Similar experiments were performed with in-vitro expanded, or freshly isolated Vγ9Vδ2 T-cells ( Figure B and C respectively), and cell viability was measured over a 4 day period. Figure B showed that in-vitro expanded Vγ9Vδ2 T-cells controlled HL60-WT proliferation in a concentration dependent manner. Addition of rHu-IL2 improve the effector cell killing capacity over time, likely by providing survival signals required for in-vitro culture of primary T-cells. Similar results were obtained with fresh Vγ9Vδ2 T-cells isolated from human PBMC, co-cultured for 4 days with HL60-WT at E:T ratio of 1:1 and 1:5. These results are indicative of the capacity of individual Vγ9Vδ2 T-cells to repeatedly engage and kill multiple tumor targets upon mAb1-mediated activation (

FIG. 2C).

Next, we used this assay to monitor mAb1-mediated Vγ9Vδ2 T-cells killing activity against BTN3A expressing cell lines from different tissues origin (Colon, breast, prostate, T lymphoma and Burkitt's lymphoma). HT29, PC3, DU145, MDA-MB-231, HCT116, SUM159, Jurkat and Daudi cells were co-cultured over-night with in-vitro expanded Vγ9Vδ2 T-cells in presence of increasing concentration of mAb1 and cell viability was measured. Results confirmed that mAb1 enhanced Vγ9Vδ2 T-cell killing of a wide array of BTN3A expressing human cell lines, irrespective of their tissue origin.

TABLE 15

10,000 Tumoral cells were co-cultured 24 hrs with in-vitro expanded Vγ9Vδ2 T-cells (ratio E:T 1:1) in presence of different concentration of mAb1. Cell viability was measured using bioluminescent assay detecting ATP levels. Bioluminescence values ×$10^5$ are indicated.

| Tumoral cell line | Tissues origin | No mAb | | mAb1 0.1 ug/ml | | mAb1 1 ug/ml | | mAb1 10 ug/ml | |
|---|---|---|---|---|---|---|---|---|---|
| | | Donor A | Donor B | Donor A | Donor B | Donor A | Donor B | Donor A | Donor B |
| HT29 | Colon | 68.0 | 55.1 | 67.6 | 58.1 | 54.2 | 49.2 | 41.0 | 40.0 |
| PC3 | Prostate | 86.2 | 73.5 | 83.3 | 68.5 | 48.6 | 49.7 | 36.8 | 38.0 |
| DU145 | Prostate | 75.7 | 69.6 | 65.1 | 64.4 | 33.6 | 41.8 | 22.1 | 26.8 |
| MDA-MB-231 | Breast | 66.5 | 59.8 | 68.2 | 59.8 | 57.6 | 54.7 | 43.4 | 44.4 |
| HCT116 | Colon | 114.1 | 102.7 | 102.9 | 96.3 | 63.6 | 68.3 | 53.4 | 59.4 |
| SUM159 | Breast | 84.7 | 90.8 | 54.1 | 58.5 | 20.7 | 25.2 | 16.4 | 19.2 |
| Jurkat | T lymphoma | 26.8 | 26.4 | 3.7 | 4.1 | 2.6 | 9.7 | 4.1 | 1.6 |
| Daudi | Burkitt's lymphoma | 17.3 | 9.7 | 6.2 | 5.0 | 7.2 | 5.3 | 6.0 | 6.1 |

8. mAb1 Improves Vγ9V52 T Cell Therapy in a Mouse Model Engrafted with Human AML Cell Lines.

As mAb1 target BTN3A is not expressed in rodents, and the Vγ9Vδ2 T cell sub-population is specific to primates, experimental proof of concept of Vγ9Vδ2 T cell anti-tumoral activity is usually tested in immunocompromised NSG mice engrafted with human tumour cell lines which express BTN3A, and adoptively transferred with Vγ9Vδ2 T cells from health human donors (the Vγ9Vδ2 T cells in such reconstitutions are allogenic to the tumour cell line). These models have been widely used to validate the anti-tumoral therapeutic potential of Vγ9Vδ2 T cells in a broad range of solid, as well as haematological, malignancies (Pauza, C. D. et al. 2018, Immunol. 9).

In addition, the murine anti-human BTN3A antibody, m20.1, administered to mice which had received human Vγ9Vδ2 T cells, was described to enhance animal survival, and decrease the leukemic burden, in blood and bone marrow of AML bearing NSG mice (benyamine et al 2016, see above). In this model, m20.1 was injected in combination with RLI, an rHuIL-15/IL-15Ra fusion protein that was shown to expand antitumor lymphocyte subsets, and to improve their survival in mice, leading to better anti-tumour activity of the transferred human Vγ9Vδ2 T cells.

For further characterisation of the efficacy of mAb1 in in vivo mouse models, we investigated the potential of human Vγ9Vδ2 T cells transfer combined with mAb1 to delay tumour growth and improve animal survival in AML bearing NSG mice.

a. U937 Model.

Healthy 6-8-weeks-old female mice (n=30) received 0.2x10 6 luciferase transduced-U937 cells on Day 0, as described in Gertner-Dardenne, J. et al. 2012. J. Immunol. 188, 4701-4708. At day 1, tumoral load was evaluated using bioluminescent imaging and mice were randomly assigned in six groups to receive intravenous injections of in-vitro expended human vγ9vδ2 T cells on Day 1 (3x10 6 cells) alone or combined to anti-BTN3A mAb1 or relevant isotype control (10 mg/kg, 200 ug/mice). Treatment was repeated at day 7. In group 2 and 4 antibodies were also administered at day 4 and 10. As complexes of rHuIL-15/rHulL15-Ra allows the proliferation of Vγ9Vδ2 T cells (J. Immunol. (2006) 177, 6072-608), these complexes were administered together with Vγ9Vδ2T cells.

All Groups are Described in Table 16.

The hIL-15/IL-15R-Fc complexes were pre-complexed at room temperature (RT) for 30 minutes before injection (0.2 ug hIL-15+1.2 ug IL-15R-Fc per mice) and mixed with Vγ9Vδ2 T cells prior injection. The final volume for each injection was 100 μl. Treatment mAbs were injected 4 hours prior to Vγ9Vδ2 T cell engraftment.

Our Results Confirmed that Vγ9Vδ2 T Cells Plus-Rhuil-15/Rhull.15-Ra Infusion Decrease the Tumour Burden. This Effect was Even More Striking and was Associated with a Significant Increase of Survival when Anti-BTN3A mAb1 was Added Along with Vγ9Vδ2 T Cells (Table 16 and 17 Table). Importantly, Cytarabine (Ara-C), one of the most effective drugs for the treatment of acute myeloid leukemia, used in this very aggressive mouse model (10 mg/kg in NSG mice bearing U937 tumour) improved mice survival for 2 to 3 days (~10%), as observed with mAb1 combine to human Vγ9Vδ2 T cell transfer.

These data highlight the potent anti-leukemic effect exerted by anti-BTN3A mAb combined to Vγ9V52 T cells immunotherapy in vivo.

TABLE 16

U937 AML mice model: group description.

| Group | Day 1 | Day 4 | Day 7 | Day 10 |
|---|---|---|---|---|
| 1 | No | No | No | No |
| 2 | Vγ9Vδ2 T cells (3 × 106 cells) + IL-15a + hIgG1 (10 mg/kg) | hIgG1 (10 mg/kg) | Vγ9Vδ2 T cells (3 × 106 cells) + IL-15a + hIgG1 (10 mg/kg) | hIgG1 (10 mg/kg) |
| 3 | Vγ9Vδ2 T cells (3 × 106 cells) + IL-15a + mAb1 (10 mg/kg) | No | Vγ9Vδ2 T cells (3 × 106 cells) + IL-15a + mAb1 (10 mg/kg) | No |
| 4 | Vγ9Vδ2 T cells (3 × 106 cells) + IL-15a + mAb1 (10 mg/kg) | mAb1 (10 mg/kg) | Vγ9Vδ2 T cells (3 × 106 cells) + IL-15a + mAb1 (10 mg/kg) | mAb1 (10 mg/kg) |
| 5 | Vγ9Vδ2T cells (3 × 106 cells) + IL-15a + mIgG1 (10 mg/kg) | No | Vγ9Vδ2 T cells (3 × 106 cells) + IL-15a + mIgG1 (10 mg/kg) | No |
| 6 | Vγ9Vδ2T cells (3 × 106 cells) + IL-15a + m20.1 (10 mg/kg) | No | Vγ9Vδ2 T cells (3 × 106 cells) + IL-15a + m20.1 (10 mg/kg) | No | a: rHu-IL-15/rHu-IL-15Rα complexes.

TABLE 17

Anti-BTN3A (mAb1) Activating mAb has Anti-leukaemic Activity In Vivo in AML Xenograft Models. Bioluminescence Data of U937 model.

|  | Mouse | Day 1 | Day 7 | Day 14 | Day 19 |
|---|---|---|---|---|---|
| Group 1 PBS | 1 | 1.10E+03 | 8.33E+04 | 1.06E+07 | Dead |
|  | 2 | 7.04E+03 | 2.50E+05 | 6.14E+07 | Dead |
|  | 3 | 7.57E+03 | 8.40E+04 | 2.41E+07 | Dead |
|  | 4 | 9.23E+03 | 2.55E+05 | 6.48E+07 | Dead |
|  | 5 | 1.37E+04 | 1.36E+05 | 3.58E+07 | Dead |
|  | Mean | 7.73E+03 | 1.62E+05 | 3.93E+07 | NA |
| Group 2 | 1 | 3.24E+03 | 1.48E+04 | 5.23E+06 | 1.82E+08 |
| LTγδ + hIgG1 | 2 | 5.61E+03 | 1.39E+05 | 3.23E+07 | Dead |
| (Day 1, 4, 7, 10) | 3 | 8.76E+03 | 3.44E+04 | 1.60E+07 | 2.23E+08 |
|  | 4 | 9.87E+03 | 2.61E+04 | 1.66E+07 | Dead |
|  | 5 | 1.03E+04 | 2.90E+05 | 3.14E+07 | 3.19E+08 |
|  | Mean | 7.56E+03 | 1.01E+05 | 2.03E+07 | NA |
| Group 3 | 1 | 3.38E+03 | 5.38E+03 | 1.89E+06 | 1.87E+08 |
| LTγδ + mAb1 | 2 | 5.22E+03 | 3.68E+04 | 3.95E+06 | 2.04E+08 |
| (Day 1, 7) | 3 | 7.49E+03 | 8.44E+04 | 1.23E+07 | 1.05E+08 |
|  | 4 | 7.73E+03 | 6.67E+04 | 4.93E+06 | 1.79E+08 |
|  | 5 | 1.29E+04 | 1.55E+04 | 5.32E+06 | 8.47E+07 |
|  | Mean | 7.34E+03 | 4.18E+04 | 5.68E+06 | 1.52E+08 |
| Group 4 | 1 | 4.08E+03 | 1.32E+03 | 2.14E+06 | 8.98E+07 |
| LTγδ + mAb1 | 2 | 5.17E+03 | 7.58E+04 | 1.55E+06 | 1.79E+08 |
| (Day 1, 4, 7, 10) | 3 | 9.21E+03 | 2.82E+04 | 6.82E+06 | 1.24E+08 |
|  | 4 | 8.97E+03 | 4.00E+04 | 6.38E+06 | 1.91E+08 |
|  | 5 | 1.00E+04 | 4.02E+04 | 3.65E+06 | 9.26E+07 |
|  | Mean | 7.49E+03 | 3.71E+04 | 4.11E+06 | 1.35E+08 |
| Group 5 | 1 | 4.15E+03 | 4.01E+04 | 2.96E+06 | 1.19E+08 |
| LTγδ + mIgG1 | 2 | 4.53E+03 | 7.96E+04 | 4.91E+06 | 2.40E+08 |
| (Day 1, 7) | 3 | 9.72E+03 | 1.66E+05 | 1.46E+07 | 2.97E+08 |
|  | 4 | 8.92E+03 | 6.36E+04 | 1.35E+07 | 1.47E+08 |
|  | 5 | 1.02E+04 | 3.97E+04 | 1.39E+07 | 1.91E+08 |
|  | Mean | 7.50E+03 | 7.78E+04 | 9.97E+06 | 1.99E+08 |
| Group 6 | 1 | 4.34E+03 | 8.51E+04 | 3.55E+06 | 1.57E+08 |
| LTγδ + m20.1 | 2 | 4.42E+03 | 3.05E+04 | 4.28E+06 | 1.87E+08 |
| (Day 1, 7) | 3 | 8.66E+03 | 6.62E+04 | 4.24E+06 | 5.55E+07 |
|  | 4 | 8.90E+03 | 3.05E+04 | 2.49E+06 | 7.32E+07 |
|  | 5 | 1.17E+04 | 1.62E+04 | 1.73E+06 | 9.61E+07 |
|  | Mean | 7.60E+03 | 4.57E+04 | 3.26E+06 | 1.14E+08 |

TABLE 18

Anti-BTN3A (mAb1) Activating mAb has Anti-leukaemic Activity In Vivo in AML Xenograft Models. Survival after U937 cell line engraftment.

|  | Mouse | Day of death |  | Mouse | Day of death |
|---|---|---|---|---|---|
| Group 1 PBS | 1 | 18 | Group 4 | 1 | 20 |
|  | 2 | 18 | LTγδ + mAb1 | 2 | 22 |
|  | 3 | 19 | (Day 1, 4, 7, 10) | 3 | 23 |
|  | 4 | 19 |  | 4 | 23 |
|  | 5 | 19 |  | 5 | 24 |
|  | Median | 19 |  | Median | 23 |
| Group 2 | 1 | 20 | Group 5 | 1 | 20 |
| LTγδ + hIgG1 | 2 | 20 | LTγδ + mIgG1 | 2 | 20 |
| (Day 1, 4, 7, 10) | 3 | 21 | (Day 1, 7) | 3 | 21 |
|  | 4 | 21 |  | 4 | 21 |
|  | 5 | 22 |  | 5 | 22 |
|  | Median | 21 |  | Median | 21 |
| Group 3 | 1 | 21 | Group 6 | 1 | 23 |
| LTγδ + mAb1 | 2 | 21 | LTγδ + m20.1 | 2 | 24 |
| (Day 1, 7) | 3 | 22 | (Day 1, 7) | 3 | 24 |
|  | 4 | 24 |  | 4 | 24 |
|  | 5 | 24 |  | 5 | 24 |
|  | Median | 22 |  | Median | 24 | b. MOLM14 Model.

The in vivo efficacy of mAb1 against MOLM14, an AraC resistant human AML derived cell line, was evaluated in a xenograft model using NSG mice transplanted with the human tumor cell line, and human Vγ9Vδ2 T cells. The goal of this study was to confirm the effect of repeated iv injections of human Vγ9Vδ2 T cells in combination with mAb1 on tumor growth and on mice survival.

Six to eight-week-old female NSG mice were injected intravenously (iv) via the tail vein at day 0 with 0.2×106 per mouse in a volume of 100111 of MOLM14 (CVCL_7916) cells expressing luciferase (luc2). Bioluminescence analysis was performed at day 0 using PhotonlMAGER (Biospace Lab) following addition of endotoxin-free luciferin (30 mg/kg) and mice were randomized in homogeneous groups of 7 mice based on the strength of the bioluminescence signal. 3x106 human in-vitro expanded Vγ9Vδ2 T cells and hIL-15/1L-15R complexes were iv injected at days 1, 8, 15, 22 and 29. mAb1 or hIgG1 were iv injected at days 1, 5, 8, 12, 15, 19, 22, 26 and 29.

The different experimental groups are summarized in Table 19.

The hIL-15/IL-15R-Fc complexes were pre-complexed at room temperature (RT) for 30 minutes before injection (0.2 ug hIL-15+1.2 ug IL-15R-Fc per mice) and mixed with Vγ9Vδ2 T cells prior injection. The final volume for each injection was 100 μl. Treatment mAbs were injected 4 hours prior to Vγ9Vδ2 T cell engraftment.

Bioluminescence signal emitted by the MOLM14 cells was measured at days 0, 7, 14, 21 and 28 after cell injection to follow tumor growth. Blood sampling was conducted at day 19 to assess the number of circulating MOLM14 cells by flow cytometry. Red cell lysis was performed before staining. mCD45+ murine cells were excluded from the analysis, MOLM14 tumor cells were detected by their GFP expression. Acquisition was performed on a LSRII SORP cytometer (Becton Dickinson) and analysis was performed using the FlowJo software. Daily monitoring of mice for symptoms of disease (significant weight loss, ruffled coat, hunched back, weakness, and reduced mobility) determined the time of killing for injected animals with signs of distress.

As shown in Table 20, Vγ9Vδ2 T cells injected with irrelevant control isotypes (hIgG1) do not significantly control tumor growth. In contrast, as shown by lower bioluminescence signals, tumor growth was strongly reduced when anti-BTN3A mAb1 was administered sequentially with human Vγ9Vδ2 T cells. Results also showed a significant decrease in the number of circulating blasts (assessed by flow cytometry in peripheral blood) at day 19 of the protocol (Table 20). Importantly, the anti-BTN3A mAb-dependent decrease in tumor growth leads a significant improvement of 45% in mice survival (as compared to the respective isotype control) (Table 22).

TABLE 19

MOLM14 mice model: group description

| Group | Number of animals | Treatment at day 7 and 14 |
|---|---|---|
| 1 | 6 | PBS |
| 2 | 7 | Vγ9Vδ2 T cells (3 × 106 cells) + IL15/IL15R-FC + hIgG1 (10 mg/kg) |
| 3 | 7 | Vγ9Vδ2 T cells (3 × 106 cells) + IL15/IL15R-Fc + mAb1 (10 mg/kg) |

TABLE 20

MOLM14 mice model: bioluminescence measurement at day 0, 7, 14, 21 and 28 after tumor cell engraftment.

| | Mouse | Day 0 | Day 7 | Day 14 | Day 21 | Day 28 |
|---|---|---|---|---|---|---|
| Group 1 | 1 | 5.1E+03 | 3.1E+04 | 1.1E+06 | 8.0E+06 | Dead |
| PBS | 2 | 1.4E+04 | 1.1E+04 | 2.5E+05 | 2.2E+06 | Dead |
| | 3 | 8.0E+03 | 3.1E+04 | 1.6E+06 | 8.8E+06 | Dead |
| | 4 | 7.2E+03 | 2.5E+04 | 7.4E+05 | 2.6E+06 | Dead |
| | 5 | 7.7E+03 | 1.6E+04 | 4.5E+05 | 1.6E+06 | Dead |
| | 6 | 4.0E+03 | 2.5E+04 | 1.6E+06 | 1.5E+07 | 2.4E+07 |
| | Mean | 7.59E+03 | 2.32E+04 | 9.57E+05 | 6.36E+06 | NA |
| Group 2 | 1 | 9.5E+03 | 2.0E+04 | 7.4E+05 | 4.0E+06 | 1.0E+07 |
| LTYγδ+ | 2 | 1.3E+04 | 5.6E+03 | 5.9E+05 | 3.1E+06 | Dead |
| hIgG1 | 3 | 7.7E+03 | 1.4E+04 | 6.0E+05 | 2.7E+06 | Dead |
| | 4 | 3.1E+03 | 4.5E+03 | 1.6E+05 | 5.6E+06 | 7.4E+06 |
| | 5 | 1.0E+04 | 1.2E+04 | 4.7E+05 | 5.5E+06 | 1.3E+07 |
| | 6 | 6.4E+03 | 3.1E+04 | 7.2E+05 | 2.8E+06 | Dead |
| | 7 | 8.8E+03 | 3.8E+03 | 2.1E+05 | 1.3E+06 | 5.4E+06 |
| | Mean | 8.45E+03 | 1.29E+04 | 4.97E+05 | 3.59E+06 | NA |
| Group 2 | 1 | 1.2E+04 | 3.0E+03 | 1.1E+04 | 8.6E+04 | 1.4E+06 |
| LTγδ+ | 2 | 3.9E+03 | 2.0E+03 | 2.0E+04 | 2.3E+04 | 2.0E+05 |
| mAb1 | 3 | 1.1E+04 | 3.4E+03 | 1.2E+05 | 2.6E+05 | 2.0E+06 |
| | 4 | 1.2E+04 | 2.6E+03 | 7.0E+03 | 1.7E+04 | 1.5E+05 |
| | 5 | 5.7E+03 | 1.9E+03 | 1.4E+04 | 1.0E+05 | 5.2E+05 |
| | 6 | 4.6E+03 | 1.3E+03 | 1.8E+04 | 2.6E+05 | 3.5E+06 |
| | 7 | 5.1E+03 | 1.3E+03 | 1.2E+04 | 1.2E+05 | 2.2E+05 |
| | Mean | 7.76E+03 | 2.19E+03 | 2.88E+04 | 1.24E+05 | 1.13E+06 |

TABLE 21

MOLM14 mice model: Number of circulating blasts at day 19 of the protocol. Data represent number of cells/ul of blood.

|  | Mouse | Day 19 |
|---|---|---|
| Group 1 PBS | 1 | 6.1 |
|  | 2 | 3 |
|  | 3 | 4.2 |
|  | 4 | 7.1 |
|  | 5 | 1.7 |
|  | 6 | 13.1 |
| Group 2 LTγδ + hIgG1 | 1 | 1.2 |
|  | 2 | 1.1 |
|  | 3 | 3.3 |
|  | 4 | 1.3 |
|  | 5 | 4 |
|  | 6 | 0.9 |
|  | 7 | 0.5 |
| Group 2 LTγδ + mAb1 | 1 | 0 |
|  | 2 | 0 |
|  | 3 | 0.02 |
|  | 4 | 0 |
|  | 5 | 0 |
|  | 6 | 0.02 |
|  | 7 | 0 |

TABLE 22

MOLM14 mice model: animal survival. Day of death for each animal is indicated together with the median survival for each group.

|  | Mouse | Day of death |
|---|---|---|
| Group 1 PBS | 1 | 23 |
|  | 2 | 26 |
|  | 3 | 27 |
|  | 4 | 27 |
|  | 5 | 28 |
|  | 6 | 31 |
|  | Median | 27 |
| Group 2 LTγδ + hIgG1 | 1 | 27 |
|  | 2 | 27 |
|  | 3 | 27 |
|  | 4 | 29 |
|  | 5 | 30 |
|  | 6 | 30 |
|  | 7 | 31 |
|  | Median | 29 |
| Group 3 LTγδ + mAb1 | 1 | 39 |
|  | 2 | 40 |
|  | 3 | 41 |
|  | 4 | 42 |
|  | 5 | 43 |
|  | 6 | 43 |
|  | 7 | 46 |
|  | Median | 42 |

9. mAb1 Improves Vγ9V152 T Cell Therapy in a Mouse Solid Tumor Model Engrafted with Human Ovarian Cancer Cell Line SKOV-3.

a. Material & Methods.

In vitro Vγ9Vδ2 T-cells expansion.

Allogeneic human Vγ9Vδ2 T lymphocytes were amplified from peripheral blood mononuclear cells (PBMC) obtained from healthy donor blood samples provide by the Etablissment Frangais du Sang (EFS, Nantes, France) and after Ficoll density centrifugation (Eurobio, Les Ulis, France). First, for specific expansions of peripheral allogeneic human Vγ9Vδ2 T lymphocytes, PBMC were incubated with 3 pM of bromohydrin pyrophosphate (BrHPP), kindly provided by Innate Pharma (Marseille, France) in RPMI medium supplemented with 10% heat-inactivated fetal calf serum, 2 mM L-glutamine, 10 mg/mL streptomycin, 100 IU/mL penicillin (all from Gibco), and 100 IU/mL recombinant human IL-2 (PROLEUKIN, Novartis, Bale, Suisse). After 4 days, cultures were supplemented with 300 IU/mL IL-2. At day 21, purity was measured by flow cytometry (purity>90%). Pure human Vγ9Vδ2 T lymphocytes were further expanded using feeder cells (mixed and 35 Gy irradiated Epstein Barr Virus transformed B lymphocytes and PBMC) and PHA-L in RPMI medium supplemented with 10% heat-inactivated fetal calf serum, 2 mM L-glutamine, 10 mg/mL streptomycin, 100 IU/mL penicillin (all from Gibco), and 300 IU/mL recombinant human IL-2 (Novartis). After three weeks, resting ex vivo expanded-Vγ9Vδ2 T lymphocytes were used for in vivo experiments.

Mouse Model

At day 0, 6-8 weeks of age NSG mice were injected intraperitoneally (ip) with 1x106 SKOV-3 cells (Ovarian cancer cell line, SKOV-3-luc-D3, Perkin Elmer, Waltham, MA) expressing luciferase per mouse in a volume of 100 μL of sterile PBS. After 7 days, mice were randomized in homogeneous groups of 5 to 6 mice. At days 7 and 14, mAbs treatments, 200 μg per mouse of mAb1 or relevant isotype control (hIgG1), were injected ip in 100 μL of sterile PBS. 4 hours later, 5x106 of human in-vitro expanded Vγ9Vδ2 T cells were also injected ip in 100 μL of sterile PBS per mouse.

Bioluminescence signal emitted by the SKOV-3 cells was measured at days 16, 23 and 30 after tumor cell implantation to follow tumor growth. Bioluminescent imaging was realized 8 minutes after ip injection of 1.5 mg of D-luciferin (Interchim, San Diego, CA), on mice anesthetized with isoflurane 2%, with Biospace Imager (Biospace Lab, Nesles-la-Vallee, France). Experimental endpoint was reached when mice lost 10% of their initial weight.

b. Results The in vivo efficacy of mAb1 against ovarian cancer was evaluated in a xenograft model using NSG mice transplanted with the human ovarian cancer cell line SKOV-3, and human Vγ9Vδ2 T cells. The goal of this study was to assess the effect of two ip injections of human Vγ9Vδ2 T cells in combination with mAb1 on tumor growth and on mice survival.

NSG mice were injected intraperitoneally (ip) at day 0 with SKOV3. After 7 days, mice were randomized in homogeneous groups according to treatments. Groups are described in Table 23:

TABLE 23

Ovarian cancer mice model: group description

| Group | Number of animals | Treatment at day 7 and 14 |
|---|---|---|
| 1 | 5 | PBS |
| 2 | 6 | Vγ9Vδ2 T cells (5 × 106 cells) + hIgG1 (10 mg/kg) |
| 3 | 6 | Vγ9Vδ2 T cells (5 × 106 cells) + mAb1 (10 mg/kg) |

Result showed that human Vγ9Vδ2 T cells transferred together with mAb1 significantly delayed tumor growth (Table 24) leading to a significant improvement of animal survival (Table 25). Of note, this effect was observed in the absence of pro-Vγ9Vδ2 T survival cytokines such as IL-2 or IL-15.

TABLE 24

Ovarian cancer mice model: bioluminescence measurement 16, 23 and 30 days after tumor cell engraftment.

|  | Mouse | Day 16 | Day 23 | Day 30 |
|---|---|---|---|---|
| Group 1 PBS | 1 | 87220 | Dead | Dead |
|  | 2 | 48486 | 92643 | Dead |
|  | 3 | 89032 | 89930 | Dead |
|  | 4 | 74242 | 121010 | Dead |
|  | 5 | 82132 | 128390 | Dead |
|  | Mean | 7.62E+04 | 1.08E+05 | NA |
| Group 2 LTγδ + hIgG1 | 1 | 32060 | 70953 | Dead |
|  | 2 | 82703 | 166009 | Dead |
|  | 3 | 23049 | 51909 | 150537 |
|  | 4 | 85130 | 147390 | Dead |
|  | 5 | 18053 | 45097 | Dead |
|  | 6 | 41732 | 76461 | Dead |
|  | Mean | 4.71E+04 | 9.30E+04 | NA |
| Group 2 LTγδ + mAb1 | 1 | 43000 | 42420 | 80574 |
|  | 2 | 20706 | 43670 | 63418 |
|  | 3 | 6891 | 47150 | 70070 |
|  | 4 | 11845 | 48139 | 36820 |
|  | 5 | 22958 | 29131 | 74111 |
|  | 6 | 12725 | 19767 | Dead |
|  | Mean | 1.97E+04 | 3.84E+04 | 6.50E+04 |

TABLE 25

Ovarian cancer mice model: animal survival. Day of death for each animal is indicated together with the median survival for each group.

|  | Mouse | Day of death |
|---|---|---|
| Group 1 PBS | 1 | 20 |
|  | 2 | 23 |
|  | 3 | 23 |
|  | 4 | 23 |
|  | 5 | 28 |
|  | Median | 23 |
| Group 2 LTγδ + hIgG1 | 1 | 23 |
|  | 2 | 23 |
|  | 3 | 28 |
|  | 4 | 28 |
|  | 5 | 28 |
|  | 6 | 35 |
|  | Median | 28 |
| Group 3 LTγδ + mAb1 | 1 | 28 |
|  | 2 | 35 |
|  | 3 | 35 |
|  | 4 | 35 |
|  | 5 | 35 |
|  | 6 | 39 |
|  | Median | 35 |

10. In-Vivo Effect on Cynomolgus Monkey Vγ9Vδ2 T-Cells

Because of the absence of BTN3A and the Vγ9Vδ2 T subset in rodents, and based on previous data documenting in vitro and in vivo PAg-mediated Vγ9Vδ2 T cell activation in cynomolgus macaques, the cynomolgus monkey (*Macaca fascicularis*) was selected as the only relevant species for nonclinical safety evaluation of mAb1.

a. Material & Methods

Biacore mAb1 has been assessed for binding to recombinant human or cynomolgus BTN3A1, BTN3A2 and BTN3A3 proteins (SEQ ID NO 21, 22 and 23 respectively) via Biacore multi-cycle kinetics analysis using a Biacore T200 (Ser. No. 1909913) instrument. mAb1 was diluted to a concentration of 2 pg/ml in 2% BSA/PBS. At the start of each cycle, antibody was captured on the Protein A surface at a density (RL) of ~150 RU (the theoretical value to obtain an RMax of ~50 RU). Following capture, the surface was allowed to stabilize before injection of the BTN3A antigen. BTN3A was titrated in 0.1% BSA/HBS-P+(running buffer) in a two-fold dilution range from 25 to 0.78 nM. The association phase was monitored for 420 seconds and the dissociation phase for 2000 seconds. Kinetic data was obtained using a flow rate of 50 μl/min to minimize any potential mass transfer effects. Obtained data was fitted using a 1:1 binding model.

ELISA

The apparent affinity of mAb1 for Human and cynomolgus BTN3A1 was tested by ELISA. Briefly, the binding of mAb1 on the target was evaluated using recombinant BTN3A1 immobilized on a plate at 1 pg/ml in Phosphate buffer (1x PBS), followed by a saturation step with block buffer (2% milk/PBS)). mAb1 was titrated in block buffer in a four-fold dilution range from 0.00122 to 20 pg/ml. A secondary antibody (Goat Anti-Human Iv chain, HRP conjugated antibody, Millipore AP502P, diluted 1:4000 in block buffer) and TMB solution were used for detection. The apparent affinity was expressed as the $EC_{50}$% (the antibody concentration required to obtain 50% of the signal plateau).

Binding Avidity of mAb1 to Human and Cynomolgus CD3+ Cells.

After red blood cells lysis, human or cynomolgus PBL were incubated with increasing concentration of mAb1 or isotype control for 30 min at 4° C., washed two times and stained with a goat anti-human-IgG-PE conjugated secondary antibody (eBioscience™ #12-4998-82). After 2 washes, cells were stained with an anti-CD3-PC3 mAb (BD Bioscience #557749) and live/Dead reagent (Life Technology #L10119). After washes, cells were resuspended in 200 μL Flow buffer. Cells were then analysed on a Cytoflex cytometer (Beckman Coulter). Data were analysed using FlowJo software (Version 10, FlowJo, LLC, Ashland, USA) gating on the live CD3+ population. The MFI values from PE channel were then calculated and plotted against concentration. Curves fitting was obtained using sigmoidal 4PL equation from Graph Pad Prism software.

BTN3A Surface Expression on Human and Cynomolgus Circulating Cells.

For BTN3A surface expression on leukocytes, 100 ul of Cynomolgus and human whole blood were plated in 96 well plates with a cocktail of specific antibodies (Aqua live Dead reagent, CD20-V450, CD8-BVδ05, CD4-BVδ50, Vg9 TCR-FITC, anti-BTN3A-PE (clone 20.1) (or mIgG1-PE for isotype control), CD3-PeCy7, CD45-AF700 and CD14-APC-H7) and incubated 15 minutes at RT protected from light. Then, red blood cells were lysed with 900 μl of lysing reagent (BD Bioscience #349202) according to manufacturer instructions. Cells were washed and analysed using multiparametric Flow cytometry. For BTN3A surface expression on Red blood cells and platelets, 100 μl of cynomolgus or human whole blood were diluted with 100 μl of PBS and incubated with a specific cocktail of antibodies (Aqua live dead, CD41-APC, CD45-AF700 and anti-BTN3A (clone 20.1) (or mIgG1-PE for isotype control)) for 15 minutes at RT protected from light. After washes, cells were analysed using multiparametric Flow cytometry. In order to obtain a relative quantification of BTN3A surface expression, calibrating beads (CellQuant Calibrator Biocytex #7208) and goat anti-mouse IgG (H+L)-PE were used in parallel according to manufacturer instruction. For every cell subset, MFI of the PE channel was reported for anti-BTN3A and isotype control. Analysis was performed by subtracting the MFI of the isotype control from the MFI of the anti-BTN3A staining and relative surface expression was calculated based on the standard curve obtained with calibration beads.

Cynomolgus Vγ9Vδ2 T cell in-vitro expansion and activation.

Cynomolgus whole blood from 3 animals was treated with red blood lysis buffer. After extensive washes, leukocytes were plated at 1.5M/ml of RPMI 10% SVF in 6 well plates in presence of rHuIL-2 (200 IU/ml) and mAb1 (10 ug/ml). rHuIL-2 was added at day 6 and 8 to mimic the usual cell expansion protocol used with human PBMC, and improve Vγ9Vδ2 T cell long term in vitro survival in order to obtain sufficient number of cells to perform functional assays. The percentage of Vγ9+ T cells was assessed at day 0, 6, 8 and 10 using a cocktail of specific antibodies and flow cytometry analysis (CD3-PC7 BD Bioscience #557749, Vg9 TCR-FITC clone 7A5 lnvitrogen #TCR2720, Live Dead Near IR Thermo Fisher #L10119).

At day 10, expanded Vγ9Vδ2 T cells were counted and co-culture at E:T ratio of 1:1 with human tumoral cell lines. 100 000 target tumoral cell lines (Raji, DAUDI and K562) were mixed with 100 000 cynomolgus Vγ9Vδ2 T cells in presence of mAb1 or hIgG1 isotype control (10 ug/ml) or PMA (20 ng/ml)/ionomycin (1 ug/ml) used as positive control in 96 well plates. Vγ9Vδ2 T-cell degranulation was monitored after 4 hrs using CD107a/b (BD bioscience #555800) staining and flow cytometry analysis.

Cynomolgus Monkey In-Vivo Study

In Life Study

Four- to 6-year-old, 3- to 5-kg, cynomolgus monkeys (*Macaca fascicularis*) of Vietnamese origin were used in this study. All animals were maintained and used in accordance with guidelines of the institutional animal care and use committee in a GLP animal facility. As a breeder health procedure, all animals were tested for tuberculosis, and prophylactic treatments were documented in the breeder's records. After arrival, animals were acclimated to study procedures for a period of at least 2 weeks. A clinical inspection for ill-health and testing for were performed. An animal health assessment was performed by a Veterinarian before the start of the predose phase to confirm the suitability of every animal for the study.

mAb1 was administered intravenously (chair restrained, infusion over 15 minutes) after disinfecting the skin of non-fasted animals. Animals of Groups 1, 4, and 5 were dosed on Days 1, 8, 15, and 22. Animals of Groups 2 and 3 were dosed once on Day 1.

Pharmacokinetics

A qualified pharmacokinetic assay was developed for the quantification of mAb1 in cynomolgus monkey serum. Briefly, mAb1 is quantified using ELISA by spectrophotometry. A Streptavidin precoated plate is used to capture the human IgG-Fc PK Biotin Conjugate. mAb1 is then captured on the surface of the plate and the bound analyte is detected using the Goat anti-human IgG-HRP (Fc specific) antibody, a peroxidase-labelled anti-species antibody. The target range of quantification is from 90 ng/mL to 10000 ng/mL in neat serum.

Immunophenotyping

Blood samples (1.0 mL) were withdrawn from all animals from the vena cephalica antebrachii or vena saphena into Li-Heparin tubes. Immunophenotyping was done with cocktails of specific monoclonal antibodies. Analyses of relative cell numbers (percentage of lymphocytes/leucocytes) were performed. Total granulocyte/lymphocyte/leucocyte counts were determined on the same day by hemoanalyser and used for calculation of absolute numbers. Absolute numbers of the lymphocyte subpopulations were computed from relative numbers.

Receptor occupancy

Blood samples (400 NL) were withdrawn from all animals from the vena cephalica antebrachii or vena saphena into Li-Heparin tubes. A labeled antibody binding non-competitively to BTN3A (clone 103.2) on cells, which was pre-incubated with a surplus of ICT01 was used to determine the total surface BTN3A expression on CD3+ T-cells and CD19+ B cells. For detection of free BTN3A binding sites, the competitive binding of unlabelled mAb1 to BTN3A which inhibits the binding of fluorescence dye labeled anti-BTN3A antibody (mAb1) on CD3+ T-cells and CD19+B cells was used. Depending on the amount of BTN3A that was blocked by mAb1, the mean fluorescence intensity (MFI) of conjugated-mAb1 was measured as geometric mean was reduced. Consequently, a staining intensity of Ab7.2 close to that of the isotype antibody was indicative of a complete saturation.

b. Results mAb1 binds to cynomolgus BTN3A.

As differential identification of the 3 BTN3A isoform genes was not possible from public databases, ImCheck performed targeted PCR on cDNA isolated from cynomolgus PBMC, using a highly conserved cDNA sequence close to the transmembrane domain to design a relevant primer. Sequencing of PCR products allowed identification of ectodomain sequences for cynomolgus BTN3A1, BTN3A2, and BTN3A3. Recombinant ectodomains of cynomolgus BTN3A1, BTN3A2 and BTN3A3 isoforms fused to a 6xHis tag were produced in CHO cells based on these sequences (SEQ ID NO 21, 22 and 23 respectively).

Recombinant proteins were tested for mAb1 binding by BIAcore and ELISA (Table 26). BIAcore results showed mAb1 advantageously binds to the 3 cynomolgus recombinant BTN3A1, BTN3A2 and BTN3A3, although with a lower affinity for the BTN3A1 isoform. ELISAs were performed on BTN3A1 isoforms. Interestingly, Table 26 shows comparable $EC_{50}$ for mAb1 binding on recombinant human or cynomolgus BTN3A1.

TABLE 26 mAb1 Binding to Human and Cynomolgus BTN3A Recombinant Proteins

| Protein | Tag | $K_D$ (M) - BIAcore (MCK) | $EC_{50}$ (M) - ELISA |
|---|---|---|---|
| Human BTN3A1 (Sino biological # 15973-H08H) | C-ter His | 0.408E−9 | 0.93E−9 |
| CynoBTN3A1 | C-ter-His | 83.8E−09 | 1.33E−9 |
| CynoBTN3A2 | C-ter His | 5.97E−09 | nd |
| CynoBTN3A3 | C-ter His | 2.67E−09 | nd | nd: not determined

In parallel, mAb1 binding on cynomolgus PBMCs was evaluated by flow cytometry. The mean $EC_{50}$ of mAb1 binding to cynomolgus CD3+ T cells was comparable to that of human CD3+ T cells (Table 27). Target expression on different immune cell sub-populations from cynomolgus versus human healthy donor whole blood was addressed by multiparameter flow cytometry, using PE-conjugated anti-BTN3A mAb (clone 20.1) together with a panel of phenotyping antibodies with known cross-reactivities for human and cynomolgus macaque cell surface markers (Data not shown). These results show that BTN3A is expressed in a broad panel of peripheral blood cell populations in both species, although an apparent, generally lower expression was observed in cynomolgus macaques.

TABLE 27 mAb1 Binding on Human and Cynomolgus CD3+ T Cells

Figure 4:
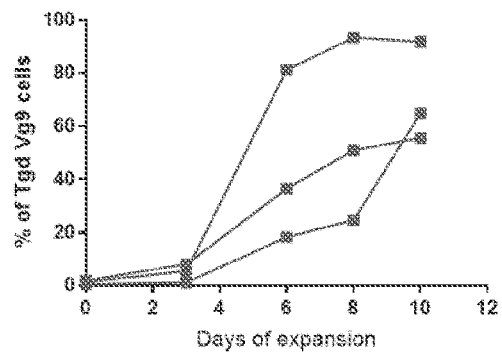
FIG. 4: mAb1 Promotes Expansion and Activation of Cynomolgus Monkey Vγ9V.52 T Cells
A. Cynomolgus whole blood from 3 animals was treated with red blood cells lysis buffer. After extensive washes, cells were plated at 1.5 M/mL in medium containing 200 IU/mL rHuIL-2 and mAb1 (10 μg/mL). Percentage of Vγ9+ T cells was assessed by flow cytometry at day 0, 3, 6, 8 and 10 using a specific antibody. Graph shows the kinetic of Vγ9+ T cell percentage among live cells. Each curve represents an individual animal.
B. After 10 days expansion, cells from each animal were cocultured for 4 hrs with Daudi, K562 or Raji used as target cells (ratio E:T 1:1) in presence of culture medium, mAb1 or isotype control (10 μg/mL) and analysed for degranulation (CD107a/b) by flow cytometry.
Figure 4:
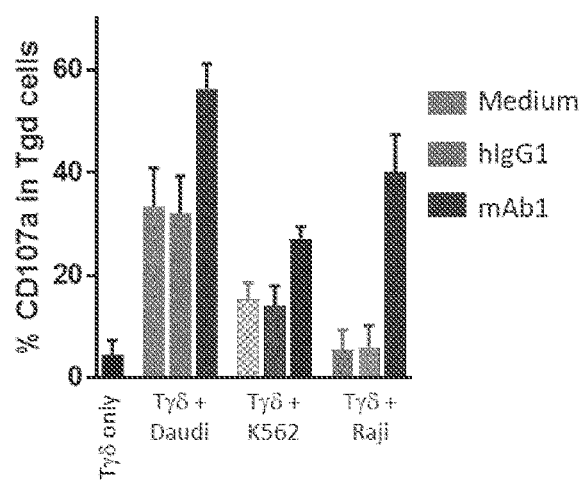

| Cells | Origin | Description | Gating | EC$_{50}$ (μg/mL) (+/−sem) | EC$_{50}$ (×10$^9$ M) (+/−sem) |
|---|---|---|---|---|---|
| Human HV PBMCs | EFS Marseille | Primary (n = 6) | CD3+ | 5.25 (+/−0.57) | 34.9 (+/−3.8) |
| Cynomolgus PBMCs | Covance Munster | Primary (n = 6) | CD3+ | 7.02 (+/−0.89) | 46.79 (+/−5.94) | mAb 1 promote cynomolgus Vγ9Vδ2 T-cell expansion and activation in-vitro. Next, the functional activity of mAb1 was assessed on cynomolgus Vγ9Vδ2 T cell in vitro. First, we evaluated whether mAb1 promotes cynomolgus Vγ9Vδ2 T cell expansion when incubated for 10 days with cynomolgus PBMCs. As shown in FIG. 4A, mAb1 promoted Vγ9Vδ2 T cells expansion in all 3 animal tested; this population reaching 60% after 10 days, a level comparable to that observed for human cells. After 10 days expansion, cells were cocultured for 4 hrs with Daudi, K562 or Raji cell lines used as target cells in the presence of mAb1, and analysed for CD107a/b expression by flow cytometry. This experiment showed that mAb1 induces a significant Vγ9Vδ2 T cell activation when co-cultured with all 3 tumour cell lines (FIG. 4B).

In conclusion, the results show that (i) mAb1 binds to cynomolgus cells with a similar avidity to human cells, (ii) BTN3A is expressed on the same blood cells in humans and cynomolgus monkeys, although a lower expression level was observed in the latter species, and (iii) mAb1 promotes Vγ9Vδ2 T cell subset expansion in cynomolgus PBMC, and expanded cells are reactive against mAb1-pulsed tumour target cells.

mAb1 Affects Cynomolgus Vg9Vd2 T-Cell Compartment In-Vivo.

An in-vivo study was conducted in 4 to 6 years old healthy female cynomolgus monkey which received single or repeated intravenous infusions of mAb1 (Table 28).

The intravenous route of administration was chosen because it is the intended human therapeutic route. Animals were treated with mAb1 according to a staggered escalating dose design.

TABLE 28 mAb1 PK/PD/Tolerability Study Design

| Group | Test item | Dose (mg/kg) | Number of weekly injections | Number and gender of animals |
|---|---|---|---|---|
| 1 | mAb1 | 0.1-1-10-100 | 4 (ascending doses) | 1F (sentinel animal) |
| 2 | | 1 | 1 | 3F |
| 3 | | 10 | 1 | 2F |
| 4 | | 10 | 4 | 2F |
| 5 | | 100 | 4 | 2F |

The following endpoints were evaluated: clinical signs, bodyweights, clinical pathology (haematology, clinical chemistry and coagulation), immunophenotyping for peripheral blood leukocyte populations, activation/proliferation/differentiation markers, pharmacokinetics and pharmacodynamics (BTN3A receptor occupancy on circulating T and B cells).

All animals survived up to the scheduled necropsy on Day 29 of the study, after receiving single or 4 repeated 15-minute infusions of the mAb1. No test article-related effects were found on body weights or food-consumption. Clinical signs were consistent with observations seen in cynomolgus monkeys in laboratory housing settings and thus, not attributable to a test article.

Pharmacokinetics mAb1 showed approximately dose-proportional pharmacokinetic behaviour following intravenous (IV) dosing over the dose range of 0.1 to 100 mg/kg (Data not shown), and a long elimination half-life typical of IgG mAbs in the absence of target-mediated clearance. Following repeated doses of 10 or 100 mg/kg/week for 4 doses (Data not shown), exposure was maintained in all animals over the treatment period, with only minimal accumulation over the 4-week treatment period. The pharmacokinetic profiles for the sentinel animal following the doses of 1 and 10 mg/kg IV in an escalating weekly dosing regimen showed some evidence for increased clearance towards the end of the weekly dosing interval which may be a result of formation of ADAs to mAb1; there was no evidence for increased clearance after the last IV dose of 100 mg/kg.

Receptor Occupancy (RO)

According to the BTN3A expression profile and cell population representation in blood, mAb1 RO was measured on CD3+ T cells and CD20+B cells.

The results show that BTN3A is rapidly occupied after mAb1 injection on both CD3+ T cells and CD20+B cells (Data not shown). Repeated dosing at 100 mg/kg mAb1 appeared to be required for a full receptor occupancy throughout the weekly dosing interval.

Immunophenotyping

At selected time-points after each dose, blood of animals receiving mAb1 has been stained with a cocktail of specific mAbs to quantify T cells subsets (CD4, CD8, Vγ9 T cells, regulatory T cells), B cells, monocytes, NK cells, mDCs, pDCs and granulocytes and associated activation markers (CD69, CD86, CD95, Granzyme B, Ki67) and analysed by flow cytometry. Analysis included relative cell numbers (percentage of lymphocytes/leucocytes) for each population together with absolute cell numbers extrapolated from total lymphocyte/leucocyte counts determined from blood samples harvested at same time and analysed using an haematological cell counter.

Figure 5:
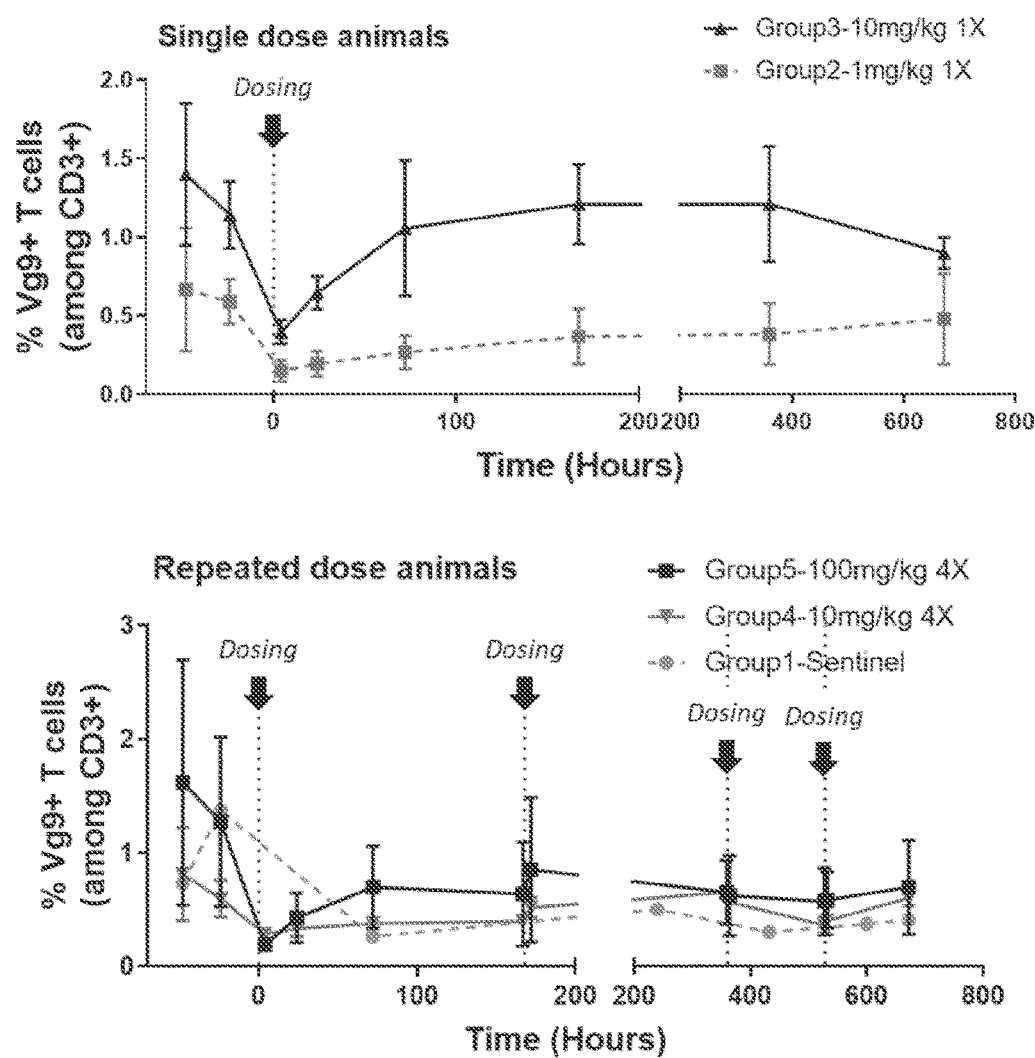
FIG. 5: Cynomolgus blood samples collected at indicated times after ICT01 dosing were stained with specific cocktail of antibodies to quantify T cells subsets (CD4, CD8, Vγ9 T cells, regulatory T cells), B cells, monocytes, NK cells, mDCs, pDCs and granulocytes and analyzed by flow cytometry. The upper panel showed the % of Vγ9δ2 T cells among CD3+ T cells for single dose animals. The lower panel showed the % of Vγ9δ2 T cells among CD3+ T cells for repeated dose animals. Data are presented as mean values ±SD for each sampling occasion and group. Vertical dotted lines indicated time of ICT01 dosing.

The main observations from this broad analysis are:
Vδ9+ T cells (% among CD3+) significantly drop after dosing in all animals receiving mAb1 and come back up progressively on single dose animals. This effect appears to be specific, as it is not observed in CD4 and CD8 αβ T cells, and is suggestive of γδ T cell activation and margination on tissues, as observed for CD3 engager bi-specifics antibodies in monkeys and humans (Smith et al., 2015 Sci Rep. 2015 Dec. 11; 5:17943. doi: 10.1038/srep17943.). The results are shown in FIG. 5.

This study shows that mAb1, when administered by the IV route, appears to be well tolerated at doses up to 100 mg/kg/week. Moreover, among T cell subsets, Vγ9Vδ2 T cells are specifically and significantly affected by mAb1.

BIBLIOGRAPHY

Alegre, M.-L., Frauwirth, K. A., and Thompson, C. B. (2001). T-cell regulation by CD28 and CTLA-4. Nat. Rev. Immunol. 1, 220-228.

Ausubel, F. M., Brent, R., Kingston, R. E., Moore, D. D., Seidman, J. G., and Struhl, K. (1988). Current Protocols in Molecular Biology (John Wiley & Sons).

Baudino, L., Shinohara, Y., Nimmerjahn, F., Furukawa, J.-I., Nakata, M., Martinez-Soria, E., Petry, F., Ravetch, J. V., Nishimura, S.-I., and Izui, S. (2008). Crucial Role of Aspartic Acid at Position 265 in the CH2 Domain for Murine IgG2a and IgG2b Fc-Associated Effector Functions. J. Immunol. 181, 6664-6669.

Bensussan, A., and Olive, D. (2005). T-cell: Section report. Cell. Immunol. 236, 3-5.

Bird, R. E., Hardman, K. D., Jacobson, J. W., Johnson, S., Kaufman, B. M., Lee, S. M., Lee, T., Pope, S. H., Riordan, G. S., and Whitlow, M. (1988). Single-chain antigen-binding proteins. Science 242, 423-426.

Brennan, M., Davison, P. F., and Paulus, H. (1985). Preparation of bispecific antibodies by chemical recombination of monoclonal immunoglobulin G1 fragments. Science 229, 81-83.

Bryson, C. J., Jones, T. D., and Baker, M. P. (2010). Prediction of Immunogenicity of Therapeutic Proteins. BioDrugs 24, 1-8.

Chapoval, A. I., Ni, J., Lau, J. S., Wilcox, R. A., Flies, D. B., Liu, D., Dong, H., Sica, G. L., Zhu, G., Tamada, K., et al. (2001). B7-H3: A costimulatory molecule for T cell activation and IFN-γ production. Nat. Immunol. 2, 269-274.

Collins, M., Ling, V., and Carreno, B. M. (2005). The B7 family of immune-regulatory ligands. Genome Biol. 6,223.

Coyle, A. J., and Gutierrez-Ramos, J. C. (2001). The expanding B7 superfamily: increasing complexity in costimulatory signals regulating T cell function. Nat. Immunol. 2, 203-209.

Dong, H., Zhu, G., Tamada, K., and Chen, L. (1999). B7-H1, a third member of the B7 family, co-stimulates T-cell proliferation and interleukin-10 secretion. Nat. Med. 5, 1365-1369.

Freeman, G. J., Long, A. J., Iwai, Y., Bourque, K., Chernova, T., Nishimura, H., Fitz, L. J., Malenkovich, N., Okazaki, T., Byrne, M. C., et al. (2000). Engagement of the Pd-1 Immunoinhibitory Receptor by a Novel B7 Family Member Leads to Negative Regulation of Lymphocyte Activation. J. Exp. Med. 192, 1027-1034.

Glennie, M. J., McBride, H. M., Worth, A. T., and Stevenson, G. T. (1987). Preparation and performance of bispecific F(ab' gamma)2 antibody containing thioether-linked Fab' gamma fragments. J. Immunol. 139, 2367-2375.

Goeddel, D. V. (1990). [1] Systems for heterologous gene expression. In Methods in Enzymology, (Academic Press), pp. 3-7.

Gu, S., Nawrocka, W., and Adams, E. J. (2015). Sensing of Pyrophosphate Metabolites by Vγ9Vδ2 T Cells. Front. Immunol. 5.

Harly, C., Guillaume, Y., Nedellec, S., Feign& C.-M., Monkkonen, H., Monkkonen, J., Li, J., Kuball, J., Adams, E. J., Netzer, S., et al. (2012). Key implication of CD277/butyrophilin-3 (BTN3A) in cellular stress sensing by a major human yo T-cell subset. Blood 120, 2269-2279.

Huston, J. S., Levinson, D., Mudgett-Hunter, M., Tai, M. S., Novotny, J., Margolies, M. N., Ridge, R. J., Bruccoleri, R. E., Haber, E., and Crea, R. (1988). Protein engineering of antibody binding sites: recovery of specific activity in an anti-digoxin single-chain Fv analogue produced in *Escherichia coli*. Proc. Natl. Acad. Sci. 85, 5879-5883.

Kabat, E. A., Wu, T. T., Foeller, C., Perry, H. M., and Gottesman, K. S. (1992). Sequences of Proteins of Immunological Interest (DIANE Publishing).

Karpovsky, B., Titus, J. A., Stephany, D. A., and Segal, D. M. (1984). Production of target-specific effector cells using hetero-cross-linked aggregates containing anti-target cell and anti-Fc gamma receptor antibodies. J. Exp. Med. 160, 1686-1701.

Kaufman, R. J., and Sharp, P. A. (1982). Construction of a modular dihydrofolate reductase cDNA gene: analysis of signals utilized for efficient expression. Mol. Cell. Biol. 2, 1304-1319.

Khattri, R., Auger, J. A., Griffin, M. D., Sharpe, A. H., and Bluestone, J. A. (1999). Lymphoproliferative Disorder in CTLA-4 Knockout Mice Is Characterized by CD28-Regulated Activation of Th2 Responses. J. Immunol. 162, 5784-5791.

Klocke, K., Sakaguchi, S., Holmdahl, R., and Wing, K. (2016). Induction of autoimmune disease by deletion of CTLA-4 in mice in adulthood. Proc. Natl. Acad. Sci. 113, E2383— E2392.

Latchman, Y., Wood, C. R., Chernova, T., Chaudhary, D., Borde, M., Chernova, I., Iwai, Y., Long, A. J., Brown, J. A., Nunes, R., et al. (2001). PD-L2 is a second ligand for PD-1 and inhibits T cell activation. Nat. Immunol. 2, 261-268.

Linsley, P. S., Greene, J. L., Tan, P., Bradshaw, J., Ledbetter, J. A., Anasetti, C., and Damle, N. K. (1992). Coexpression and functional cooperation of CTLA-4 and CD28 on activated T lymphocytes. J. Exp. Med. 176, 1595-1604.

Liu, M. A., Kranz, D. M., Kurnick, J. T., Boyle, L. A., Levy, R., and Eisen, H. N. (1985). Heteroantibody duplexes target cells for lysis by cytotoxic T lymphocytes. Proc. Natl. Acad. Sci. 82, 8648-8652.

McCafferty, J., Griffiths, A. D., Winter, G., and Chiswell, D. J. (1990). Phage antibodies: filamentous phage displaying antibody variable domains. Nature 348, 552-554.

Morrison, S. L. (1985). Transfectomas provide novel chimeric antibodies. Science 229, 1202-1207.

Ni, L., and Dong, C. (2017). New B7 Family Checkpoints in Human Cancers. Mol. Cancer Ther. 16, 1203-1211.

Oganesyan, V., Gao, C., Shirinian, L., Wu, H., and Dall'Acqua, W. F. (2008). Structural characterization of a human Fc fragment engineered for lack of effector functions. Acta Crystallogr. D Biol. Crystallogr. 64, 700-704.

Panowski, S., Bhakta, S., Raab, H., Polakis, P., and Junutula, J. R. (2013). Site-specific antibody drug conjugates for cancer therapy. MAbs 6, 34-45.

Paulus, H. (1985). Preparation and biomedical applications of bispecific antibodies. Behring Inst. Mitt. 118-132.

Perry, L. C. A., Jones, T. D., and Baker, M. P. (2008). New approaches to prediction of immune responses to therapeutic proteins during preclinical development. Drugs RD 9, 385-396.

Reddy, M. P., Kinney, C.A.S., Chaikin, M. A., Payne, A., Fishman-Lobell, J., Tsui, P., Monte, P. R. D., Doyle, M. L., Brigham-Burke, M. R., Anderson, D., et al. (2000). Elimination of Fc Receptor-Dependent Effector Functions of a Modified IgG4 Monoclonal Antibody to Human CD4. J. Immunol. 164, 1925-1933.

Remington, J. P., and Gennaro, A. R. (1995). Remington: the science and practice of pharmacy (Easton, PA: Mack Publishing).

Rhodes, D. A., Stammers, M., Malcherek, G., Beck, S., and Trowsdale, J. (2001). The Cluster of BTN Genes in the Extended Major Histocompatibility Complex. Genomics 71, 351-362.

Ruddy, D. A., Kronmal, G. S., Lee, V. K., Mintier, G. A., Quintana, L., Domingo, R., Meyer, N.C., Irrinki, A., McClelland, E. E., Fullan, A., et al. (1997). A 1.1-Mb Transcript Map of the Hereditary Hemochromatosis Locus. Genome Res. 7, 441-456.

Saverino, D., Tenca, C., Zarcone, D., Merlo, A., Megiovanni, A. M., Valle, M. T., Manca, F., Grossi, C. E., and Ciccone, E. (1999). CTLA-4 (CD152) Inhibits the Specific Lysis Mediated by Human Cytolytic T Lymphocytes in a Clonally Distributed Fashion. J. Immunol. 162, 651-658.

Sharpe, A. H., and Freeman, G. J. (2002). The B7—CD28 superfamily. Nat. Rev. Immunol. 2, 116-126.

Sharpe, A. H., and Pauken, K. E. (2018). The diverse functions of the PD1 inhibitory pathway. Nat. Rev. Immunol. 18, 153-167.

Shukla, A. A., Hubbard, B., Tressel, T., Guhan, S., and Low, D. (2007). Downstream processing of monoclonal antibodies—Application of platform approaches. J. Chromatogr. B 848, 28-39.

Stech, M., Nikolaeva, 0., Thoring, L., Stocklein, W. F. M., Wustenhagen, D. A., Hust, M., Dubel, S., and Kubick, S. (2017). Cell-free synthesis of functional antibodies using a coupled in vitro transcription-translation system based on CHO cell lysates. Sci. Rep. 7, 12030.

Strohl, W. R. (2009). Optimization of Fc-mediated effector functions of monoclonal antibodies. Curr. Opin. Biotechnol. 20, 685-691.

Takebe, Y., Seiki, M., Fujisawa, J., Hoy, P., Yokota, K., Arai, K., Yoshida, M., and Arai, N. (1988). SR alpha promoter: an efficient and versatile mammalian cDNA expression system composed of the simian virus 40 early promoter and the R-U5 segment of human T-cell leukemia virus type 1 long terminal repeat. Mol. Cell. Biol. 8, 466-472.

Tseng, S.-Y., Otsuji, M., Gorski, K., Huang, X., Slansky, J. E., Pai, S. I., Shalabi, A., Shin, T., Pardoll, D. M., and Tsuchiya, H. (2001). B7-Dc, a New Dendritic Cell Molecule with Potent Costimulatory Properties for T Cells. J. Exp. Med. 193, 839-846.

Urlaub, G., and Chasin, L. A. (1980). Isolation of Chinese hamster cell mutants deficient in dihydrofolate reductase activity. Proc. Natl. Acad. Sci. U.S.A 77, 4216-4220.

Williams, A. F., and Barclay, A. N. (1988). The immunoglobulin superfamily--domains for cell surface recognition. Annu. Rev. Immunol. 6, 381-405.

---

SEQUENCE LISTING

```
Sequence total quantity: 23
SEQ ID NO: 1             moltype = AA  length = 122
FEATURE                  Location/Qualifiers
source                   1..122
                         mol_type = protein
                         organism = Homo sapiens
SEQUENCE: 1
QVQLVQSGAE VKKPGASVKL SCKASGYIFT RYYMYWVKQR PGQGLEWIGE INPNNGGTKF   60
NEKFKNRATL TVDKSISTAY MELSRLRSDD TAVYYCSRED DYDGTPFAMD YWGQGTLVTV  120
SS                                                                122

SEQ ID NO: 2             moltype = AA  length = 107
FEATURE                  Location/Qualifiers
source                   1..107
                         mol_type = protein
                         organism = Homo sapiens
SEQUENCE: 2
DIQMTQSPSS LSASVGDRVT ITCHASQNIN VWLSWYQQKP GKAPKLLIYK ASNLHTGVPS   60
RFTGSGSGTD FTFTISSLQP EDIATYYCQQ GQTYPYTFGQ GTKLEIK                107

SEQ ID NO: 3             moltype = AA  length = 107
FEATURE                  Location/Qualifiers
source                   1..107
                         mol_type = protein
                         organism = Homo sapiens
SEQUENCE: 3
DIQMTQSPSS LSASVGDRVT ITCHASQNIN VWLSWYQQKP GKAPKLLIYK ASNLHTGVPS   60
RFSGSGSGTD FTFTISSLQP EDIATYYCQQ GQTYPYTFGQ GTKLEIK                107

SEQ ID NO: 4             moltype = AA  length = 451
FEATURE                  Location/Qualifiers
source                   1..451
                         mol_type = protein
                         organism = Homo sapiens
SEQUENCE: 4
QVQLVQSGAE VKKPGASVKL SCKASGYIFT RYYMYWVKQR PGQGLEWIGE INPNNGGTKF   60
NEKFKNRATL TVDKSISTAY MELSRLRSDD TAVYYCSRED DYDGTPFAMD YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEFE  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPASIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                451

SEQ ID NO: 5             moltype = AA  length = 448
```

```
FEATURE                 Location/Qualifiers
source                  1..448
                        mol_type = protein
                        organism = Homo sapiens
SEQUENCE: 5
QVQLVQSGAE VKKPGASVKL SCKASGYIFT RYYMYWVKQR PGQGLEWIGE INPNNGGTKF      60
NEKFKNRATL TVDKSISTAY MELSRLRSDD TAVYYCSRED DYDGTPFAMD YWGQGTLVTV     120
SSASTKGPSV FPLAPCSRST SESTAALGCL VKDYFPEPVT VSWNSGALTS GVHTFPAVLQ     180
SSGLYSLSSV VTVPSSSLGT KTYTCNVDHK PSNTKVDKRV ESKYGPPCPP CPAPEFEGGP     240
SVFLFPPKPK DTLMISRTPE VTCVVVDVSQ EDPEVQFNWY VDGVEVHNAK TKPREEQFNS     300
TYRVVSVLTV LHQDWLNGKE YKCKVSNKGL PSSIEKTISK AKGQPREPQV YTLPPSQEEM     360
TKNQVSLTCL VKGFYPSDIA VEWESNGQPE NNYKTTPPVL DSDGSFFLYS RLTVDKSRWQ     420
EGNVFSCSVM HEALHNHYTQ KSLSLSLG                                       448

SEQ ID NO: 6            moltype = AA  length = 214
FEATURE                 Location/Qualifiers
source                  1..214
                        mol_type = protein
                        organism = Homo sapiens
SEQUENCE: 6
DIQMTQSPSS LSASVGDRVT ITCHASQNIN VWLSWYQQKP GKAPKLLIYK ASNLHTGVPS      60
RFTGSGSGTD FTFTISSLQP EDIATYYCQQ GQTYPYTFGS GTKLEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 7            moltype = AA  length = 214
FEATURE                 Location/Qualifiers
source                  1..214
                        mol_type = protein
                        organism = Homo sapiens
SEQUENCE: 7
DIQMTQSPSS LSASVGDRVT ITCHASQNIN VWLSWYQQKP GKAPKLLIYK ASNLHTGVPS      60
RFSGSGSGTD FTFTISSLQP EDIATYYCQQ GQTYPYTFGQ GTKLEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 8            moltype = DNA  length = 1356
FEATURE                 Location/Qualifiers
source                  1..1356
                        mol_type = other DNA
                        organism = Homo sapiens
SEQUENCE: 8
caggtccaac tggtgcagtc tggggctgaa gtgaagaagc ctggggcttc agtgaagttg      60
tcctgcaagg cttctggcta catcttcacc agatactata tgtattgggt gaagcagagg     120
cctggacaag gccttgagtg gattggagag attaatccta acaatggtgg tactaagttc     180
aatgagaagt tcaagaacag ggccacactg actgtagaca atccatcag cacagcatac     240
atggagctca gcaggctgag atctgacgac acggcggtct attattgttc aagagaggat     300
gattacgacg ggacccccctt tgctatggac tactggggtc aaggaaccct ggtcaccgtc     360
tcctcagcct ccaccaaggg cccatcggtc ttccccctgg cacccctcctc caagagcacc     420
tctgggggca gcggccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagagagtt     660
gagcccaaat cttgtgacaa aactcacaca tgcccaccgt gcccagcacc tgaattcgag     720
gggggaccgt cagtcttcct cttccccca aaacccaagg acacccctca tgatctcccg     780
acccctgagg tcacatgcgt ggtggtggac gtgagccacg aagaccctga ggtcaagttc     840
aactggtacg tggacggcgt ggaggtgcat aatgccaaga caaagccgcg ggaggagcag     900
tacaacagca cgtaccgtgt ggtcagcgtc ctcaccgtcc tgcaccagga ctggctgaat     960
ggcaaggagt acaagtgcaa ggtctccaac aaagcccctcc cagcctccat cgagaaaacc    1020
atctccaaag ccaaagggca gccccgagaa ccacaggtgt acaccctgcc cccatcccgg    1080
gaagagatga ccaagaacca ggtcagcctg acctgcctgg tcaaaggctt ctatcccagc    1140
gacatcgccg tggagtggga gagcaatggg cagccggaga caactacaa gaccacgcct    1200
cccgtgctgg actccgacgg ctccttcttc ctctatagca agctcaccgt ggacaagagc    1260
aggtggcagc aggggaacgt cttctcatgc tccgtgatgc atgaggctct gcacaaccac    1320
tacacgcaga agagcctctc cctgtctccg ggttga                             1356

SEQ ID NO: 9            moltype = DNA  length = 1347
FEATURE                 Location/Qualifiers
source                  1..1347
                        mol_type = other DNA
                        organism = Homo sapiens
SEQUENCE: 9
caggtccaac tggtgcagtc tggggctgaa gtgaagaagc ctggggcttc agtgaagttg      60
tcctgcaagg cttctggcta catcttcacc agatactata tgtattgggt gaagcagagg     120
cctggacaag gccttgagtg gattggagag attaatccta acaatggtgg tactaagttc     180
aatgagaagt tcaagaacag ggccacactg actgtagaca atccatcag cacagcatac     240
atggagctca gcaggctgag atctgacgac acggcggtct attattgttc aagagaggat     300
gattacgacg ggacccccctt tgctatggac tactggggtc aaggaaccct ggtcaccgtc     360
tcctcagctt ccaccaaggg cccatcggtc ttccccctgg cgccctgctc caggagcacc     420
```

```
tccgagagca cagccgccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacg    600
aagacctaca cctgcaatgt agatcacaag cccagcaaca ccaaggtgga caagagagtt    660
gagtccaaat atggtccccc atgcccacca tgcccaggta actgagttcga ggggggacca    720
tcagtcttcc tgttccccc aaaacccaag gacactctca tgatctcccg gacccctgag    780
gtcacgtgcg tggtggtgga cgtgagccag gaagacccg aggtccagtt caactggtac    840
gtggatggcg tggaggtgca taatgccaag acaaagccgc gggaggagca gttcaacagc    900
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa    1020
gccaaaggc agccccgaga gccacaggt tacaccctgc cccatccca ggaggagatg    1080
accaagaacc aggtcagcct gacctgcctg gtcaaaggct tctaccccag cgacatcgcc    1140
gtggagtggg agagcaatgg gcagccggag aacaactaca agaccacgcc tcccgtgctg    1200
gactccgacg gctccttctt cctctacagc aggctaaccg tggacaagag caggtggcag    1260
gagggggaatg tcttctcatg ctccgtgatg catgaggctc tgcacaacca ctacacacag    1320
aagagcctct ccctgtctct gggttga                                        1347

SEQ ID NO: 10         moltype = DNA  length = 645
FEATURE               Location/Qualifiers
source                1..645
                      mol_type = other DNA
                      organism = Homo sapiens
SEQUENCE: 10
gacatccaga tgacccagtc tccatccagt ctgtctgcat ccgtaggaga cagagtcacc    60
atcacttgcc atgccagtca gaacattaat gtttggttat cttggtacca gcagaaacca    120
ggaaaagccc ctaaactctt gatctataag gcttccaact tgcacacagg cgtcccatca    180
agatttactg gcagtggatc tggaacagat ttcacattca ccatcagcag cctgcagcct    240
gaagacattg ccacttacta ctgtcaacag ggtcaaactt atccatacac gttcggacag    300
gggaccaagc tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                   645

SEQ ID NO: 11         moltype = DNA  length = 645
FEATURE               Location/Qualifiers
source                1..645
                      mol_type = other DNA
                      organism = Homo sapiens
SEQUENCE: 11
gacatccaga tgacccagtc tccatccagt ctgtctgcat ccgtaggaga cagagtcacc    60
atcacttgcc atgccagtca gaacattaat gtttggttat cgcagaaacca              120
ggaaaagccc ctaaactctt gatctataag gcttccaact tgcacacagg cgtcccatca    180
agatttagtg gcagtggatc tggaacagat ttcacattca ccatcagcag cctgcagcct    240
gaagacattg ccacttacta ctgtcaacag ggtcaaactt atccatacac gttcggacag    300
gggaccaagc tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                   645

SEQ ID NO: 12         moltype = AA  length = 5
FEATURE               Location/Qualifiers
source                1..5
                      mol_type = protein
                      organism = Homo sapiens
SEQUENCE: 12
RYYMY                                                                 5

SEQ ID NO: 13         moltype = AA  length = 17
FEATURE               Location/Qualifiers
source                1..17
                      mol_type = protein
                      organism = Homo sapiens
SEQUENCE: 13
EINPNNGGTK FNEKFKN                                                   17

SEQ ID NO: 14         moltype = AA  length = 13
FEATURE               Location/Qualifiers
source                1..13
                      mol_type = protein
                      organism = Homo sapiens
SEQUENCE: 14
EDDYDGTPFA MDY                                                       13

SEQ ID NO: 15         moltype = AA  length = 11
FEATURE               Location/Qualifiers
```

```
source                     1..11
                           mol_type = protein
                           organism = Homo sapiens
SEQUENCE: 15
HASQNINVWL S                                                                11

SEQ ID NO: 16              moltype = AA   length = 7
FEATURE                    Location/Qualifiers
source                     1..7
                           mol_type = protein
                           organism = Homo sapiens
SEQUENCE: 16
KASNLHT                                                                     7

SEQ ID NO: 17              moltype = AA   length = 9
FEATURE                    Location/Qualifiers
source                     1..9
                           mol_type = protein
                           organism = Homo sapiens
SEQUENCE: 17
QQGQTYPYT                                                                   9

SEQ ID NO: 18              moltype = AA   length = 513
FEATURE                    Location/Qualifiers
source                     1..513
                           mol_type = protein
                           organism = Homo sapiens
SEQUENCE: 18
MKMASFLAFL  LLNFRVCLLL  LQLLMPHSAQ  FSVLGPSGPI  LAMVGEDADL  PCHLFPTMSA      60
ETMELKWVSS  SLRQVVNVYA  DGKEVEDRQS  APYRGRTSIL  RDGITAGKAA  LRIHNVTASD     120
SGKYLCYFQD  GDFYEKALVE  LKVAALGSDL  HVDVKGYKDG  GIHLECRSTG  WYPQPQIQWS     180
NNKGENIPTV  EAPVVADGVG  LYAVAASVIM  RGSSGEGVSC  TIRSSLLGLE  KTASISIADP     240
FFRSAQRWIA  ALAGTLPVLL  LLLGGAGYFL  WQQQEEKKTQ  FRKKKREQEL  REMAWSTMKQ     300
EQSTRVKLLE  ELRWRSIQYA  SRGERHSAYN  EWKKALFKPA  DVILDPKTAN  PILLVSEDQR     360
SVQRAKEPQD  LPDNPERFNW  HYCVLGCESF  ISGRHYWEVE  VGDRKEWHIG  VCSKNVQRKG     420
WVKMTPENGF  WTMGLTDGNK  YRTLTEPRTN  LKLPKPPKKV  GVFLDYETGD  ISFYNAVDGS     480
HIHTFLDVSF  SEALYPVFRI  LTLEPTALTI  CPA                                    513

SEQ ID NO: 19              moltype = AA   length = 334
FEATURE                    Location/Qualifiers
source                     1..334
                           mol_type = protein
                           organism = Homo sapiens
SEQUENCE: 19
MKMASSLAFL  LLNFHVSLLL  VQLLTPCSAQ  FSVLGPSGPI  LAMVGEDADL  PCHLFPTMSA      60
ETMELKWVSS  SLRQVVNVYA  DGKEVEDRQS  APYRGRTSIL  RDGITAGKAA  LRIHNVTASD     120
SGKYLCYFQD  GDFYEKALVE  LKVAALGSNL  HVEVKGYKDG  GIHLECRSTG  WYPQPQIQWS     180
NAKGENIPAV  EAPVVADGVG  LYEVAASVIM  RGGSGEGVSC  IIRNSLLGLE  KTASISIADP     240
FFRSAQPWIA  ALAGTLPILL  LLLAGASYFL  WRQQKEITAL  SSEIESEQEM  KEMGYAATER     300
EISLRESLQE  ELKRKKIQYL  TRGEESSSDT  NKSA                                   334

SEQ ID NO: 20              moltype = AA   length = 584
FEATURE                    Location/Qualifiers
source                     1..584
                           mol_type = protein
                           organism = Homo sapiens
SEQUENCE: 20
MKMASSLAFL  LLNFHVSLFL  VQLLTPCSAQ  FSVLGPSGPI  LAMVGEDADL  PCHLFPTMSA      60
ETMELRWVSS  SLRQVVNVYA  DGKEVEDRQS  APYRGRTSIL  RDGITAGKAA  LRIHNVTASD     120
SGKYLCYFQD  GDFYEKALVE  LKVAALGSDL  HIEVKGYEDG  GIHLECRSTG  WYPQPQIKWS     180
DTKGENIPAV  EAPVVADGVG  LYAVAASVIM  RGSSGGGVSC  IIRNSLLGLE  KTASISIADP     240
FFRSAQPWIA  ALAGTLPISL  LLLAGASYFL  WRQQKEKIAL  SRETEREREM  KEMGYAATEQ     300
EISLRKLQE   ELKWRKIQYM  ARGEKSLAYH  EWKMALFKPA  DVILDPDTAN  AILLVSEDQR     360
SVQRAEEPRD  LPDNPERFEW  RYCVLGCENF  TSGRHYWEVE  VGDRKEWHIG  VCSKNVERKK     420
GWVKMTPENG  YWTMGLTDGN  KYRALTEPRT  NLKLPEPPRK  VGIFLDYETG  EISFYNATDG     480
SHIYTPPHAS  FSEPLYPVFR  ILTLEPTALT  ICPIPKEVES  SPDPDLVPDH  SLETPLTPGL     540
ANESGEPQAE  VTSLLLPAHP  GAEVSPSATT  NQNHKLQART  EALY                       584

SEQ ID NO: 21              moltype = AA   length = 243
FEATURE                    Location/Qualifiers
source                     1..243
                           mol_type = protein
                           organism = Macaca fascicularis
SEQUENCE: 21
MGSSLAFLLL  SFHVCVLLLQ  LLMPHSAQFA  VVGPPGPILA  MVGEDADLPC  HLFPTMSAET      60
MELRWVSSNL  RQVVNVYADG  KEVEDRQSAA  YRGRTSILRD  GITAGKAALR  IHNVTASDSG     120
KYLCYFQDGD  FYEKALVELK  VAALGSDLHI  DVKGYEDGGI  HLECRSTGWY  PQPQIRWSND     180
KGENIPAVEA  PVFVDGVGLY  AVAASVILRG  SSGEVSCTI   RSSLLGLEKT  TSISIAGHHH     240
HHH                                                                       243
```

```
SEQ ID NO: 22         moltype = AA  length = 243
FEATURE               Location/Qualifiers
source                1..243
                      mol_type = protein
                      organism = Macaca fascicularis
SEQUENCE: 22
MGSSLAFLLL NFHVSFFLVQ LLTPCSAQFS VLGPSGPILA MVGEDADLPC HLFPTMSAET   60
MELRWVSSSL RQVVNVYADG KEVEDRQSAP YRGRTSILRD DIAAGKAALR IHNVTASDSG  120
KYLCYFQDAD FYEKALVELK VAALGSNLHV EVKGYEDGGI HLECRSTGWY PQPKIQWSNA  180
KGQNIPAVEA PVVADGVGLY AVAASVIMRG GSGESVSCII RNSVLGLEKT ASISIADHHH  240
HHH                                                                243

SEQ ID NO: 23         moltype = AA  length = 243
FEATURE               Location/Qualifiers
source                1..243
                      mol_type = protein
                      organism = Macaca fascicularis
SEQUENCE: 23
MANFLAFLLL NFRVCLLLVQ LLTPCSAQFA VLGPHGPILA MVGEDVDLPC HLFPTMSAET   60
MELRWVSSSL RQVVNVYSDG KEVEDRQSAP YRGRTSILRD GITAGKAALR IHNVTASDSG  120
KYLCYFQDGD FYEKALVELK VAALGSDLHI EVKGYEDGGI HLECRSTGWY PQPQIQWSNT  180
KGQHIPAVKA PVVADGVGLY AVAASVIMRG SSGEGVSCII RNSLLGLEKT ASISITDHHH  240
HHH                                                                243
```

The invention claimed is:

1. An isolated anti-BTN3A antibody comprising a variable heavy chain polypeptide VH of SEQ ID NO:1 and a variable light chain polypeptide VL of SEQ ID NO:2.

2. The isolated anti-BTN3A antibody of claim 1, wherein the antibody binds to human BTN3A polypeptide with a KD of 10 nM or less as measured by surface plasmon resonance.

3. The isolated anti-BTN3A antibody of claim 1, wherein the antibody binds to human BTN3A polypeptide with a KD of 5 nM or less as measured by surface plasmon resonance.

4. The isolated anti-BTN3A antibody of claim 1, wherein the antibody induces activation of Vγ9Vδ2-T cells in co-culture with BTN3 expressing cells, with an $EC_{50}$ below 5 mg/ml as measured in a degranulation assay.

5. The isolated anti-BTN3A antibody of claim 1, wherein the antibody induces activation of Vγ9Vδ2-T cells in co-culture with BTN3 expressing cells, with an $EC_{50}$ below 1 mg/ml as measured in a degranulation assay.

6. The isolated anti-BTN3A antibody of claim 1, wherein the antibody comprises a silenced mutant IgG1 constant region.

7. The isolated anti-BTN3A antibody of claim 1, wherein the antibody comprises a IgG1 mutant Fc region with the following three amino acid substitutions: L247F, L248E, and P350S.

8. The isolated anti-BTN3A antibody of claim 1, wherein the antibody comprises a heavy chain of SEQ ID NO:4 and a light chain of SEQ ID NO:6.

9. A pharmaceutical composition comprising an anti-BTN3A antibody of claim 1, in combination with one or more of an agent selected from the group consisting of a pharmaceutically acceptable excipient, diluent and carrier.

10. A lyophilisate formulation, a pre-filled syringe or a vial comprising an anti-BTN3A antibody according to claim 1.

11. An expression vector for the recombinant production of an anti-BTN3A antibody of claim 1 in a host cell, comprising at least one nucleic acid encoding the heavy variable chain of SEQ ID NO:1 and a nucleic acid encoding the light variable chain of SEQ ID N:2 of said anti-BTN3A antibody.

12. The expression vector of claim 11, comprising a nucleic acid of SEQ ID NO:9 and a nucleic acid of SEQ ID NO:10 encoding respectively the heavy and light chains of said anti-BTN3A antibody.

13. A mammalian host cell comprising an expression vector according to claim 11.

14. A process for the manufacturing of an anti-BTN3A antibody, comprising: (i) culturing the host cell of claim 13 for expression of said antibody by the host cell; optionally (ii) purifying said antibody; and (iii) recovering the antibody.

* * * * *